United States Patent
Bolin et al.

(10) Patent No.: US 8,124,766 B2
(45) Date of Patent: Feb. 28, 2012

(54) INHIBITORS OF DIACYLGLYCEROL ACYLTRANSFERASE

(75) Inventors: David Robert Bolin, Montclair, NJ (US); Stuart Hayden, Manalapan, NJ (US); Yimin Qian, Wayne, NJ (US); Weiya Yun, Warren, NJ (US)

(73) Assignee: Madrigal Pharmaceuticals, Inc., San Francisco, CA (US)

( * ) Notice: Subject to any disclaimer, the term of this patent is extended or adjusted under 35 U.S.C. 154(b) by 189 days.

(21) Appl. No.: 12/621,109

(22) Filed: Nov. 18, 2009

(65) Prior Publication Data

US 2010/0145047 A1 Jun. 10, 2010

Related U.S. Application Data

(60) Provisional application No. 61/119,467, filed on Dec. 3, 2008.

(51) Int. Cl.
*C07D 403/02* (2006.01)
*C07D 401/02* (2006.01)
*C07D 333/00* (2006.01)

(52) U.S. Cl. .................. 544/364; 546/278.1; 549/57

(58) Field of Classification Search .................. 544/364; 546/278.1; 549/57
See application file for complete search history.

(56) References Cited

U.S. PATENT DOCUMENTS

| | | | |
|---|---|---|---|
| 3,250,771 A | 5/1966 | Leonard et al. | |
| 3,929,793 A | 12/1975 | Popelak et al. | |
| 4,066,654 A | 1/1978 | Adelstein et al. | |
| 7,094,896 B2 | 8/2006 | Ding et al. | |
| 7,244,727 B2 | 7/2007 | Fox et al. | |
| 2004/0019067 A1 | 1/2004 | Armistead et al. | |
| 2007/0123504 A1 | 5/2007 | Bolin et al. | |

FOREIGN PATENT DOCUMENTS

| | | | |
|---|---|---|---|
| EP | 1535915 A | | 6/2005 |
| WO | 03020269 A | | 3/2003 |
| WO | 2006134317 A | | 12/2006 |
| WO | 2007/060140 A | | 5/2007 |
| WO | 2008141976 A1 | | 11/2008 |

OTHER PUBLICATIONS

The International Search Report and Written Opinion by the International Searching Authority, issued on Apr. 2, 2010, in the PCT application No. PCT/US09/64971.
The International Search Report and Written Opinion by the International Searching Authority, issued on Jul. 30, 2008, in the PCT application No. PCT/EP2008/055843.
The International Search Report and Written Opinion by the International Searching Authority, issued on Mar. 2, 2010, in the PCT application No. PCT/US09/68048.
The restriction requirement for U.S. Appl. No. 12/113,295, issued on Mar. 3, 2010.
The restriction requirement for U.S. Appl. No. 12/113,275, issued on Mar. 10, 2010.
Mishra et al., "A molecular model for diacylglycerol acyltransferase from *Mortierella ramanniana* var. *angulispora*," Bioinformation. 2009; 3(9): 394-398.
Oh et al., "Diacylglycerol acyltransferase-inhibitory compounds from *Erythrina senegalensis*," Archives of Pharmacal Research, 32(1), pp. 43-47, Jan. 2009.
Birch et al., "Discovery of a potent, selective, and orally efficacious pyrimidinooxazinyl bicyclooctaneacetic acid diacylglycerol acyltransferase-1 inhibitor," J. Med. Chem. Mar. 26, 2009;52(6):1558-68.
Zhao et al., "Validation of Diacyl Glycerolacyltransferase I as a Novel Target for the Treatment of Obesity and Dyslipidemia Using a Potent and Selective Small Molecule Inhibitor," J. Med. Chem., 2008, 51 (3), pp. 380-383.

*Primary Examiner* — Rebecca Anderson
*Assistant Examiner* — Samantha Shterengarts
(74) *Attorney, Agent, or Firm* — Mintz Levin Cohn Ferris Glovsky and Popeo, P.C.; Ivor R. Elrifi; Heidi A. Erlacher

(57) ABSTRACT

Provided herein are compounds of the formula (I):

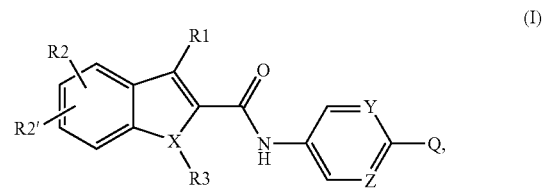

as well as pharmaceutically acceptable salts thereof, wherein the substituents are as those disclosed in the specification. These compounds, and the pharmaceutical compositions containing them, are useful for the treatment of diseases such as, for example, obesity, type II diabetes mellitus and metabolic syndrome.

52 Claims, No Drawings

INHIBITORS OF DIACYLGLYCEROL ACYLTRANSFERASE

CROSS-REFERENCED TO RELATED APPLICATIONS

This application claims priority from U.S. Provisional Ser. No. 61/119,467, filed Dec. 3, 2008, the disclosure of which is incorporated herein in its entirety.

FIELD OF THE INVENTION

The invention involves inhibitors of diacylglycerol acyltransferase. The inhibitors are useful for the treatment of diseases such as obesity, type II diabetes mellitus, dyslipidemia and metabolic syndrome.

All documents cited or relied upon below are expressly incorporated herein by reference.

BACKGROUND OF THE INVENTION

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets—Immune, Endocrine & Metabolic Disorders (2003) 3, 263-270).

Diacylglycerol O-acyltransferase, also known as diglyceride acyltransferase or DGAT, is a key enzyme in triglyceride synthesis. DGAT catalyzes the final and rate-limiting step in triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, 395-400).

DGAT has a specificity for sn-1,2 diacylglycerols and will accept a wide variety of fatty acyl chain lengths (see Farese et al, Current Opinions in Lipidology (2000) 11, 229-234). DGAT activity levels increase in fat cells as they differentiate in vitro and recent evidence suggests that DGAT may be regulated in adipose tissue post-transcriptionally (see Coleman et al, Journal of Molecular Biology (1978) 253, 7256-7261 and Yu et al, Journal of Molecular Biology (2002) 277, 50876-50884). DGAT activity is primarily expressed in the endoplasmic reticulum (see Colman, Methods in Enzymology (1992) 209, 98-104). In hepatocytes, DGAT activity has been shown to be expressed on both the cytosolic and luminal surfaces of the endoplasmic reticular membrane (see Owen et al, Biochemical Journal (1997) 323 (pt 1), 17-21 and Waterman et al, Journal of Lipid Research (2002) 43, 1555-156). In the liver, the regulation of triglyceride synthesis, and partitioning, between retention as cytosolic droplets and secretion, is of primary importance in determining the rate of VLDL production (see Shelness and Sellers, Current Opinions in Lipidology (2001) 12, 151-157 and Owen et al, Biochemical Journal (1997) 323 (pt 1), 17-21).

Two forms of DGAT have been cloned and are designated DGAT1 and DGAT2 (see Cases et al, Proceedings of the National Academy of Science, USA (1998) 95, 13018-13023, Lardizabal et al, Journal of Biological Chemistry (2001) 276, 38862-38869 and Cases et al, Journal of Biological Chemistry (2001) 276, 38870-38876). Although both enzymes utilize the same substrates, there is no homology between DGAT1 and DGAT2. Both enzymes are widely expressed however some differences do exist in the relative abundance of expression in various tissues.

The gene encoding mouse DGAT1 has been used to create DGAT knock-out. These mice, although unable to express a functional DGAT enzyme (Dgat−/− mice), are viable and continue to synthesize triglycerides (see Smith et al, Nature Genetics (2000) 25, 87-90). This would suggest that multiple catalytic mechanisms contribute to triglyceride synthesis, such as DGAT2. An alternative pathway has also been shown to form triglycerides from two diacylglycerols by the action of diacylglycerol transacylase (see Lehner and Kuksis, Progress in Lipid Research (1996) 35, 169-210).

Dgat−/− mice are resistant to diet-induced obesity and remain lean. When fed a high fat diet, Dgat−/− mice maintain weights comparable to mice fed a diet with regular fat content. Dgat−/− mice have lower tissue triglyceride levels. The resistance to weight gain seen in the knockout mice, which have a slightly higher food intake, is due to an increased energy expenditure and increased sensitivity to insulin and leptin (see Smith et al, Nature Genetics (2000) 25, 87-90, Chen and Farese, Trends in Cardiovascular Medicine (2000) 10, 188-192, Chen and Farese, Current Opinions in Clinical Nutrition and Metabolic Care (2002) 5, 359-363 and Chen et al, Journal of Clinical Investigation (2002) 109, 1049-1055). Dgat−/− mice have reduced rates of triglyceride absorption, improved triglyceride metabolism, and improved glucose metabolism, with lower glucose and insulin levels following a glucose load, in comparison to wild-type mice (see Buhman et al, Journal of Biological Chemistry (2002) 277, 25474-25479 and Chen and Farese, Trends in Cardiovascular Medicine (2000) 10, 188-192).

Disorders or imbalances in triglyceride metabolism, both absorption as well as de novo synthesis, have been implicated in the pathogenesis of a variety of disease risks. These include obesity, insulin resistance syndrome, type II diabetes, dyslipidemia, metabolic syndrome (syndrome X) and coronary heart disease (see Kahn, Nature Genetics (2000) 25, 6-7, Yanovski and Yanovski, New England Journal of Medicine (2002) 346, 591-602, Lewis et al, Endocrine Reviews (2002) 23, 201, Brazil, Nature Reviews Drug Discovery (2002) 1, 408, Malloy and Kane, Advances in Internal Medicine (2001) 47, 111, Subauste and Burant, Current Drug Targets—Immune, Endocrine & Metabolic Disorders (2003) 3, 263-270 and Yu and Ginsberg, Annals of Medicine (2004) 36, 252-261). Compounds that can decrease the synthesis of triglycerides from diacylglycerol by inhibiting or lowering the activity of the DGAT enzyme would be of value as therapeutic agents for the treatment of diseases associated with abnormal metabolism of triglycerides.

Known inhibitors of DGAT include: dibenzoxazepinones (see Ramharack, et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, 683-687 and Casaschi et al, Journal of Nutrition (2004) 134, 1340-1346), substituted benzyl-phosphonates (see Kurogi et al, Journal of Medicinal Chemistry (1996) 39, 1433-1437, Goto, et al, Chemistry and Pharmaceutical Bulletin (1996) 44, 547-551, Ikeda, et al, Thirteenth International Symposium on Atherosclerosis (2003), abstract 2P-0401, and Miyata, et al, JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), substituted sulfonamides (see Budd Haeberlein and Buckets, WO20050442500), thiophenoxyacetamides (see Bolin and Michoud, WO2006082010), arylpropionylhydrazides (see Michaud, WO2006120125) and oxazoledicarboxamides (see Bolin et al, WO2007060140). Most recently, DGAT inhibitors demonstrated efficacy of body weight gain inhibition in obese animal models (Journal of Medicinal Chemistry (2008), 51, 380).

Also known to be inhibitors of DGAT are: 2-bromo-palmitic acid (see Colman et al, Biochimica et Biophysica Acta (1992) 1125, 203-9), 2-bromo-octanoic acid (see Mayorek and Bar-Tana, Journal of Biological Chemistry (1985) 260, 6528-6532), roselipins (see Noriko et al, (Journal of Antibiotics (1999) 52, 815-826), amidepsin (see Tomoda et al, Journal of Antibiotics (1995) 48, 942-7), isochromophilone, prenylflavonoids (see Chung et al, Planta Medica (2004) 70, 258-260), polyacetylenes (see Lee et al, Planta Medica (2004) 70, 197-200), cochlioquinones (see Lee et al, Journal of Antibiotics (2003) 56, 967-969), tanshinones (see Ko et al, Archives of Pharmaceutical Research (2002) 25, 446-448), gemfibrozil (see Zhu et al, Atherosclerosis (2002) 164, 221-228), and substituted quinolones (see Ko, et al, Planta Medica (2002) 68, 1131-1133). Also known to be modulators of DGAT activity are antisense oligonucleotides (see Monia and Graham, US20040185559).

A need exists in the art, however, for additional DGAT inhibitors that have efficacy for the treatment of metabolic disorders such as, for example, obesity, type II diabetes mellitus and metabolic syndrome.

SUMMARY OF THE INVENTION

The present invention pertains to DGAT inhibitors. In a preferred embodiment, the invention provides for compounds of the formula (I):

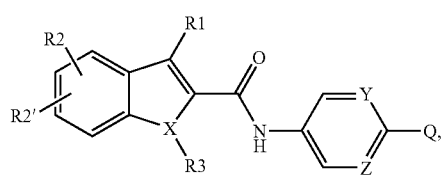

(I)

as well as pharmaceutically acceptable salts thereof, and pharmaceutical compositions thereof.

DETAILED DESCRIPTION OF THE INVENTION

In a preferred embodiment of the present invention, provided are compounds of formula (I):

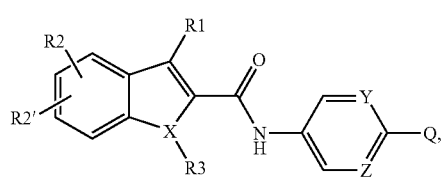

(I)

wherein:
X is oxygen, sulfur or nitrogen;
Y is carbon or nitrogen;
Z is carbon or nitrogen;

R1 is lower alkyl, halo lower alkyl, alkoxy, lower alkyl alkoxy or hydrogen;
R2, R2', independently of each other, is halogen, alkoxy, lower alkyl, haloloweralkyl, haloalkoxy, benzyloxy or hydrogen;
R3 is hydrogen or lower alkyl, wherein if X is oxygen or sulfur, then R3 is absent; and
Q is piperazine-1-carboxylic acid lower alkyl ester, piperazine-1-carboxylic acid lower alkyl ester, piperazin-1-yl-2, 2-dimethyl-4-oxo-lower akanoic acid, piperidin-1-yl-2,2-dimethyl-4-oxo-lower alkanoic acid, piperazine-1-carbonyl-4-cyclohexanecarboxylic acid benzyl ester, piperazine-1-carbonyl-4-cyclohexanecarboxylic acid, piperidine-1-carbonyl-4-cyclohexanecarboxylic acid, piperazine-1-carbonyl-2-cyclopentanecarboxylic acid, N-lower alkoxy lower alkyl-N-lower alkyl-amino, N-cyclolower alkyl-N-lower alkyl-amino, N-pyrrolidine-1-carboxylic acid lower alkyl ester, O-pyrrolidine-1-carboxylic acid lower alkyl ester, O-pyrrolidine-1-carboxylic acid lower alkyl ester, pyrrolidine-3-ylamino-1-carboxylic acid lower alkyl ester, pyrrolidin-3-ylamino-1-carboxylic acid lower alkyl amide, piperidin-1-yl-4-oxo-2-phenyl-lower alkanoic acid, piperidine-1-carbonyl-2-cyclopentanecarboxylic acid, piperidin-1-yl-2-oxo-lower alkyl-cyclopentanecarboxylic acid, piperazin-1-yl-4-oxo-lower alkyl acid, piperidin-1-yl-4-oxo-lower alkanoic acid, piperazin-1-yl-2-oxo-ethyl-3-methyl-lower alkanoic acid, piperazin-1-yl-4-oxo-2-cyclohexyl-butyric acid, pyrrolidine-3-oxy-1-carboxylic acid lower alkyl ester, pyrrolidine-3-oxy-1-carboxylic acid lower alkyl ester, pyrrolidin-3-oxy-1-yl-2, 2-dimethyl-4-oxo-lower alkanoic acid, pyrrolidin-3-oxy-1-yl-4-benzoic acid, 2,4-dioxo-thiazolidin-5-yl-acetyl-piperazin-1-yl or piperazin-1-yl-4-benzoic acid,
or a pharmaceutically acceptable salt thereof.

In another preferred embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents, with the understanding that said substituents are not, in turn, substituted further unless indicated otherwise. Each substituent can independently be, for example, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, azetidine, morpholinyl, thiomorpholinyl, piperazinyl, piperidinyl, pyrrolidinyl, tetrahydropyranyl, tetrahydrofuranyl, 1,3-dioxanyl, thiazolidine-2,4-dione and the like. The heterocycloalkyl groups may be unsubstituted or substituted and attachment may be through their carbon frame or through their heteroatom(s) where appropriate, with the understanding that said substituents are not, in turn, substituted further.

The term "lower alkyl", alone or in combination with other groups, refers to a branched or straight-chain alkyl radical of one to nine carbon atoms, preferably one to six carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, loweralkyl and aryl groups may be substituted or unsubstituted. When substituted, there will generally be, for example, 1 to 4 substituents present, with the understanding that said substituents are not, in turn, substituted further unless indicated otherwise. These substituents may optionally form a ring with the alkyl, loweralkyl or aryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless indicated otherwise. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfonyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, (uranyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term lower alkyl denoted monovalent saturated aliphatic hydrocarbons containing from 1 to 6 carbon atoms such as methyl, ethyl, isopropyl, tertiary butyl, etc. As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further unless indicated otherwise. The term lower alkoxy denotes monovalent alkoxy groups containing from 1 to 6 carbom\n atoms such as methoxy, ethoxy butoxy, etc. The term lower alkanoic acid designates monovalent saturated aliphatic mono carboxylic acids containing from 2 to 6 carbon atoms such as acetic acid, propionic acid, butyric acid etc. the term cyclo lower alkyl designates monovalent saturated cyclo lower alkyl groups containing a ring of 3 to 6 carbon atoms such as cyclopropyl, cyclohexyl cyclobutyl, etc.

As used herein, the term "halogen" means a fluorine, chlorine, bromine or iodine radical, preferably a fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

Compounds of the present invention can be prepared from commercially available starting materials or by the use of general synthetic techniques and procedures that are known to those skilled in the art. Outlined below are reaction schemes suitable for the preparation of such compounds. Further exemplification can be found in the specific examples detailed below.

The required substituted benzofuran, benzothiophene and indole derivatives were purchased from commercially available sources. In the cases where the desired heterocycle compounds are not commercially available, the preparation of 6,5-fused heterocycles were carried out according to Scheme 1.

Scheme 1: Preparation of indole and benzothiophene

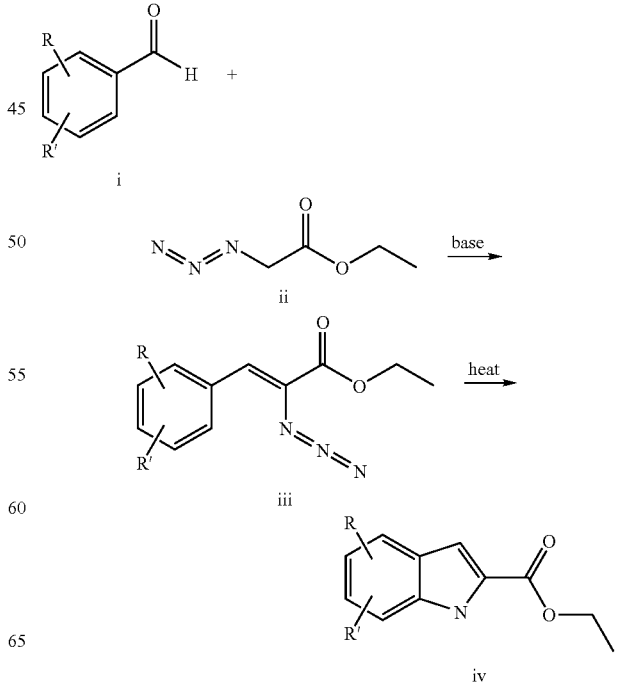

-continued

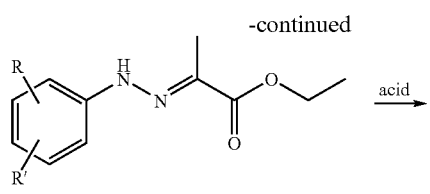

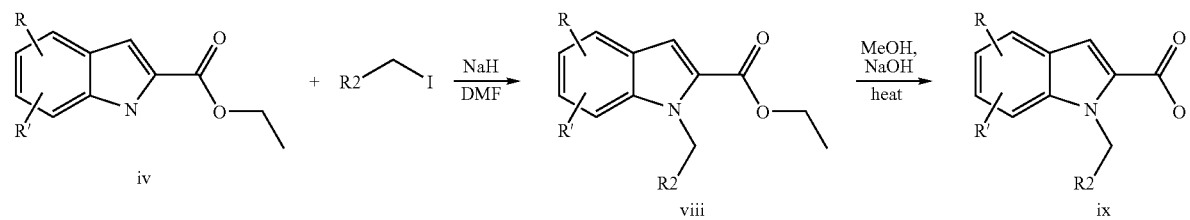

As described in literature (*Journal of the Chemical Society, Chemical Communications* 14, 627, 1979), commercially available substituted benzaldehyde (i) was reacted with azidoacetic acid ethyl ester (ii) under basic conditions. The condensation product acrylic acid derivative (iii) was heated to give an intermediate nitrene which underwent ring insertion to provide the desired indole-2-carboxylic acid derivatives (iv), where R and R' can be alkyl, alkoxy and halogen.

Alternatively, indole derivative (iv) can also be prepared by using Fisher indole synthesis as described in literature (*Chemical and Pharmaceutical Bulletin* 22, 1981, 1974). The desired aryl hydrazone (v) can be prepared from the corresponding aryl hydrazine and ethyl ester of 2-oxo-propionic acid. Under acidic conditions, hydrazone (v) can rearrange to indole-2-carboxylic acid ethyl ester.

For the substituted benzothiophene-2-carboxylic acid, the preparation was carried out according to literature example (*Tetrahedron Letters* 44, 7147, 2003). The substitution of fluorine in compound (vi) by 2-mercaptoacetic acid methyl ester followed by intra-molecular condensation under basic conditions provided benzothiophene-2-carboxylic acid methyl ester, where R1 can be alkyl and fluorine substituted alkyl groups such as trifluoromethyl, R and R' can be alkyl, alkoxy and halogen.

The required N-alkyl indole-2-carboxylic acid can be prepared from compound (iv) as illustrated in Scheme 2.

Scheme 2: Preparation of N-alkyl-indole-2-carboxylic acid

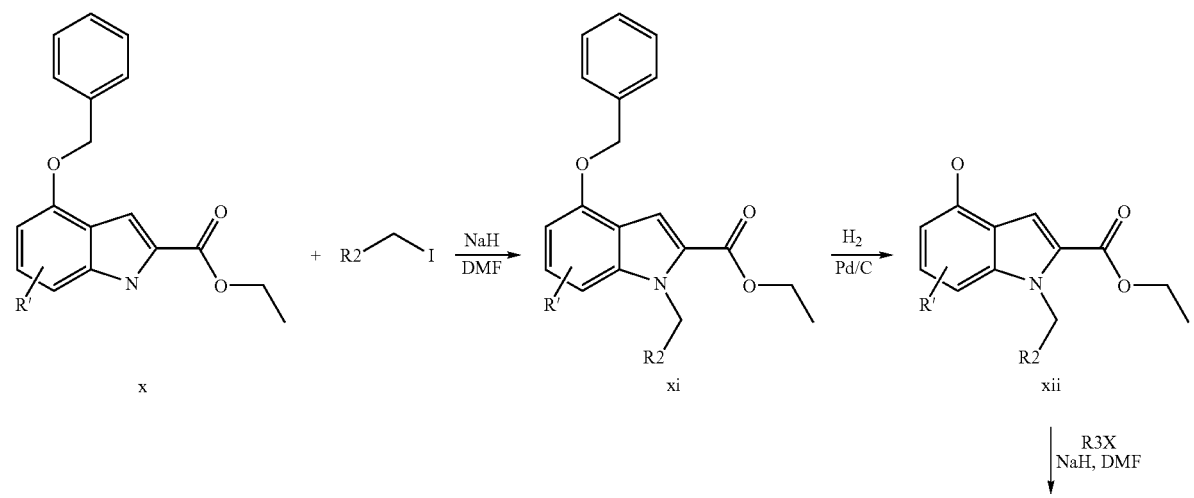

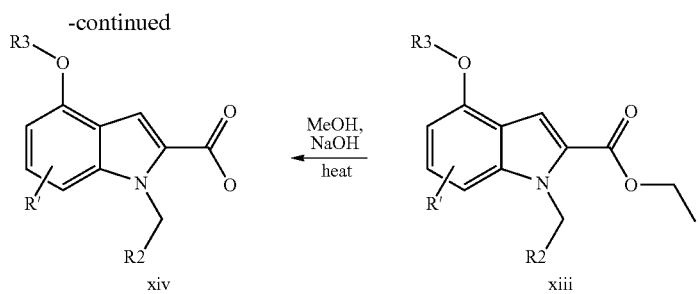

As described in Scheme 2, substituted indole-2-carboxylic acid ethyl ester (iv) was alkylated at N–1 position under basic conditions, such as sodium hydride, where R2 can be hydrogen, methyl, ethyl and other small alkyl groups. The N-alkylated compound (viii) was hydrolyzed in the presence of sodium hydroxide in methanol. The reaction was heated in microwave to facilitate the process. To install different alkoxy groups at 4, 5 or other positions of indole, commercially available benzyloxy substituted indole (x) was used as a starting material. In the presence of sodium hydride, compound (x) was alkylated to provide N–1 alkylated compound (xi).

Catalytic hydrogenation of compound (xi) gave compound (xii). Alkylation of compound (xii) with alkyl halide in the presence of sodium hydride provided alkoxy substituted indole derivative (xiii), where R3 can be methyl, ethyl, isobutyl and other small alkyl or fluorine substituted small alkyl groups. Saponification of compound (xiii) gave the desired alkoxy substituted N-alkylindole-2-carboxylic acid (xiv).

To prepare DGAT inhibitors such as, for example, compound (xxiii), reactions illustrated in Scheme 3 were carried out.

Scheme 3: Preparation of preferred carboxylic acids or carbamates

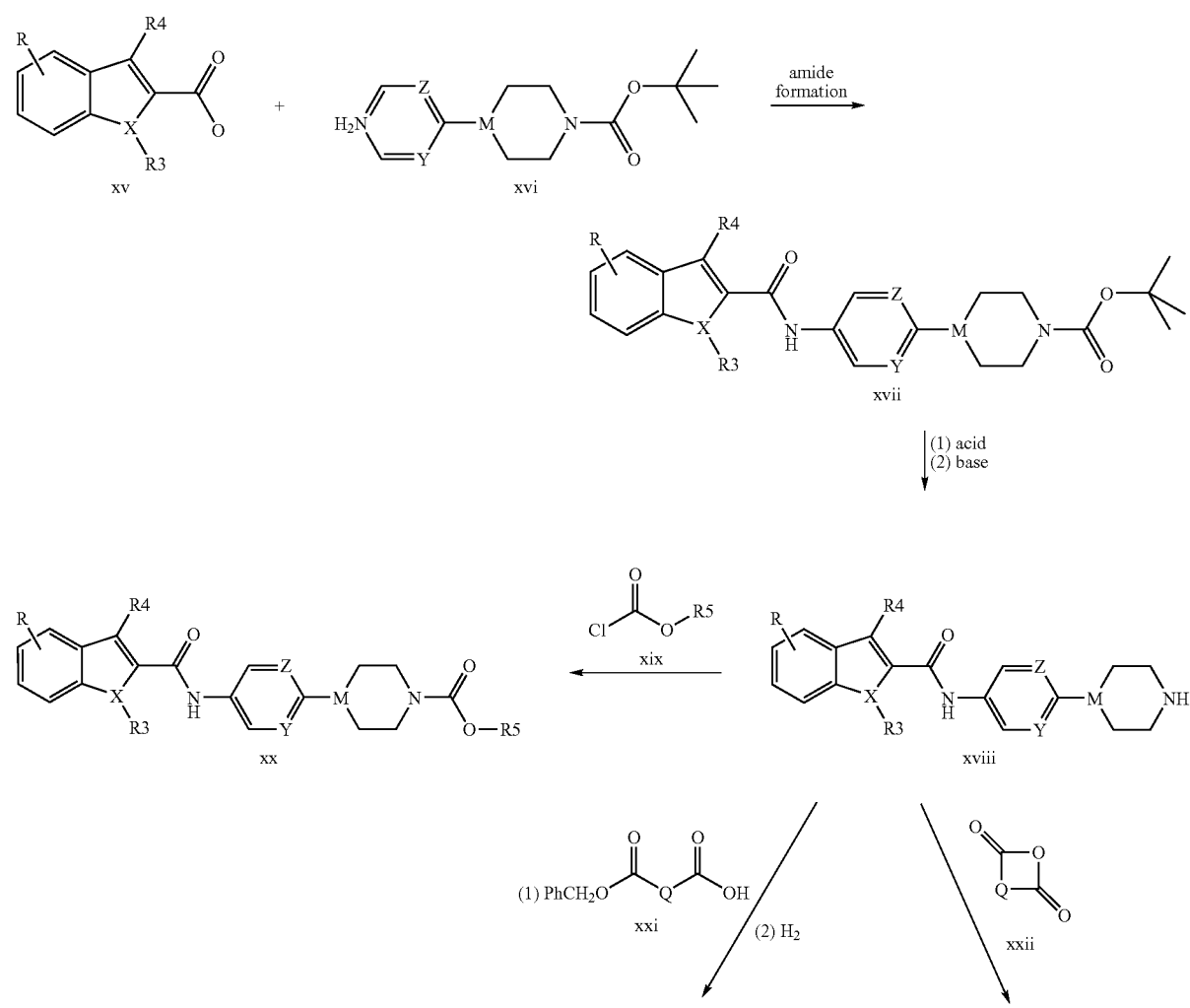

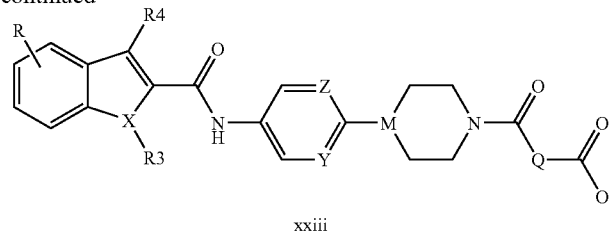

xxiii

As described in Scheme 3, benzofuran-, benzothiophene- or indole-2-carboxylic acid (compound xv) was coupled with arylamine derivative (compound xvi) under amide formation conditions such as through acid chloride intermediates or using coupling reagent to provide compound xvii, where R in compound xv can be alkyl, alkoxy or halogen, R substitution on the aryl ring can be mono- or di-substitution, R3 can be hydrogen or alkyl group, R4 can be hydrogen or alkyl group, and X can be oxygen, sulfur or nitrogen. In the cases where X is oxygen or sulfur, R3 in compound xv is absent. For compound xvi, Y and Z can be nitrogen or carbon, M can be nitrogen or carbon. The cleavage of N-butoxy carbonyl group in compound xvii was carried out under acidic conditions and the resulting amine salt was neutralized to give a key intermediate xviii. The reaction of intermediate xviii with chloroformate xix provided desired carbamate xx, where R5 in compound xx can be alkyl group.

Alternatively, intermediate xviii was also reacted with dicarboxylic acid mono-benzyl ester xxi under the amide formation conditions such as through acid chloride intermediate. Cleavage of the benzyl group provided the desired carboxylic acid xxiii, where Q in compound xxi can be cyclic or acyclic structure. In the cases where Q in xxi was a cyclic structure, both cis- and trans-carboxylic acids were prepared.

Carboxylic acid xxiii was also prepared by treating intermediate xviii with an anhydride xxii, where Q in compound xxii can be alkyl or substituted alkyl group. Q in compound xxii can also be a cyclic alkyl group. The cyclic anhydrides or spiro anhydrides were purchased from commercial sources.

When the arylamine was substituted by a di-alkyl amine, pyrrolidine amine or pyrrolidinyloxy groups, the synthesis of desired DGAT inhibitors were carried out according to Scheme 4.

Scheme 4: Preparation of 6,5-fused carboxamides with aryl substitution

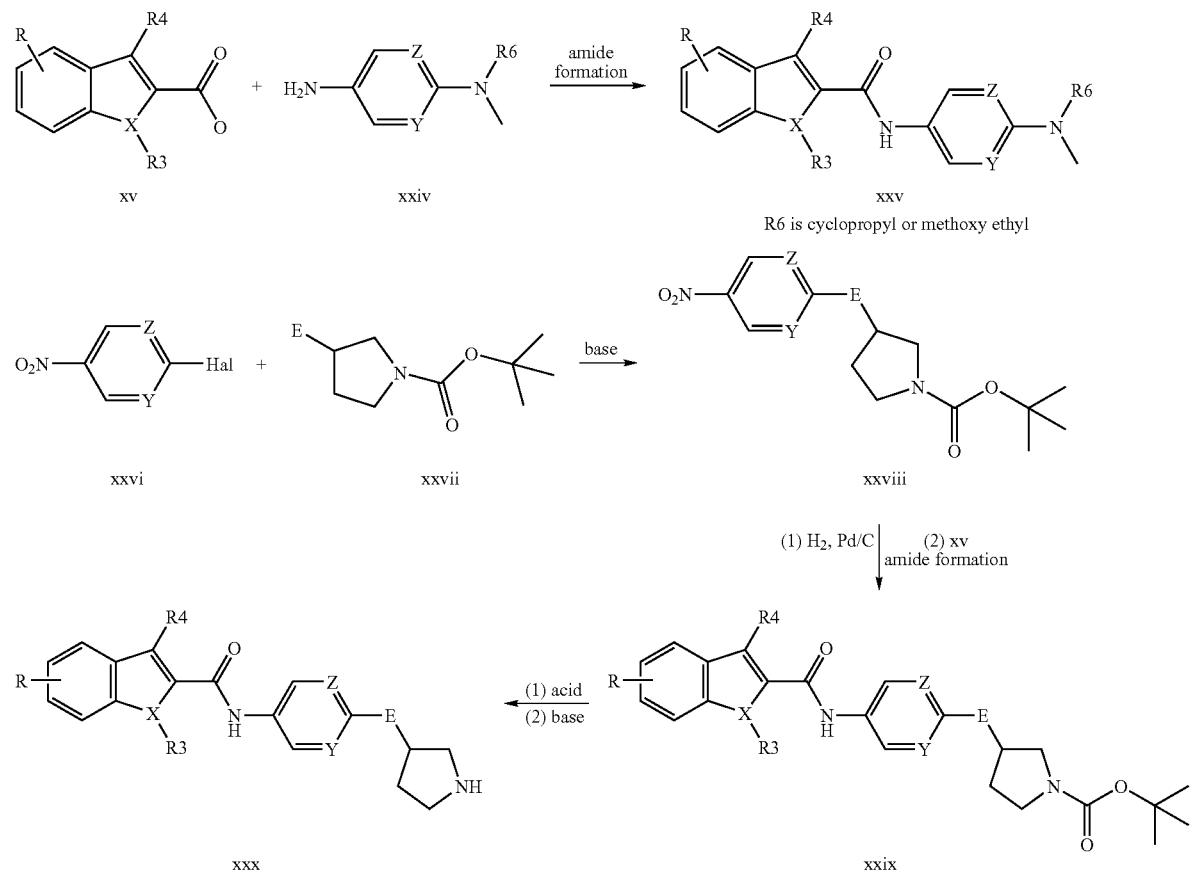

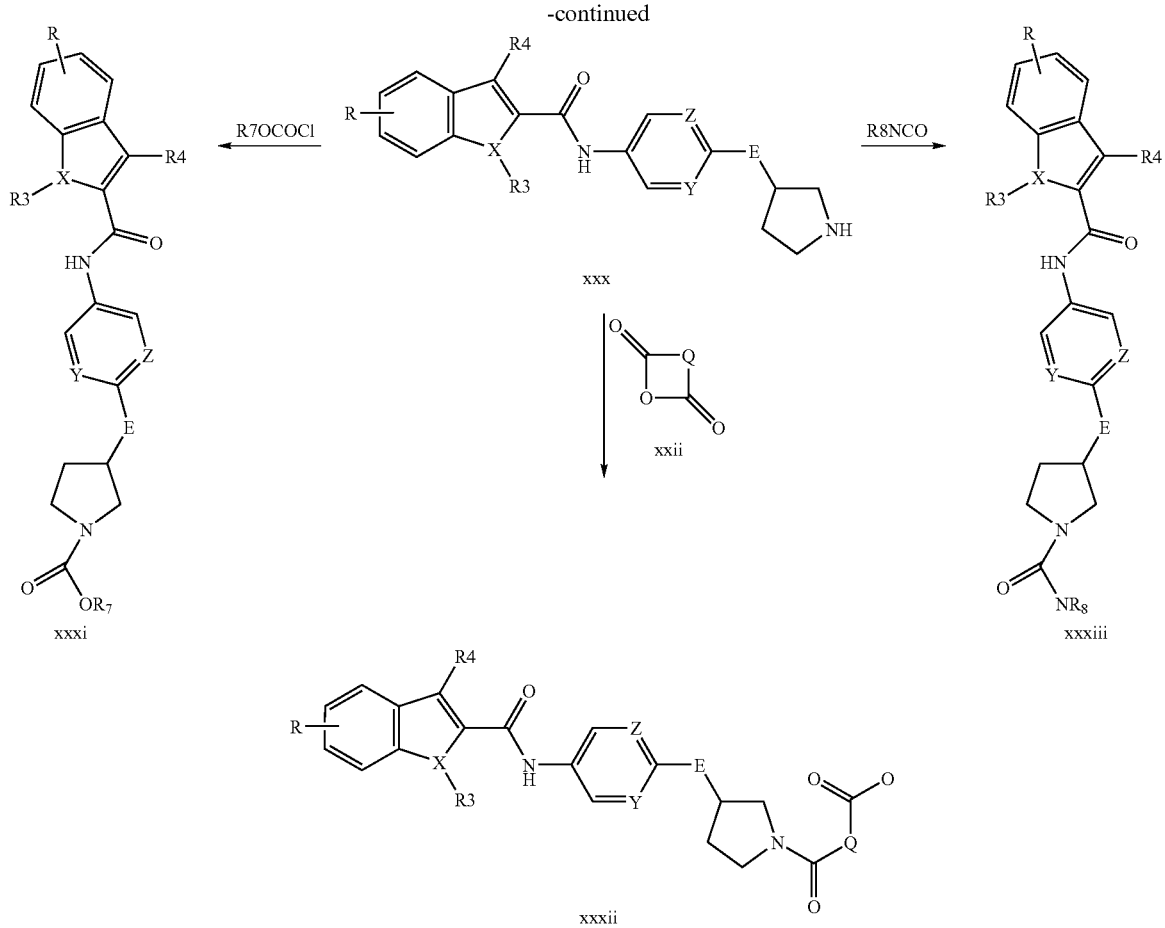

As shown in Scheme 4, substituted benzofuran-, benzothiophene- and indole-2-carboxylic acid were coupled with dialkyl substituted aryl amine xxiv to provide desired compound xxv, where R6 in xxiv was cyclopropyl or 2-methoxyethyl group, Y and Z can be nitrogen or carbon.

For pyrrolidineamino or pyrrolidinyloxy substituted aryl derivatives, 4-fluoronitrobenzene (Y and Z are carbon in xxvi) or 2-chloro-5-nitropyridine (Y is nitrogen and Z is carbon in xxvi) was reacted with 3-aminopyrrolidine-1-carboxylic acid tert-butyl ester (E is amino group in xxvii) or 3-hydroxypyrrolidine-1-carboxylic acid tert-butyl ester (E is hydroxyl group is xxvii) under basic conditions to provide compound xxviii. Reduction of the nitro group followed by amide formation with compound xv provided compound xxix, which was further converted to a key intermediate xxx through acidic cleavage.

Intermediate xxx was reacted with chloroformate or isocyanate to provide the corresponding carbamate xxxi or urea xxxiii, where R7 and R8 can be alkyl groups. Alternatively, intermediate xxx was also converted to a carboxylic acid xxxii by treating with anhydride xxii, where Q in xxii can be alkyl or substituted alkyl group. Further more, Q in compound xxii can also be a cyclic alkyl group. The cyclic anhydrides or Spiro anhydrides were purchased from commercial sources.

The key intermediate xviii in Scheme 3 and intermediate xxx in Scheme 4 were also converted to a corresponding aryl carboxylic acid through Buchwald coupling reaction as described in Scheme 5.

Scheme 5: Preparation of 6,5-fused carboxamides with aryl carboxylic acid and heterocyclic amides

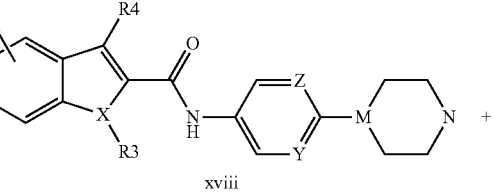

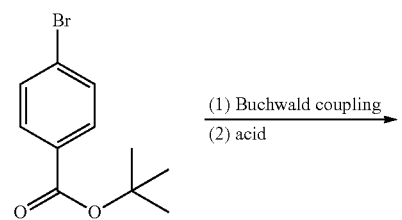

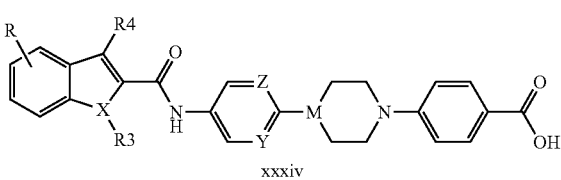

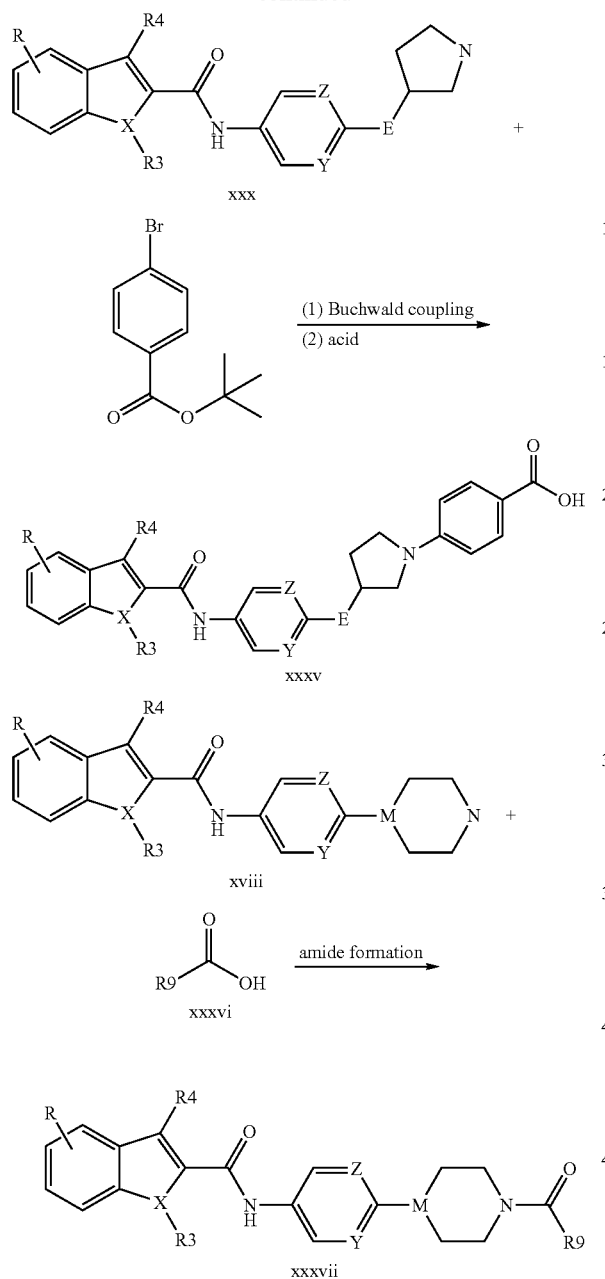

The amine intermediate xviii and xxx were treated with 4-bromobenzoic acid tert-butyl ester in the presence of palladium catalyst and phosphine ligands to produce the corresponding aryl amine which was further converted to compound xxxiv and xxxv by treating with acid to remove the tert-butyl ester. The Buchwald amination reaction was carried out with a similar method reported in literature (*Journal of the American Chemical Society* 125, 6653, 2003). The structure definition of compound xviii and xxx is the same as described in Scheme 3 and Scheme 4.

Finally, intermediate xviii was also reacted with carboxylic acid xxxvi under amide coupling conditions to produce compound xxxvii, where R9 in compound xxxvi can be alkyl or heterocycle substituted alkyl groups such as thiazolidinedione.

EXAMPLES

List of Abbreviations

DGAT is diacylglycerol:acyl CoA O-acyltransferase
THF is tetrahydrofuran
DMF is N,N-dimethylformamide
DMA is N,N-dimethylacetamide
DMSO is dimethylsulfoxide
DCM is dichloromethane
DME is dimethoxyethane
MeOH is methanol
EtOH is ethanol
EtOAc is ethyl acetate
NaOH is sodium hydroxide
TFA is trifluoroacetic acid
HOBT is 1-hydroxybenzotriazole
DMAP is 4-(dimethylamino)pyridine
$Pd_2(dba)_3$ is tris(dibenzylideneacetone)dipalladium
X-PHOS is (2',4',6'-triisopropyl-1,1'-biphenyl-2-yl)dicyclohexylphosphine
PyBroP is bromotripyrrolidinophosphonium hexafluorophosphate
BOP is (benzotriazol-1-yloxy)tris(dimethylamino)phosphonium hexafluorophosphate
EDCI is 1-[3-(dimethylamino)propyl]-3-ethylcarbodiimide hydrochloride
DIPEA is diisopropylethyl amine
BOC is butoxycarbonyl
Brine is saturated aqueous sodium chloride solution
DAG is 1,2-dioleoyl-sn-glycerol
TLC is thin layer chromatography
RP HPLC is reverse phase high performance liquid chromatography
APCI-MS is electrospray mass spectrometry
LCMS is liquid chromatography mass spectrometry
NMR is nuclear magnetic resonance spectroscopy
HRMS is high resolution mass spectrometry
LRMS is low resolution mass spectrometry
RT is room or ambient temperature.

Part I: Preparation of Preferred Intermediates 4,5-Dichloro-1H-indole-2-carboxylic acid ethyl ester

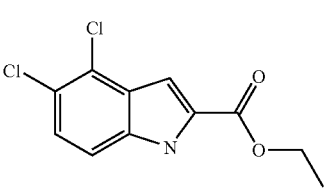

The preparation of this compound was carried out according to the method described in literature (*Journal of the Chemical Society, Chemical Communications* 14, 627, 1979). Briefly, a mixture of sodium (2.0 g, 87 mmol) and ethanol (350 mL) was stirred at room temperature until a homogeneous solution was observed (1.0 hr). A mixture of 2,3-dichlorobenzaldehyde (3.90 g, 22.3 mmol) and ethyl azidoacetate (11.2 g, 86.9 mmol) diluted in 50 mL of ethanol was added slowly at 0° C. to the sodium ethoxide solution (30 min). The reaction was warmed to room temperature and stirred for additional time (2.0 hr). The solution was quenched with saturated ammonium chloride solution (300 mL) and the aqueous solution was extracted with EtOAc (150 mL twice). The organic layer was then washed with brine (100 mL), and dried with anhydrous sodium sulfate. The solvent was removed to afford (1.55 g, 25% yield) a white crude solid intermediate as 2-azido-3-(2,3-dichloro-phenyl)-acrylic acid ethyl ester. The crude intermediate was diluted in 30 mL of xylenes and refluxed for 2 hr. The reaction mixture was cooled to room temperature and 25 mL of hexanes were added to produce a white precipitate. The solid was filtered and dried to afford the product 4,5-dichloro-1H-indole-2-carboxylic acid ethyl ester, (0.75 g, 54% yield) as a white solid. LRMS calcd for $C_{11}H_9Cl_2NO_2$ (m/e) 257, observed 256 (M–H).

4-Methyl-1H-indole-2-carboxylic acid ethyl ester

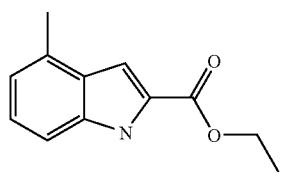

With a method similar to that used for the preparation of 4,5-dichloro-1H-indole-2-carboxylic acid ethyl ester, 4-methyl-1H-indole-2-carboxylic acid ethyl ester was prepared from the intermediate 2-azido-3-(2-methyl-phenyl)-acrylic acid ethyl ester. LCMS for $C_{12}H_{13}NO_2$ calcd. (m/e) 203, observed 202 (M–H).

4-Trifluoromethyl-1H-indole-2-carboxylic acid ethyl ester

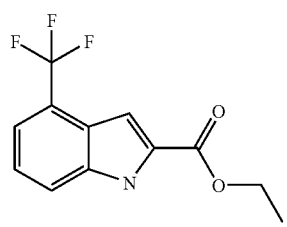

With a method similar to that used for the preparation of 4,5-dichloro-1H-indole-2-carboxylic acid ethyl ester, 4-trifluoromethyl-1H-indole-2-carboxylic acid ethyl ester was prepared from the intermediate 2-azido-3-(2-trifluoromethyl-phenyl)-acrylic acid ethyl ester. LCMS for $C_{12}H_{10}F_3NO_2$ calcd. (m/e) 257, observed 256 (M–H).

4,5-Dichloro-1-ethyl-1H-indole-2-carboxylic acid

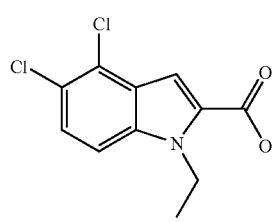

To a mixture of 4,5-dichloro-1H-indole-2-carboxylic acid ethyl ester (207 mg, 0.80 mmol) in DMF (2 mL) was added drop wise a suspension of NaH (41.2 mg, 60% dispersion in mineral oil, 1.03 mmol) in DMF (5 mL). The reaction mixture was stirred for 30 min, then ethyl iodide (156 mg, 1.0 mmol) diluted in 1 mL of DMF was added drop wise at room temperature and the mixture was stirred for an additional 1 hr. The reaction mixture was diluted with 100 mL of EtOAc and washed with saturated ammonium chloride (100 mL) and brine (50 mL). The organic layer was dried over anhydrous sodium sulfate and the solvent was removed. The residue was purified on a flash chromatography column with EtOAc/hexanes to afford 4,5-dichloro-1-ethyl-1H-indole-2-carboxylic acid ethyl ester (160 mg, 70% yield). The 4,5-dichloro-1-ethyl-1H-indole-2-carboxylic acid ethyl ester (160 mg, 0.56 mmol) was diluted in 10 mL of methanol and 4 mL of 1N NaOH and placed in a sealed tube. The reaction mixture was heated under microwave condition at 120° C. for 25 min. The reaction mixture was diluted with 150 mL of EtOAc and washed with 100 mL of 1N HCl, brine (50 L) and dried. The solvent was removed to afford the product 4,5-dichloro-1-ethyl-1H-indole-2-carboxylic acid (120 mg, 84% yield) as a white solid. LCMS for $C_{11}H_9Cl_2NO_2$ calcd. (m/e) 257, observed 256 (M–H).

5-Chloro-1-ethyl-1H-indole-2-carboxylic acid

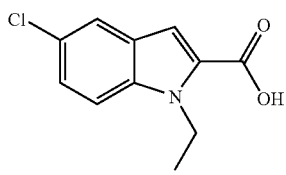

With a method similar to that used for the preparation of 4,5-dichloro-1-ethyl-1H-indole-2-carboxylic acid, 5-chloro-1-ethyl-1H-indole-2-carboxylic acid was prepared from 5-chloro-1H-indole-2-carboxylic acid ethyl ester. LRMS for $C_{11}H_{10}ClNO_2$ calcd. (m/e) 223, observed 222 (M–H).

1-Ethyl-4-methyl-1H-indole-2-carboxylic acid

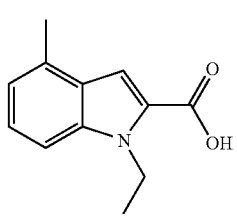

With a method similar to that used for the preparation of 4,5-dichloro-1-ethyl-1H-indole-2-carboxylic acid, 1-ethyl-4-methyl-1H-indole-2-carboxylic acid was prepared from 4-methyl-1H-indole-2-carboxylic acid ethyl ester. LCMS for $C_{12}H_{13}NO_2$ calcd. (m/e) 203, observed 204 (M+H).

1-Ethyl-4-trifluoromethyl-1H-indole-2-carboxylic acid

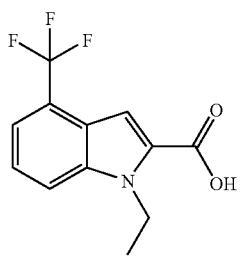

With a method similar to that used for the preparation of 4,5-dichloro-1-ethyl-1H-indole-2-carboxylic acid, 1-ethyl-4-trifluoromethyl-1H-indole-2-carboxylic acid was prepared from 4-trifluoromethyl-1H-indole-2-carboxylic acid ethyl ester. LCMS for $C_{12}H_{10}F_3NO_2$ calcd. (m/e) 257, observed 256 (M−H).

1-Ethyl-4-methoxy-1H-indole-2-carboxylic acid

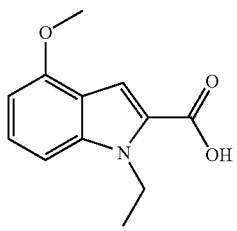

With a method similar to that used for the preparation of 4,5-dichloro-1-ethyl-1H-indole-2-carboxylic acid, 1-ethyl-4-methoxy-1H-indole-2-carboxylic acid was prepared from 4-methoxy-1H-indole-2-carboxylic acid ethyl ester. LCMS for $C_{12}H_{13}NO_3$ calcd. (m/e) 219, observed 220 (M+H).

1-Ethyl-4-5-dimethoxy-1H-indole-2-carboxylic acid

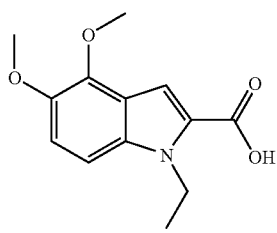

With a method similar to that used for the preparation of 4,5-dichloro-1-ethyl-1H-indole-2-carboxylic acid, 1-ethyl-4-5-dimethoxy-1H-indole-2-carboxylic acid was prepared from 4,5-dimethoxy-1H-indole-2-carboxylic acid ethyl ester. LCMS for $C_{13}H_{15}NO_4$ calcd. (m/e) 249, observed 250 (M+H).

1-Ethyl-5-methoxy-1H-indole-2-carboxylic acid

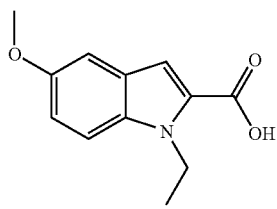

With a method similar to that used for the preparation of 4,5-dichloro-1-ethyl-1H-indole-2-carboxylic acid, 1-ethyl-5-methoxy-1H-indole-2-carboxylic acid was prepared from 5-methoxy-1H-indole-2-carboxylic acid ethyl ester. LCMS for $C_{12}H_{13}NO_3$ calcd. (m/e) 219, observed 220 (M+H).

5-Benzyloxy-1-ethyl-1,1-indole-2-carboxylic acid

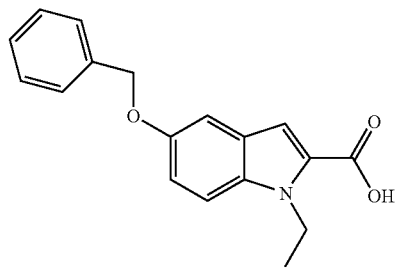

With a method similar to that used for the preparation of 4,5-dichloro-1-ethyl-1H-indole-2-carboxylic acid, 5-benzyloxy-1-ethyl-1H-indole-2-carboxylic acid was prepared from 5-benzyloxy-1H-indole-2-carboxylic acid ethyl ester. LCMS for $C_{18}H_{17}NO_3$ calcd. (m/e) 295, observed 296 (M+H).

1-Ethyl-5-trifluoromethoxy-1H-indole-2-carboxylic acid

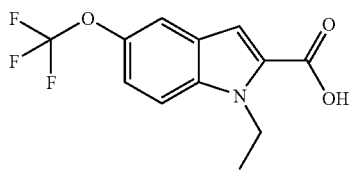

With a method similar to that used for the preparation of 4,5-dichloro-1-ethyl-1H-indole-2-carboxylic acid, 1-ethyl-5-trifluoromethoxy-1H-indole-2-carboxylic acid was prepared from 5-trifluoromethoxy-1H-indole-2-carboxylic acid ethyl ester. LCMS for $C_{12}H_{10}F_3NO_3$ calcd. (m/e) 273, observed 274 (M+H).

1-Ethyl-5,6-dimethoxy-1H-indole-2-carboxylic acid

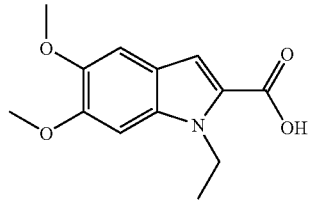

With a method similar to that used for the preparation of 4,5-dichloro-1-ethyl-1H-indole-2-carboxylic acid, 1-ethyl-5,6-dimethoxy-1H-indole-2-carboxylic acid was prepared from 5,6-dimethoxy-1H-indole-2-carboxylic acid ethyl ester. LCMS for $C_{13}H_{15}NO_4$ calcd. (m/e) 249, observed 250 (M+H).

1-Propyl-1H-1-indole-2-carboxylic acid

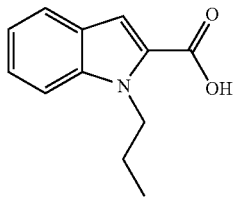

With a method similar to that used for the preparation of 4,5-dichloro-1-ethyl-1H-indole-2-carboxylic acid, 1-propyl-1H-indole-2-carboxylic acid was prepared from 1H-indole-2-carboxylic acid ethyl ester and 1-iodopropane. LCMS for $C_{12}H_{13}NO_2$ calcd. (m/e) 203, observed 204 (M+H).

1-Ethyl-4,6-dimethoxy-1,1-indole-2-carboxylic acid

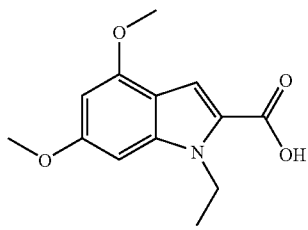

With a method similar to that used for the preparation of 4,5-dichloro-1H-indole-2-carboxylic acid, 1-ethyl-4,6-dimethoxy-1H-indole-2-carboxylic acid was prepared from 4,6-dimethoxy-1H-indole-2-carboxylic acid ethyl ester. LCMS for $C_{13}H_{15}NO_4$ calcd. (m/e) 249, observed 250 (M+H).

1-Ethyl-4-hydroxy-1H-indole-2-carboxylic acid ethyl ester

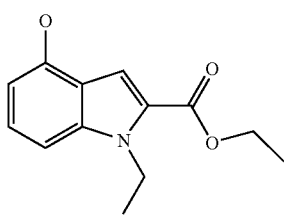

A mixture of 4-benzyloxy-1H-indole-2-carboxylic acid ethyl ester (1.0 g, 3.40 mmol) in DMF (2 mL) was added drop wise to a suspension of NaH (100 mg, 4.0 mmol) in DMF (5 mL). The reaction mixture was stirred for 30 min. Ethyl iodide (624 mg, 4.0 mmol) diluted in 1 mL of DMF was added drop wise at room temperature and the mixture was stirred for an additional 1 hr. The reaction mixture was diluted with 100 mL of EtOAc and washed with 100 mL of saturated ammonium chloride, brine (50 mL), dried over anhydrous sodium sulfate and the solvent was removed to afford crude 4-benzyloxy-1-ethyl-1H-indole-2-carboxylic acid ethyl ester (1.15 g). This material was diluted in 30 mL of ethanol and 100 mg of 10% Pd/C was added. The mixture was placed on a Parr shaker for hydrogenation at 50 psi for 3 hr. The mixture was filtered and the solvent was removed to afford 1-ethyl-4-hydroxy-1H-indole-2-carboxylic acid ethyl ester (0.730 g, 92% yield) as a white solid. LCMS for $C_{13}H_{15}NO_3$ calcd. (m/e) 233, observed 234 (M+H).

4-Ethoxy-1-ethyl-1H-indole-2-carboxylic acid

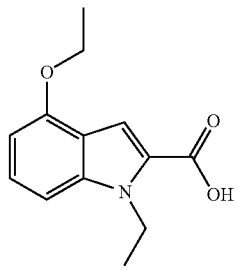

A mixture of 1-ethyl-4-hydroxy-1H-indole-2-carboxylic acid ethyl ester (100 mg, 0.43 mmol) and NaH (13 mg, 0.52 mmol) was stirred in DMF (3 mL) for 10 min. Ethyl iodide (80 mg, 0.52 mmol) diluted in 1 mL of DMF was added and placed in a sealed tube. The reaction mixture was heated to 120° C. via microwave for a period of 15 min. The reaction mixture was taken up in 100 mL of EtOAc and washed with 100 mL of 0.1N hydrochloric acid, brine (50 mL), and dried over anhydrous sodium sulfate. The solvent was removed to produce 4-ethoxy-1-ethyl-1H-indole-2-carboxylic acid ethyl ester (112 mg, 100% yield) as brown oil. This material was diluted in 2 mL of methanol and 2 mL of 1N NaOH and placed in a sealed tube. The reaction mixture was heated to 120° C. via microwave for 15 min. The reaction mixture was diluted in 100 mL of EtOAc and washed with 50 mL of 1N HCl, 50 mL of brine, dried over anhydrous sodium sulfate. The solvent was removed to afford 4-ethoxy-1-ethyl-1H-indole-2-carboxylic acid (100 mg, 100% yield) as a white solid. LCMS for $C_{13}H_{15}NO_3$ calcd. (m/e) 233, observed 234 (M+H).

1-Ethyl-4-isobutoxy-1H-indole-2-carboxylic acid

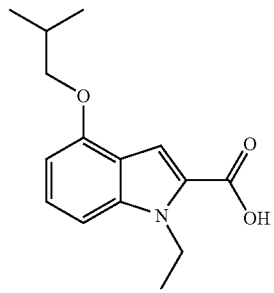

With a method similar to that used for the preparation of 4-ethoxy-1-ethyl-1H-indole-2-carboxylic acid, 1-ethyl-4-isobutoxy-1H-indole-2-carboxylic acid was prepared from 1-ethyl-4-hydroxy-1H-indole-2-carboxylic acid ethyl ester and 1-bromo-2-methyl-propane. LCMS for $C_{15}H_{19}NO_3$ calcd. (m/e) 261, observed 262 (M+H).

1-Ethyl-4-propoxy-1H-indole-2-carboxylic acid

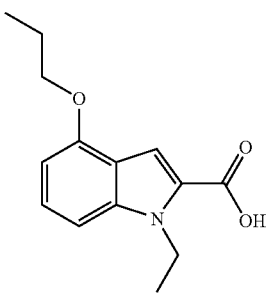

With a method similar to that used for the preparation of 4-ethoxy-1-ethyl-1H-indole-2-carboxylic acid, 1-ethyl-4-propoxy-1H-indole-2-carboxylic acid was prepared from 1-ethyl-4-hydroxy-1H-indole-2-carboxylic acid ethyl ester and 1-iodopropane. LCMS for $C_{14}H_{17}NO_3$ calcd. (m/e) 247, observed 248 (M+H).

4-{5-[(4-Chloro-benzo[b]thiophene-2-carbonyl)-amino]-pyridin-2-yl}-piperazine-1-carboxylic acid tert-butyl ester

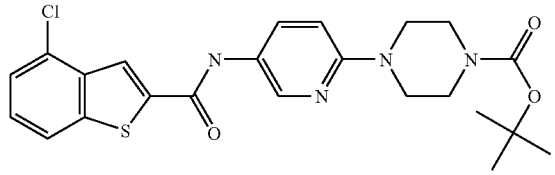

A mixture of 4-chloro-benzo[b]thiophene-2-carboxylic acid (98 mg, 0.462 mmol), $CH_2Cl_2$ (5 mL), and a catalytic amount of DMF was stirred under Ar, and oxalyl chloride (2M in dichloromethane, 600 μL, 1.20 mmol) was dripped into the mixture over 5 min. The mixture was stirred at room temperature and after 1.0 hr the reaction was concentrated to dryness. Benzene was added and the solution was evaporated to dryness again. The white-yellow solid was re-dissolved in 5 mL of $CH_2Cl_2$ and dripped, under Ar, into a solution of 4-(5-amino-pyridin-2-yl)-piperazine-1-carboxylic acid tert-butyl ester (134 mg, 0.462 mmol), and triethylamine (102 μL, 1.0 mmol) in 5 mL of dichloromethane. The reaction was stirred at room temperature for 0.5 hr and then concentrated and the residue was taken up in 50 mL of EtOAc and washed with 50 mL of saturated ammonium chloride, brine and dried over anhydrous sodium sulfate. The EtOAc solvent was removed and the product was triturated with diethyl ether and hexanes (1:1 ratio), followed by filtration, to afford the product, 4-{5-[(4-chloro-benzo[b]thiophene-2-carbonyl)-amino]-pyridin-2-yl}-piperazine-1-carboxylic acid tert-butyl ester, as a pale green solid (80 mg, 38% yield). LCMS for $C_{23}H_{25}ClN_4O_3S$ calcd. (m/e) 472, observed 471 (M−H).

4-Chloro-benzo[b]thiophene-2-carboxylic acid (6-piperazin-1-yl-pyridin-3-yl)amide

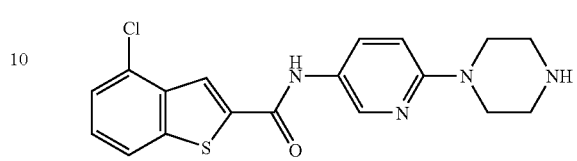

A mixture of 4-{5-[(4-chloro-benzo[b]thiophene-2-carbonyl)-amino]-pyridin-2-yl}-piperazine-1-carboxylic acid tert-butyl ester (75 mg, 0.16 mmol) in 15 mL of dichloromethane and 5 mL of TFA was stirred at room temperature for 2 hr. The reaction mixture was taken up in 100 mL of EtOAc and washed with 100 mL of 1N NaOH, brine and dried over anhydrous sodium sulfate. The solvent was removed and the residue was triturated with diethyl ether and hexanes (1:1 ratio), followed by filtration, to afford the product 4-chloro-benzo[b]thiophene-2-carboxylic acid (6-piperazin-1-yl-pyridin-3-yl)-amide, (50 mg, 85% yield) as an off white solid. LCMS for $C_{18}H_{17}ClN_4OS$ calcd. (m/e) 372, observed 373 (M+H).

5-Bromo-benzo[b]thiophene-2-carboxylic acid (6-piperazin-1-yl-pyridin-3-yl)-amide

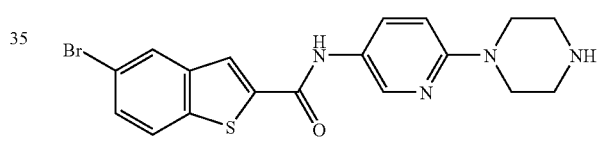

With a method similar to that used for the preparation of 4-chloro-benzo[b]thiophene-2-carboxylic acid (6-piperazin-1-yl-pyridin-3-yl)-amide, 5-bromo-benzo[b]thiophene-2-carboxylic acid (6-piperazin-1-yl-pyridin-3-yl)-amide was prepared from 5-bromo-benzo[b]thiophene-2-carboxylic acid and 4-(5-amino-pyridin-2-yl)-piperazine-1-carboxylic acid tert-butyl ester. LCMS for $C_{18}H_{17}BrN_4OS$ calcd. (m/e) 416, observed 417 (M+H).

4-{4-[(4,5-Dichloro-1-ethyl-1H-indole-2-carbonyl)-amino]-phenyl}-piperazine-1-carboxylic acid tert-butyl ester

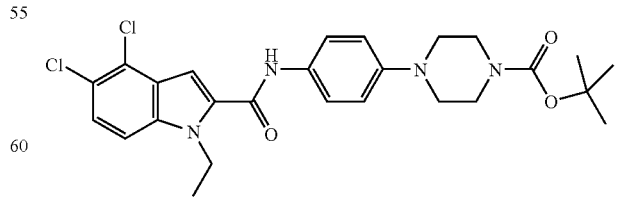

A mixture of 4,5-dichloro-1-ethyl-1H-indole-2-carboxylic acid (440 mg, 1.71 mmol), $CH_2Cl_2$ (10 mL), and a catalytic amount of DMF was stirred under Ar, and oxalyl chloride (2M in methylene chloride, 2.0 mL, 4.0 mmol) was added into the mixture over 5 min. The mixture was stirred at room temperature for 1.0 hr and the reaction was concentrated to dryness. Benzene was added and the solution was evaporated to dryness again. The white-yellow solid was re-dissolved in 5 mL of methylene chloride and dripped, under Ar, into a solution of 4-(4-amino-phenyl)-piperazine-1-carboxylic acid tert-butyl ester (475 mg, 1.71 mmol), and triethylamine (204 mg, 2.0 mmol) in 5 mL of methylene chloride. The mixture was first stirred at room temperature for 0.5 hr then concentrated and the residue was taken up in 50 mL of ethyl acetate and washed with 50 mL of saturated ammonium chloride, brine and dried with anhydrous sodium sulfate. The solvent was removed and the crude product was purified by flash chromatography (hexanes/EtOAc), to afford the desired 4-{4-[(4,5-dichloro-1-ethyl-1H-indole-2-carbonyl)-amino]-phenyl}-piperazine-1-carboxylic acid tert-butyl ester, as an off white solid (750 mg, 85% yield). LCMS for $C_{26}H_{30}Cl_2N_4O_3$ calcd. (m/e) 516, observed 517 (M+H).

4,5-Dichloro-1-ethyl-1H-indole-2-carboxylic acid (4-piperazin-1-yl-phenyl)-amide hydrochloride

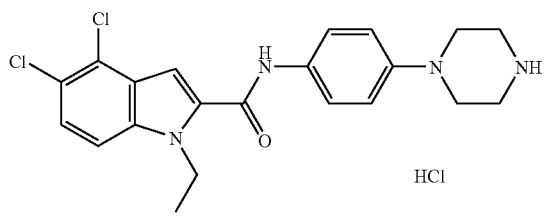

A mixture of 4-{4-[(4,5-dichloro-1-ethyl-1H-indole-2-carbonyl)-amino]-phenyl}-piperazine-1-carboxylic acid tert-butyl ester (750 mg, 1.45 mmol) in 15 mL of methylene chloride and 2 mL of 4M hydrogen chloride in dioxane was stirred at room temperature for 24 hr. The solvent was removed to afford 4,5-dichloro-1-ethyl-1H-indole-2-carboxylic acid (4-piperazin-1-yl-phenyl)-amide hydrochloride salt (700 mg, 99% yield) as an off white solid. LCMS for $C_{21}H_{22}Cl_2N_4O$ calcd. (m/e) 416, observed 417 (M+H).

1-Ethyl-4-methoxy-1H-indole-2-carboxylic acid (6-piperazin-1-yl-pyridin-3-yl)-amide

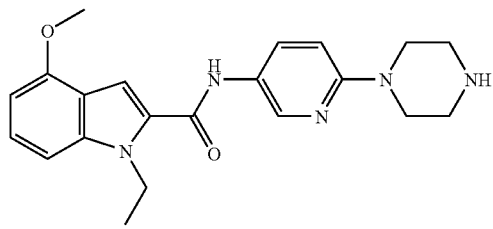

With a method similar to that used for the preparation of 4-chloro-benzo[b]thiophene-2-carboxylic acid (6-piperazin-1-yl-pyridin-3-yl)-amide, 1-ethyl-4-methoxy-1H-indole-2-carboxylic acid (6-piperazin-1-yl-pyridin-3-yl)-amide was prepared from 1-ethyl-4-methoxy-1H-indole-2-carboxylic acid and 4-(5-amino-pyridin-2-yl)-piperazine-1-carboxylic acid tert-butyl ester. LCMS for $C_{21}H_{25}N_5O_2$ calcd. (m/e) 379, observed 380 (M+H).

1-Ethyl-4-trifluoromethyl-1H-indole-2-carboxylic acid (6-piperazin-1-yl-pyridin-3-yl)-amide

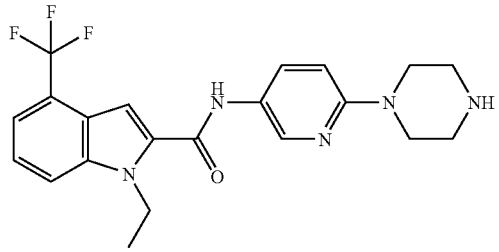

With a method similar to that used for the preparation of 4-chloro-benzo[b]thiophene-2-carboxylic acid (6-piperazin-1-yl-pyridin-3-yl)-amide, 1-ethyl-4-trifluoromethyl-1H-indole-2-carboxylic acid (6-piperazin-1-yl-pyridin-3-yl)-amide was prepared from 1-ethyl-4-trifluoromethyl-1H-indole-2-carboxylic acid and 4-(5-amino-pyridin-2-yl)-piperazine-1-carboxylic acid tert-butyl ester. LCMS for $C_{21}H_{22}F_3N_5O$ calcd. (m/e) 417, observed 418 (M+H).

1-Ethyl-4,5-dimethoxy-1H-indole-2-carboxylic acid (6-piperazin-1-yl-pyridin-3-yl)-amide

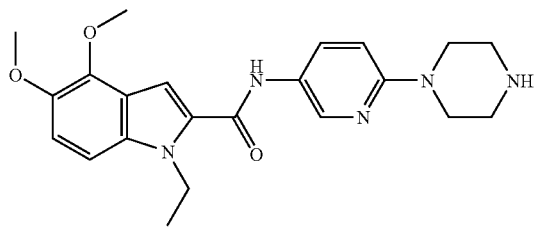

With a method similar to that used for the preparation of 4-chloro-benzo[b]thiophene-2-carboxylic acid (6-piperazin-1-yl-pyridin-3-yl)-amide, 1-ethyl-4,5-dimethoxy-1H-indole-2-carboxylic acid (6-piperazin-1-yl-pyridin-3-yl)-amide was prepared from 1-ethyl-4,5-dimethoxy-1H-indole-2-carboxylic acid and 4-(5-amino-pyridin-2-yl)-piperazine-1-carboxylic acid tert-butyl ester. LCMS for $C_{22}H_{27}N_5O_3$ calcd. (m/e) 409, observed 410 (M+H).

1-Ethyl-4,6-dimethoxy-1H-indole-2-carboxylic acid (6-piperazin-1-yl-pyridin-3-yl)-amide

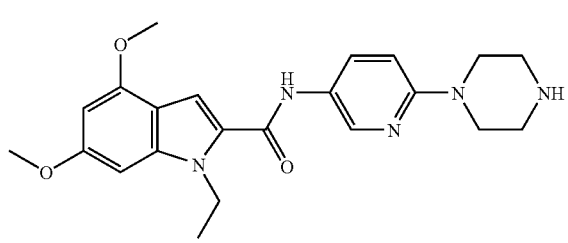

With a method similar to that used for the preparation of 4-chloro-benzo[b]thiophene-2-carboxylic acid (6-piperazin-1-yl-pyridin-3-yl)-amide, 1-ethyl-4,6-dimethoxy-1H-indole-2-carboxylic acid (6-piperazin-1-yl-pyridin-3-yl)-amide was prepared from 1-ethyl-4,6-dimethoxy-1H-indole-2-carboxylic acid and 4-(5-amino-pyridin-2-yl)-piperazine-1-carboxylic acid tert-butyl ester. LCMS for $C_{22}H_{27}N_5O_3$ calcd. (m/e) 409, observed 410 (M+H).

4-Ethoxy-1-ethyl-1,1-indole-2-carboxylic acid (6-piperazin-1-yl-pyridin-3-yl)-amide

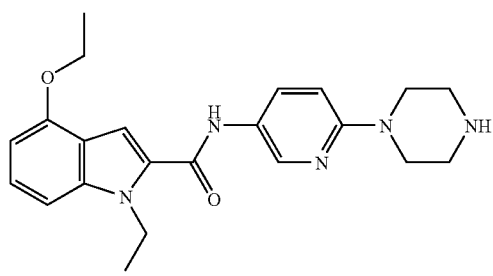

With a method similar to that used for the preparation of 4-chloro-benzo[b]thiophene-2-carboxylic acid (6-piperazin-1-yl-pyridin-3-yl)-amide, 4-ethoxy-1-ethyl-1H-indole-2-carboxylic acid (6-piperazin-1-yl-pyridin-3-yl)-amide was prepared from 4-ethoxy-1-ethyl-1H-indole-2-carboxylic acid and 4-(5-amino-pyridin-2-yl)-piperazine-1-carboxylic acid tert-butyl ester. LCMS for $C_{22}H_{27}N_5O_2$ calcd. (m/e) 393, observed 394 (M+H).

1-Ethyl-4-propoxy-1H-indole-2-carboxylic acid (6-piperazin-1-yl-pyridin-3-yl)-amide

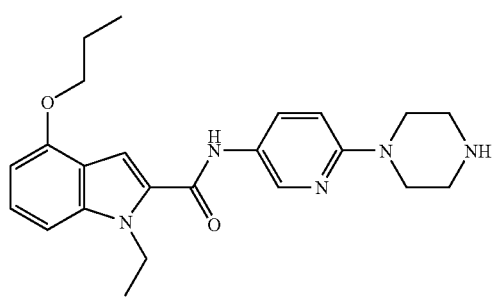

With a method similar to that used for the preparation of 4-chloro-benzo[b]thiophene-2-carboxylic acid (6-piperazin-1-yl-pyridin-3-yl)-amide, 1-ethyl-4-propoxy-1H-indole-2-carboxylic acid (6-piperazin-1-yl-pyridin-3-yl)-amide was prepared from 1-ethyl-4-propoxy-1H-indole-2-carboxylic acid and 4-(5-amino-pyridin-2-yl)-piperazine-1-carboxylic acid tert-butyl ester. LCMS for $C_{23}H_{29}N_5O_2$ calcd. (m/e) 407, observed 408 (M+H).

1-Ethyl-4-isobutoxy-1H-indole-2-carboxylic acid (6-piperazin-1-yl-pyridin-3-yl)-amide

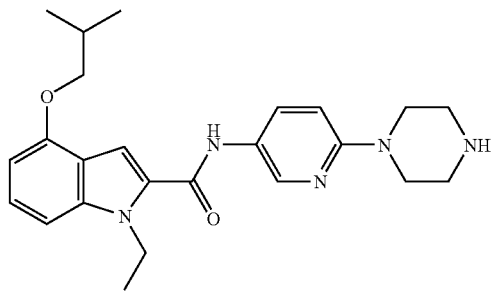

With a method similar to that used for the preparation of 4-chloro-benzo[b]thiophene-2-carboxylic acid (6-piperazin-1-yl-pyridin-3-yl)-amide, 1-ethyl-4-isobutoxy-1H-indole-2-carboxylic acid (6-piperazin-1-yl-pyridin-3-yl)-amide was prepared from 1-ethyl-4-isobutoxy-1H-indole-2-carboxylic acid and 4-(5-amino-pyridin-2-yl)-piperazine-1-carboxylic acid tert-butyl ester. LCMS for $C_{24}H_{31}N_5O_2$ calcd. (m/e) 421, observed 422 (M+H).

5-Chloro-1-ethyl-1H-indole-2-carboxylic acid (6-piperazin-1-yl-pyridin-3-yl)-amide

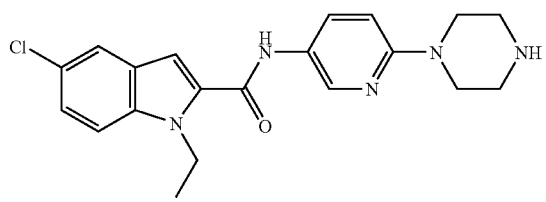

With a method similar to that used for the preparation of 4-chloro-benzo[b]thiophene-2-carboxylic acid (6-piperazin-1-yl-pyridin-3-yl)-amide, 5-chloro-1-ethyl-1,4-indole-2-carboxylic acid (6-piperazin-1-yl-pyridin-3-yl)-amide was prepared from 5-chloro-1-ethyl-1H-indole-2-carboxylic acid and 4-(5-amino-pyridin-2-yl)piperazine-1-carboxylic acid tert-butyl ester. LCMS for $C_{20}H_{22}Cl\,N_5O$ calcd. (m/e) 383, observed 384 (M+H).

4,5-Dichloro-1-ethyl-1H-indole-2-carboxylic acid (6-piperazin-1-yl-pyridin-3-yl)-amide

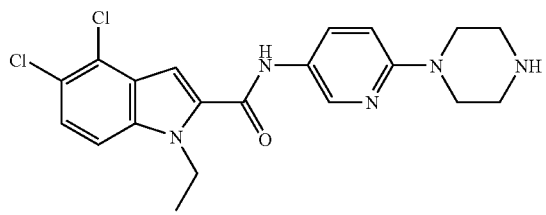

With a method similar to that used for the preparation of 4-chloro-benzo[b]thiophene-2-carboxylic acid (6-piperazin-1-yl-pyridin-3-yl)-amide, 4,5-dichloro-1-ethyl-1H-indole-2-carboxylic acid (6-piperazin-1-yl-pyridin-3-yl)-amide was prepared from 4,5-dichloro-1-ethyl-1H-indole-2-carboxylic acid and 4-(5-amino-pyridin-2-yl)piperazine-1-carboxylic acid tert-butyl ester. LCMS for $C_{20}H_{21}Cl_2N_5O$ calcd. (m/e) 417, observed 418 (M+H).

4-Chloro-benzo[b]thiophene-2-carboxylic acid (4-piperidin-4-yl-phenyl)-amide

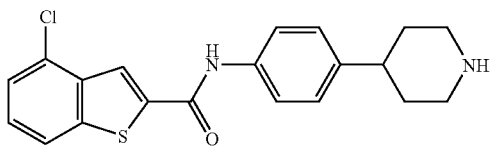

With a method similar to that used for the preparation of 4-chloro-benzo[b]thiophene-2-carboxylic acid (6-piperazin-1-yl-pyridin-3-yl)-amide, 4-chloro-benzo[b]thiophene-2-carboxylic acid (4-piperidin-4-yl-phenyl)-amide was prepared from 4-chloro-benzo[b]thiophene-2-carboxylic acid and 4-(4-amino-phenyl)-piperidine-1-carboxylic acid tert-butyl ester. LCMS for $C_{20}H_{19}ClN_2OS$ calcd. (m/e) 370, observed 371 (M+H).

4-Chloro-benzo[b]thiophene-2-carboxylic acid (4-piperazin-1-yl-phenyl)-amide

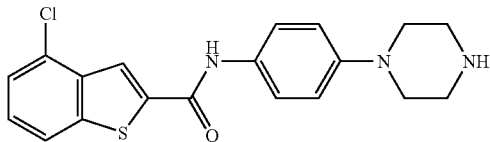

With a method similar to that used for the preparation of 4-chloro-benzo[b]thiophene-2-carboxylic acid (6-piperazin-1-yl-pyridin-3-yl)-amide, 4-chloro-benzo[b]thiophene-2-carboxylic acid (4-piperazin-1-yl-phenyl)-amide was prepared from 4-chloro-benzo[b]thiophene-2-carboxylic acid and 4-(4-amino-phenyl)-piperazine-1-carboxylic acid tert-butyl ester. LCMS for $C_{19}H_{18}ClN_3OS$ calcd. (m/e) 371, observed 372 (M+H).

(S)-3-(5-Amino-pyridin-2-ylamino)-pyrrolidine-1-carboxylic acid ethyl ester

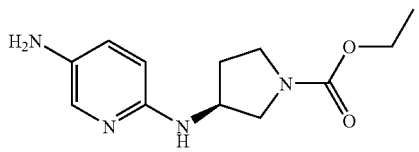

To a solution of (S)-3-aminopyrrolidine-1-carboxylic acid-tert-butyl ester (5 g, 26.88 mmol) and 2-chloro-5-nitropyridine (4.26 g, 26.88 mmol) in THF (100 mL) was added potassium carbonate (7.42 g, 53.76 mmol). The mixture was refluxed for 72 hrs. The mixture was filtered and the filtrate was concentrated. The residue was extracted with ethyl acetate and water. The organic layer was dried over sodium sulfate and solvents were evaporated. The oily residue was diluted with ether (50 mL) to give a clear solution which was kept at room temperature for 48 hrs. The crystalline material was filtered to give (S)-3-(5-nitro-pyridin-2-ylamino)-pyrrolidine-1-carboxylic acid test-butyl ester (6.66 g, 80.5% yield). LCMS for $C_{14}H_{20}N_4O_4$ calcd (m/e) 308, obsd 307 (M−H).

The above nitro compound (6.16 g, 20.0 mmol) was suspended in dichloromethane (200 mL) and hydrogen chloride in dioxane (4M, 25 mL) was added. The mixture was stirred overnight and solvents were evaporated to give (S)-5-nitro-pyridine-2-yl-pyrrolidine-3-yl-amine hydrochloride as an off white solid (5.92 g).

The above hydrochloride salt (2.81 g, 10 mmol) was suspended in dichloromethane (100 mL) and triethylamine (4.04 g, 40 mmol) was added. The mixture was stirred and a solution of ethyl chloroformate (1.12 g, 10.3 mmol) in dichloromethane (20 mL) was added over 10 minutes. The mixture was stirred at room temperature for 1 hr and solvents were evaporated. The mixture was extracted with ethyl acetate and saturated ammonium chloride solution. Organic layer was dried over sodium sulfate and solvents were evaporated to give (S)-3-(5-nitropyridine-2-ylamino)-pyrrolidine-1-carboxylic acid ethyl ester as a pale yellow solid (2.59 g, 92% yield). LCMS for $C_{12}H_{16}N_4O_4$ calcd (m/e) 280, obsd 279 (M−H).

The above (S)-3-(5-nitropyridine-2-ylamino)-pyrrolidine-1-carboxylic acid ethyl ester (2.59 g, 9.25 mmol) was suspended in ethanol (50 mL) and THF (10 mL) was added. The mixture was gently heated to give a clear solution and 10% palladium on carbon (250 mg) was added. The mixture was hydrogenated at 45 psi for 4 hrs and then filtered. The filtrate was concentrated to give a purple solid as (S)-3-(5-amino-pyridin-2-ylamino)-pyrrolidine-1-carboxylic acid ethyl ester (2.3 g, 100% yield). LCMS for $C_{12}H_{18}N_4O_2$ calcd (m/e) 250, obsd 251 (M+H).

(S)-3-(5-Amino-pyridin-2-ylamino)-pyrrolidine-1-carboxylic acid tert-butylamide

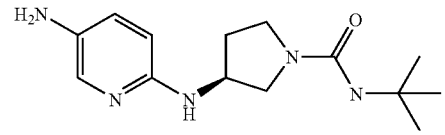

To a suspension of (S)-5-nitropyridine-2-yl-pyrrolidine-3-yl-amine hydrochloride (870 mg, 3.09 mmol) in dichloromethane (100 mL) was added triethylamine (1.07 g, 10.59 mmol) and N-tert-butylisocyanate (315 mg, 3.09 mmol). The mixture was stirred at room temperature for 1 hr and solvents were evaporated. The residue was extracted with ethyl acetate and concentrated ammonium chloride solution. The organic layer was washed with brine and dried over sodium sulfate. Solvents were evaporated and the residue was triturated with ether and petroleum ether to give a yellow solid as (S)-3-(5-nitro-pyridin-2-ylamino)-pyrrolidine-1-carboxylic acid tert-butylamide (0.75 g, 79%). LCMS for $C_{14}H_{21}N_5O_3$ calcd (m/e) 307, obsd 306 (M−H).

The above nitro compound (0.73 g) was suspended in methanol (100 mL) and 10% palladium on carbon was added. The mixture was hydrogenated at 45 psi for 4 hrs. The mixture was filtered and the filtrate was concentrated to give (S)-3-(5-amino-pyridin-2-ylamino)-pyrrolidine-1-carboxylic acid tert-butylamide (0.63 g) as a purple solid. LCMS for $C_{14}H_{23}N_5O$ calcd (m/e) 277, obsd 278 (M+H).

4-Ethoxy-1-ethyl-1H-indole-2-carboxylic acid [4-((S)-pyrrolidin-3-yloxy)-phenyl]amide hydrochloride

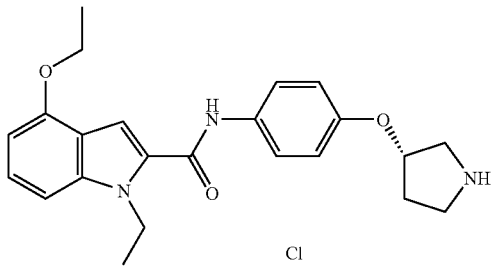

4-Fluoronitrobenzene (2.82 g, 20 mmol) was mixed with (S)-3-hydroxy-N-Boc-pyrrolidine (3.74 g, 20 mmol) in dry THF (100 mL). At 0° C., sodium hydride (1.69 g, 60% dispensed in mineral oil, 2.20 eq) was added. The mixture was stirred at 0° C. for 60 min and at room temperature overnight. Solvents were evaporated and the residue was extracted with ethyl acetate and 0.2N hydrochloric acid. The organic layer was washed with brine and dried over sodium sulfate. After the evaporation of solvents, the residue was purified through flash column chromatography using ethyl acetate and hexanes (5% to 60% ethyl acetate) to give a crystalline material as (S)-3-(4-nitro-phenyloxy)-pyrrolidine-1-carboxylic acid tert-butyl ester (4.33 g, 70.3% yield).

The above nitro compound was hydrogenated under conditions as described in previous intermediate to provide (S)-3-(4-amino-phenyloxy)-pyrrolidine-1-carboxylic acid tert-butyl ester. The amide formation of N-ethyl-4-ethoxy-indole-2-carboxylic acid with (S)-3-(4-amino-phenoxy)-pyrrolidine-1-carboxylic acid tert-butyl ester under the same conditions as described in earlier intermediates preparation provided (S)-3-{4-[(4-ethoxy-1-ethyl-1H-indole-2-carbonyl)-amino]-phenoxy}-pyrrolidine-1-carboxylic acid tert-butyl ester. LCMS for $C_{28}H_{35}N_3O_5$ calcd. (m/e) 493, observed 494 (M+H).

The above N-Boc compound (300 mg) was suspended in 100 mL of methanol and treated with concentrated hydrochloric acid (2 mL). The mixture was stirred overnight and then concentrated. The residue was dried in vacuum and the resulting material was triturated with ethyl acetate and ether. The white solid was filtered to give a hydrochloride salt of 4-ethoxy-1-ethyl-1H-indole-2-carboxylic acid [4-((S)-pyrrolidin-3-yloxy)-phenyl]-amide. LCMS for $C_{23}H_{27}N_3O_3$ calcd. (m/e) 393, observed 394 (M+H).

Part II: Preparation of Preferred Compounds of the Invention

Example 1

4-{5-[(4-Chloro-benzo[b]thiophene-2-carbonyl)-amino]-pyridin-2-yl}-piperazine-1-carboxylic acid tert-butyl ester

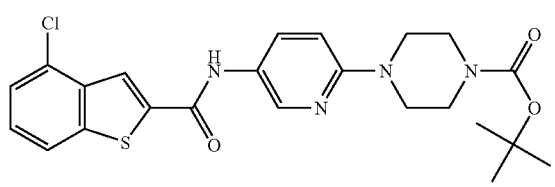

This compound was prepared from 4-chloro-benzo[b]thiophene-2-carboxylic acid and 4-(5-amino-pyridin-2-yl)-piperazine-1-carboxylic acid tort-butyl ester as described in the preparation of the intermediate section. LCMS for $C_{23}H_{25}ClN_4O_3S$ calcd. (m/e) 472, observed 471 (M–H).

Example 2

4-(4-{5-[(4-Chloro-benzo[b]thiophene-2-carbonyl)-amino]-pyridin-2-yl}-piperazin-1-yl)-2,2-dimethyl-4-oxo-butyric acid

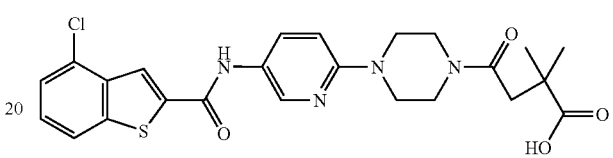

A mixture of 4-chloro-benzo[b]thiophene-2-carboxylic acid (6-piperazin-1-yl-pyridin-3-yl)-amide (50 mg, 0.13 mmol), $CH_2Cl_2$ (5 mL), and TEA (40 mg, 0.39 mmol) was stirred at room temperature. 2,2-Dimethylsuccinic anhydride (36 mg, 0.28 mmol) was added slowly. The reaction was stirred at room temperature for 0.5 hr then concentrated and the residue was taken up into 50 mL of EtOAc and washed with 50 mL of saturated ammonium chloride, brine and dried over anhydrous sodium sulfate. The solvent was removed and the product was triturated with diethyl ether and hexanes followed by filtration, to afford the product 4-(4-{5-[(4-chloro-benzo[b]thiophene-2-carbonyl)-amino]-pyridin-2-yl}-piperazin-1-yl)-2,2-dimethyl-4-oxo-butyric acid (58 mg, 89% yield). LCMS for $C_{24}H_{25}ClN_4O_4S$ calcd. (m/e) 500, observed 499 (M–H).

Example 3

4-{5-[(5-Bromo-benzo[b]thiophene-2-carbonyl)-amino]-pyridin-2-yl}-piperazine-1-carboxylic acid tert-butyl ester

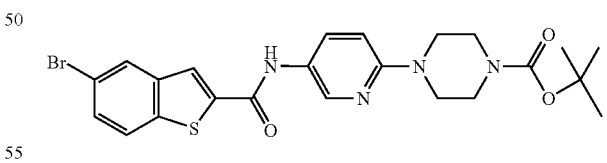

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(5-bromo-benzo[b]thiophene-2-carbonyl)-amino]-pyridin-2-yl}-piperazine-1-carboxylic acid tert-butyl ester was prepared from 5-bromo-benzo[b]thiophene-2-carboxylic acid and 4-(5-amino-pyridin-2-yl)-piperazine-1-carboxylic acid tert-butyl ester. LCMS for $C_{23}H_{25}BrN_4O_3S$ calcd. (m/e) 516, observed 517 (M+H).

Example 4

4-(4-{5-[(5-Bromo-benzo[b]thiophene-2-carbonyl)-amino]-pyridin-2-yl}-piperazin-1-yl)-2,2-dimethyl-4-oxo-butyric acid

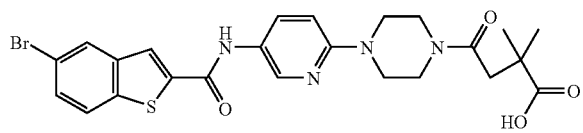

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{5-[(5-bromo-benzo[b]thiophene-2-carbonyl)-amino]-pyridin-2-yl}-piperazin-1-yl)-2,2-dimethyl-4-oxo-butyric acid was prepared from 5-bromo-benzo[b]thiophene-2-carboxylic acid (6-piperazin-1-yl-pyridin-3-yl)-amide and 2,2-dimethylsuccinic anhydride. LCMS for $C_{24}H_{25}BrN_4O_4S$ calcd. (m/e) 544, observed 543 (M–H).

Example 5

4-{5-[(4-Ethoxy-1-ethyl-1H-indole-2-carbonyl)-amino]-pyridin-2-yl}-piperazine-1-carboxylic acid tert-butyl ester

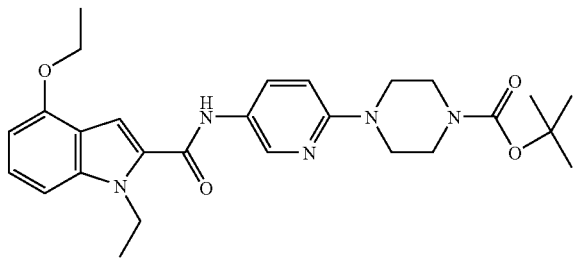

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(4-ethoxy-1-ethyl-1H-indole-2-carbonyl)-amino]-pyridin-2-yl}-piperazine-1-carboxylic acid tert-butyl ester was prepared from N-ethyl-4-ethoxy-indole-2-carboxylic acid and 4-(5-amino-pyridin-2-yl)-piperazine-1-carboxylic acid tert-butyl ester. LCMS for $C_{27}H_{35}N_5O_4$ calcd. (m/e) 493, observed 494 (M+H).

Example 6

4-(4-{5-[(4-Ethoxy-1-ethyl-1H-indole-2-carbonyl)-amino]-pyridin-2-yl}-piperazin-1-yl)-2,2-dimethyl-4-oxo-butyric acid

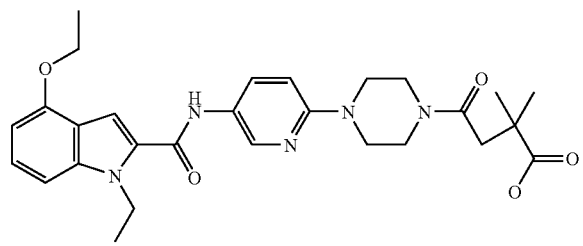

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{5-[(4-ethoxy-1-ethyl-1H-indole-2-carbonyl)-amino]-pyridin-2-yl}-piperazin-1-yl)-2,2-dimethyl-4-oxo-butyric acid was prepared from 4-ethoxy-1-ethyl-1H-indole-2-carboxylic acid (6-piperazin-1-yl-pyridin-3-yl)-amide and 2,2-dimethylsuccinic anhydride. LCMS for $C_{28}H_{35}N_5O_5$ calcd. (m/e) 521, observed 522 (M+H).

Example 7

4-(4-{4-[(4-Ethoxy-1-ethyl-1H-indole-2-carbonyl)-amino]-phenyl}-piperidin-1-yl)-2,2-dimethyl-4-oxo-butyric acid

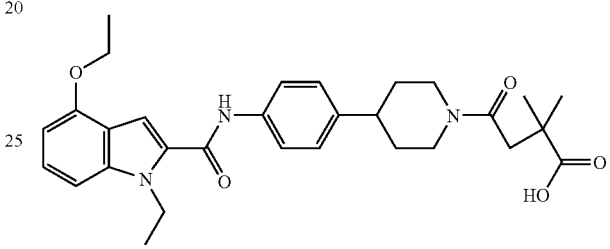

With a method similar to that used for the preparation of 4-(4-{5-[(4-chloro-benzothiophene-2-carbonyl)-amino]-pyridin-2-yl}-piperazin-1-yl)-2,2-dimethyl-4-oxo-butyric acid, 4-(4-{4-[(4-ethoxy-1-ethyl-1H-indole-2-carbonyl)-amino]-phenyl}-piperidin-1-yl)-2,2-dimethyl-4-oxo-butyric acid was prepared from 4-ethoxy-1-ethyl-1H-indole-2-carboxylic acid (4-piperidin-4-yl-phenyl)-amide and 2,2-dimethylsuccinic anhydride. LCMS for $C_{30}H_{37}N_3O_5$ calcd. (m/e) 519, observed 520 (M+H).

Example 8

4-(4-{4-[(1-Ethyl-4-methyl-4H-indole-2-carbonyl)-amino]-phenyl}-piperidin-1-yl)-2,2-dimethyl-4-oxo-butyric acid

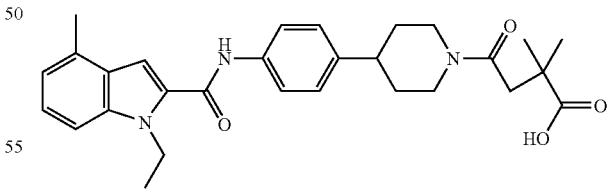

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{4-[(1-ethyl-4-methyl-1H-indole-2-carbonyl)-amino]-phenyl}-piperidin-1-yl)-2,2-dimethyl-4-oxo-butyric acid was prepared from 1-ethyl-4-methyl-1H-indole-2-carboxylic acid (4-piperidin-4-yl-phenyl)-amide and 2,2-dimethylsuccinic anhydride. LCMS for $C_{29}H_{35}N_3O_4$ calcd. (m/e) 489, observed 490 (M+H).

Example 9

4-(4-{4-[(4,5-Dichloro-ethyl-1H-indole-2-carbonyl)-amino]-phenyl}-piperidin-1-yl)-2,2-dimethyl-4-oxo-butyric acid

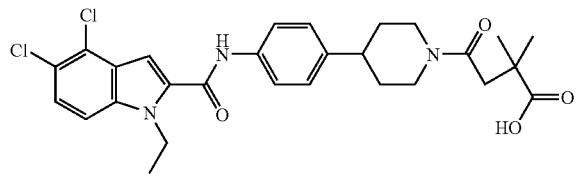

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{4-[(4,5-dichloro-1-ethyl-1H-indole-2-carbonyl)-amino]-phenyl}-piperidin-1-yl)-2,2-dimethyl-4-oxo-butyric acid was prepared from 4,5-dichloro-1-ethyl-1H-indole-2-carboxylic acid (4-piperidin-4-yl-phenyl)-amide and 2,2-dimethylsuccinic anhydride. LCMS for $C_{28}H_{31}Cl_2N_3O_4$ calcd. (m/e) 543, observed 544 (M+H).

Example 10

4-{5-[(1-Ethyl-4-propoxy-1,1-indole-2-carbonyl)-amino]-pyridin-2-yl}-piperazine-1-carboxylic acid tert-butyl ester

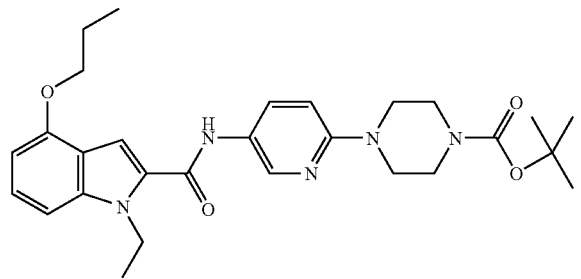

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(1-ethyl-4-propoxy-1H-indole-2-carbonyl)-amino]-pyridin-2-yl}-piperazine-1-carboxylic acid tert-butyl ester was prepared from N-ethyl-4-propoxy-indole-2-carboxylic acid and 4-(5-amino-pyridin-2-yl)-piperazine-1-carboxylic acid tert-butyl ester. LCMS for $C_{28}H_{37}N_5O_4$ calcd. (m/e) 507, observed 508 (M+H).

Example 11

4-(4-{5-[(1-Ethyl-4-propoxy-1H-indole-2-carbonyl)-amino]-pyridin-2-yl}-piperazin-1-yl)-2,2-dimethyl-4-oxo-butyric acid

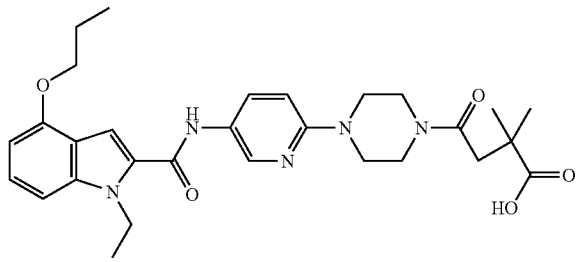

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{5-[(1-ethyl-4-propoxy-1H-indole-2-carbonyl)-amino]-pyridin-2-yl}-piperazin-1-yl)-2,2-dimethyl-4-oxo-butyric acid was prepared from 1-ethyl-4-propoxy-1H-indole-2-carboxylic acid (6-piperazin-1-yl-Pyridin-3-yl)-amide and 2,2-dimethylsuccinic anhydride. LCMS for $C_{29}H_{37}N_5O_5$ calcd. (m/e) 535, observed 536 (M+H).

Example 12

4-{5-[(1-Ethyl-4-isobutoxy-1H-indole-2-carbonyl)-amino]-pyridin-2-yl}-piperazine-1-carboxylic acid tert-butyl ester

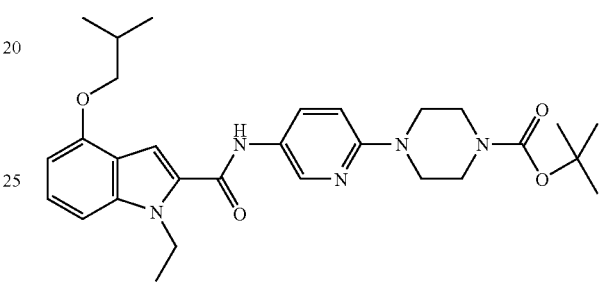

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(1-ethyl-4-isobutoxy-1H-indole-2-carbonyl)-amino]-pyridin-2-yl}-piperazine-1-carboxylic acid tert-butyl ester was prepared from N-ethyl-4-isobutoxy-indole-2-carboxylic acid and 4-(5-amino-pyridin-2-yl)-piperazine-1-carboxylic acid tert-butyl ester. LCMS for $C_{29}H_{39}N_5O_4$ calcd. (m/e) 521, observed 522 (M+H).

Example 13

4-(4-{5-[(1-Ethyl-4-isobutoxy-1H-indole-2-carbonyl)-amino]-pyridin-2-yl}-piperazin-1-yl)-2,2-dimethyl-4-oxo-butyric acid hydrochloric acid

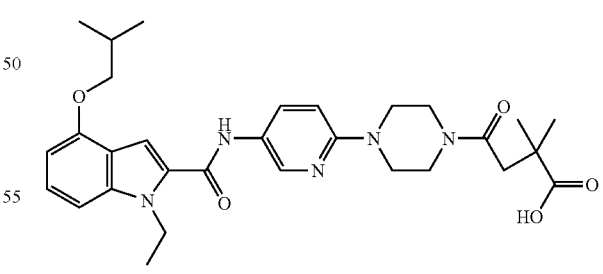

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{5-[(1-ethyl-4-isobutoxy-1,1-indole-2-carbonyl)-amino]-pyridin-2-yl}-piperazin-1-yl)-2,2-dimethyl-4-oxo-butyric acid was prepared from 1-ethyl-4-isobutoxy-1H-indole-2-carboxylic acid (6-piperazin-1-yl-pyridin-3-yl)- amide and 2,2-dimethylsuccinic anhydride. The desired product was dissolved in methylene chloride and treated with gaseous hydrogen chloride in ether. After the evaporation of solvents, a hydrochloride salt was obtained. LCMS for $C_{30}H_{39}N_5O_5$ calcd. (m/e) 549, observed 550 (M+H).

Example 14

4-{5-[(1-Ethyl-4-trifluoromethyl-1H-indole-2-carbonyl)-amino]-pyridin-2-yl}-piperazine-1-carboxylic acid tert-butyl ester

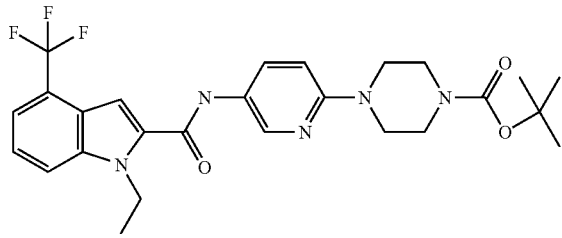

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(1-ethyl-4-trifluoromethyl-1H-indole-2-carbonyl)-amino]-pyridin-2-yl}-piperazine-1-carboxylic acid tert-butyl ester was prepared from N-ethyl-4-trifluoromethyl-indole-2-carboxylic acid and 4-(5-amino-pyridin-2-yl)-piperazine-1-carboxylic acid tert-butyl ester. LCMS for $C_{26}H_{30}F_3N_5O_3$ calcd. (m/e) 517, observed 518 (M+H).

Example 15

4-(4-{5-[(1-Ethyl-4-trifluoromethyl-1H-indole-2-carbonyl)-amino]-pyridin-2-yl}-piperazin-1-yl)-2,2-dimethyl-4-oxo-butyric acid

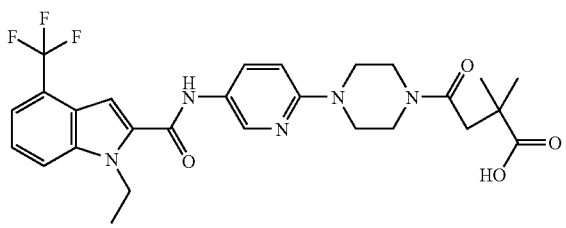

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{5-[(1-ethyl-4-trifluoromethyl-1H-indole-2-carbonyl)-amino]-pyridin-2-yl}-piperazin-1-yl)-2,2-dimethyl-4-oxo-butyric acid was prepared from 1-ethyl-4-trifluoromethyl-1H-indole-2-carboxylic acid (6-piperazin-1-yl-pyridin-3-yl)-amide and 2,2-dimethylsuccinic anhydride. LCMS for $C_{27}H_{30}F_3N_5O_4$ calcd. (m/e) 545, observed 546 (M+H).

Example 16

4-{5-[(1-Ethyl-4,6-dimethoxy-1H-indole-2-carbonyl)-amino]-pyridin-2-yl}-piperazine-1-carboxylic acid tert-butyl ester

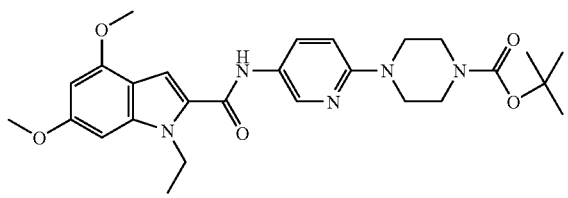

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(1-ethyl-4,6-dimethoxy-1H-indole-2-carbonyl)-amino]-pyridin-2-yl}-piperazine-1-carboxylic acid tert-butyl ester was prepared from N-ethyl-4,6-dimethoxy-indole-2-carboxylic acid and 4-(5-amino-pyridin-2-yl)-piperazine-1-carboxylic acid tert-butyl ester. LCMS for $C_{27}H_{35}N_5O_5$ calcd. (m/e) 509, observed 510 (M+H).

Example 17

4-(4-{5-[(1-Ethyl-4,6-dimethoxy-1H-indole-2-carbonyl)-amino]-pyridin-2-yl}-piperazin-1-yl)-2,2-dimethyl-4-oxo-butyric acid

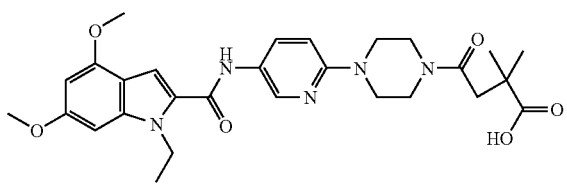

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{5-[(1-ethyl-4,6-dimethoxy-1H-indole-2-carbonyl)-amino]-pyridin-2-yl}-piperazin-1-yl)-2,2-dimethyl-4-oxo-butyric acid was prepared from 1-ethyl-4,6-dimethoxy-1H-indole-2-carboxylic acid (6-piperazin-1-yl-pyridin-3-yl)-amide and 2,2-dimethylsuccinic anhydride. LCMS for $C_{28}H_{35}N_5O_6$ calcd. (m/e) 537, observed 538 (M+H).

Example 18

4-{5-[(4,5-Dichloro-1-ethyl-1H-indole-2-carbonyl)-amino]-pyridin-2-yl}-piperazine-1-carboxylic acid tert-butyl ester

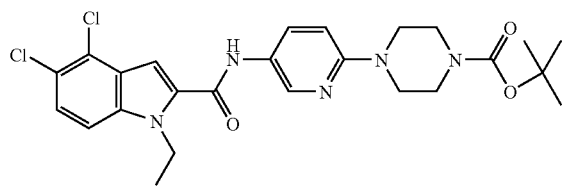

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(4,5-dichloro-1-ethyl-1H-indole-2-carbonyl)-amino]-pyridin-2-yl}-piperazine-1-carboxylic acid tert-butyl ester was prepared from N-ethyl-4,5-dichloro-indole-2-carboxylic acid and 4-(5-amino-pyridin-2-yl)-piperazine-1-carboxylic acid tert-butyl ester. LCMS for $C_{25}H_{29}Cl_2N_5O_3$ calcd. (m/e) 517, observed 518 (M+H).

Example 19

4-(4-{5-[(4,5-Dichloro-1-ethyl-1H-indole-2-carbonyl)-amino]-pyridin-2-yl}-piperazin-1-yl)-2,2-dimethyl-4-oxo-butyric acid

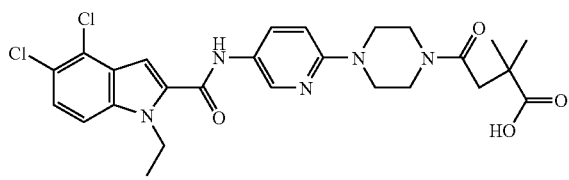

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{5-[(4,5-dichloro-1-ethyl-1H-indole-2-carbonyl)-amino]-pyridin-2-yl}-piperazin-1-yl)-2,2-dimethyl-4-oxo-butyric acid was prepared from 4,5-dichloro-1-ethyl-1H-indole-2-carboxylic acid (6-piperazin-1-yl-pyridin-3-yl)-amide and 2,2-dimethylsuccinic anhydride. LCMS for $C_{26}H_{29}Cl_2N_5O_4$ calcd. (m/e) 545, observed 546 (M+H).

Example 20

4-{5-[(1-Ethyl-4-methoxy-1H-indole-2-carbonyl)-amino]-pyridin-2-yl}-piperazine-1-carboxylic acid tert-butyl ester

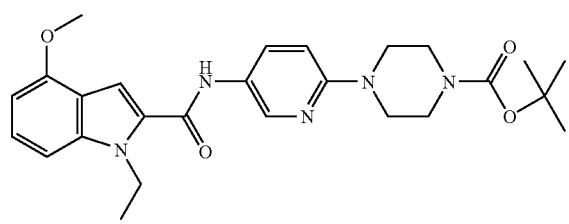

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(1-ethyl-4-methoxy-1H-indole-2-carbonyl)-amino]-pyridin-2-yl}-piperazine-1-carboxylic acid tert-butyl ester was prepared from N-ethyl-4-methoxy-indole-2-carboxylic acid and 4-(5-amino-pyridin-2-yl)-piperazine-1-carboxylic acid tert-butyl ester. LCMS for $C_{26}H_{33}N_5O_4$ calcd. (m/e) 479, observed 480 (M+H).

Example 21

4-{5-[(1-Ethyl-4-methoxy-1H-indole-2-carbonyl)-amino]-pyridin-2-yl}-piperazine-1-carboxylic acid ethyl ester

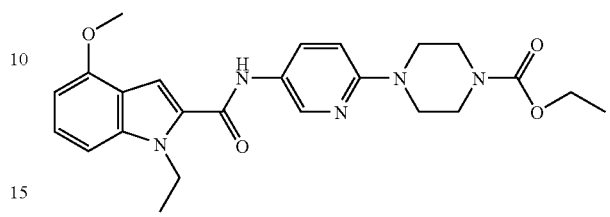

With a method similar to that used for the preparation of 4-{5-[(4-chloro-benzo[b]thiophene-2-carbonyl)-amino]-pyridin-2-yl}-piperazine-1-carboxylic acid tert-butyl ester, 4-{5-[(1-ethyl-4-methoxy-1H-indole-2-carbonyl)-amino]-pyridin-2-yl}-piperazine-1-carboxylic acid ethyl ester was prepared from 1-ethyl-4-methoxy-1H-indole-2-carboxylic acid and 4-(5-amino-pyridin-2-yl)-piperazine-1-carboxylic acid tert-butyl ester followed by the deprotection of the BOC group and subsequent carbamate formation with ethyl chloroformate. LCMS for $C_{24}H_{29}N_5O_4$ calcd. (m/e) 451, observed 452 (M+H).

Example 22

4-{5-[(1-Ethyl-4,5-dimethoxy-1H-indole-2-carbonyl)-amino]-pyridin-2-yl}-piperazine-1-carboxylic acid tert-butyl ester

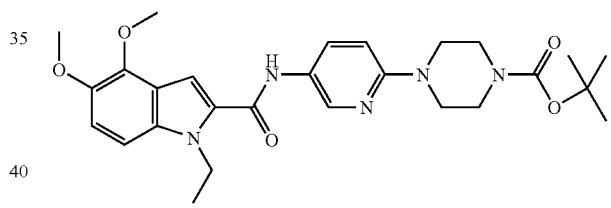

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(1-ethyl-4,5-dimethoxy-1H-indole-2-carbonyl)-amino]-pyridin-2-yl}-piperazine-1-carboxylic acid tert-butyl ester was prepared from N-ethyl-4,5-methoxy-indole-2-carboxylic acid and 4-(5-amino-pyridin-2-yl)-piperazine-1-carboxylic acid tert-butyl ester. LCMS for $C_{27}H_{35}N_5O_5$ calcd. (m/e) 509, observed 510 (M+H).

Example 23

4-{5-[(5-Chloro-1-ethyl-1H-indole-2-carbonyl)-amino]-pyridin-2-yl}-piperazine-1-carboxylic acid tert-butyl ester

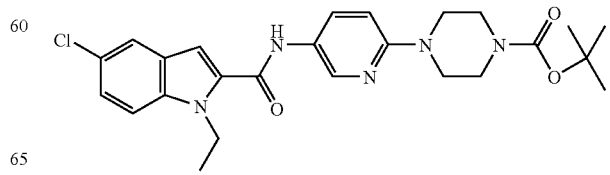

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{5-[(5-chloro-1-ethyl-1H-indole-2-carbonyl)-amino]-pyridin-2-yl}-piperazine-1-carboxylic acid tert-butyl ester was prepared from N-ethyl-5-chloro-indole-2-carboxylic acid and 4-(5-amino-pyridin-2-yl)-piperazine-1-carboxylic acid tert-butyl ester. LCMS for $C_{25}H_{30}ClN_5O_3$ calcd. (m/e) 483, observed 484 (M+H).

Example 24

4-{4-[(4-Chloro-benzo[b]thiophene-2-carbonyl)-amino]-phenyl}-piperazine-1-carboxylic acid tert-butyl ester

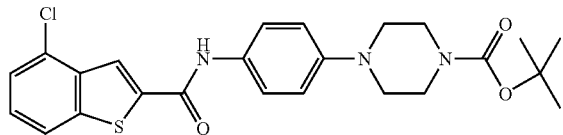

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{4-[(4-chloro-benzo[b]thiophene-2-carbonyl)-amino]-phenyl}-piperazine-1-carboxylic acid tert-butyl ester was prepared from 4-chloro-benzothiophene-2-carboxylic acid and 4-(4-amino-phenyl)-piperazine-1-carboxylic acid tert-butyl ester. LCMS for $C_{24}H_{26}ClN_3O_3S$ calcd. (m/e) 471, observed 472 (M+H).

Example 25

4-(4-{4-[(4-Chloro-benzo[b]thiophene-2-carbonyl)-amino]-phenyl}-piperidin-1-yl)-2,2-dimethyl-4-oxo-butyric acid

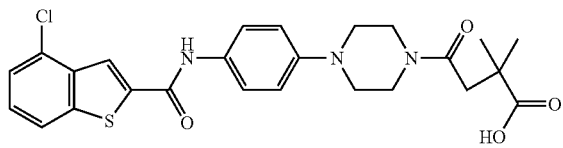

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{4-[(4-chloro-benzo[b]thiophene-2-carbonyl)-amino]-phenyl}-piperidin-1-yl)-2,2-dimethyl-4-oxo-butyric acid was prepared from 4-chloro-benzo[b]thiophene-2-carboxylic acid (4-piperidin-4-yl-phenyl)-amide. LCMS for $C_{26}H_{27}ClN_2O_4S$ calcd. (m/e) 498, observed 497 (M−H).

Example 26

4-(4-{4-[(4-Chloro-benzo[b]thiophene-2-carbonyl)-amino]-phenyl}-piperazin-1-yl)-2,2-dimethyl-4-oxo-butyric acid

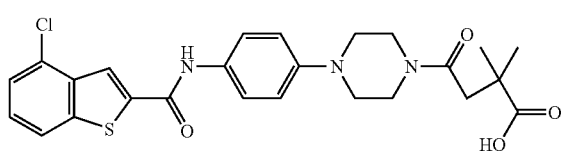

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{4-[(4-chloro-benzo[b]thiophene-2-carbonyl)-amino]-phenyl}-piperazin-1-yl)-2,2-dimethyl-4-oxo-butyric acid was prepared from 4-chloro-benzo[b]thiophene-2-carboxylic acid (4-piperazin-4-yl-phenyl)-amide. LCMS for $C_{25}H_{26}ClN_3O_4S$ calcd. (m/e) 499, observed 498 (M−H).

Example 27 trans-4-(4-{5-[(1-Ethyl-4-methoxy-1H-indole-2-carbonyl)-amino]-pyridin-2-yl}-piperazine-1-carbonyl)-cyclohexanecarboxylic acid benzyl ester

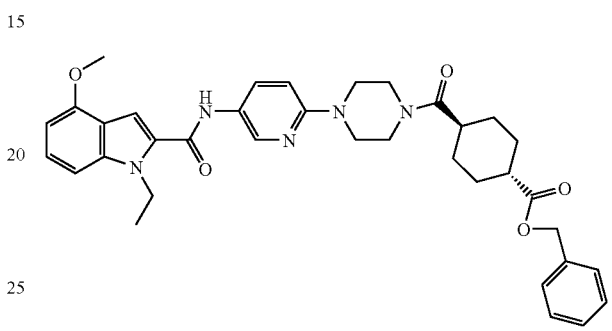

A mixture of trans-cyclohexane-1,4-dicarboxylic acid mono-benzyl ester (50 mg, 0.16 mmol), $CH_2Cl_2$ (5 mL), and a catalytic amount of DMF was stirred under Ar, and oxalyl chloride (2M in dichloromethane, 200 μL, 0.4 mmol) was dripped into the mixture over 5 min. The mixture was stirred at room temperature and after 1.0 hr the reaction was concentrated to dryness. Benzene was added and the solution was evaporated to dryness again. The white-yellow solid was re-dissolved in 5 mL of $CH_2Cl_2$ and dripped, under Ar, into a solution of 1-ethyl-4-methoxy-1H-indole-2-carboxylic acid (6-piperazin-1-yl-pyridin-3-yl)-amide (60.0 mg, 0.16 mmol), triethylamine (0.41 mg, 0.2 mmol) in 5 mL of $CH_2Cl_2$. The reaction was stirred at room temperature for 0.5 hr then concentrated and the residue was taken up in 50 mL of EtOAc and washed with 50 mL of saturated ammonium chloride, brine and dried with anhydrous sodium sulfate. The solvent was removed, and the crude product was purified by flash chromatography (hexanes:EtOAc), to afford the product trans-4-(4-{5-[(1-ethyl-4-methoxy-1H-indole-2-carbonyl)-amino]-pyridin-2-yl}-piperazine-1-carbonyl)-cyclohexanecarboxylic acid benzyl ester (35 mg, 37% yield) as a white solid. LCMS for $C_{36}H_{41}N_5O_5$ calcd. (m/e) 623, observed 624 (M+H).

Example 28 trans-4-(4-{5-[(1-Ethyl-4-methoxy-1H-indole-2-carbonyl)-amino]-pyridin-2-yl}-piperazine-1-carbonyl)-cyclohexanecarboxylic acid

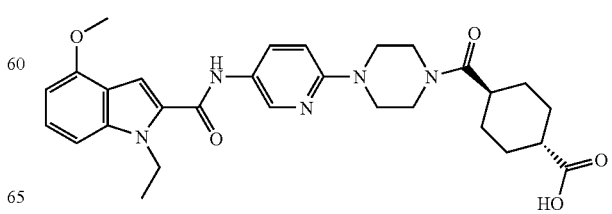

A mixture of trans-4-(4-{5-[(1-ethyl-4-methoxy-1H-indole-2-carbonyl)-amino]-pyridin-2-yl}-piperazine-1-carbonyl)-cyclohexanecarboxylic acid benzyl ester (30 mg, 0.05 mmol), 10% Pd/C (50 mg) in methanol (20 mL) was hydrogenated at 50 psi for 2 hr. The solution was filtered and the solvent was removed to afford the product, trans-4-(4-{5-[(1-ethyl-4-methoxy-1H-indole-2-carbonyl)-amino]-pyridin-2-yl}-piperazine-1-carbonyl)-cyclohexane carboxylic acid, as a green solid (10 mg, 40% yield). LCMS for $C_{29}H_{35}N_5O_5$ calcd. (m/e) 533, observed 534 (M+H).

Example 29 trans-4-(4-{4-[(4-Ethoxy-1-ethyl-1H-indole-2-carbonyl)-amino]-phenyl}-piperazine-1-carbonyl)-cyclohexanecarboxylic acid

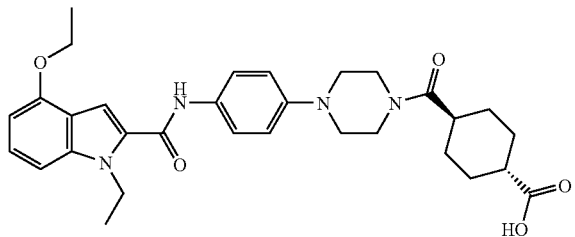

With a method similar to that used for the preparation of trans-4-(4-{5-[(1-ethyl-4-methoxy-1H-indole-2-carbonyl)-amino]-pyridin-2-yl}-piperazine-1-carbonyl)-cyclohexane carboxylic acid, trans-4-(4-{4-[(4-ethoxy-1-ethyl-1H-indole-2-carbonyl)-amino]-phenyl}-piperazine-1-carbonyl)-cyclohexanecarboxylic acid was prepared from trans-4-(4-{4-[(4-ethoxy-1-ethyl-1H-indole-2-carbonyl)-amino]-phenyl}-piperazine-1-carbonyl)-cyclohexanecarboxylic acid benzyl ester. LCMS for $C_{31}H_{38}N_4O_5$ calcd. (m/e) 546, observed 547 (M+H).

Example 30 trans-4-(4-{4-[(1-Ethyl-4-methyl-1H-indole-2-carbonyl)-amino]-phenyl}-piperidine-1-carbonyl)-trans-1,4-cyclohexanecarboxylic acid

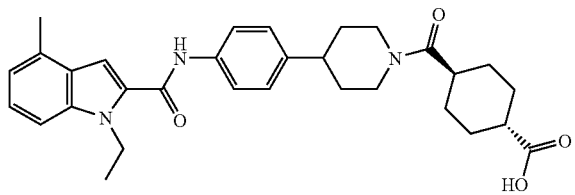

With a method similar to that used for the preparation of trans-4-(4-{5-[(1-ethyl-4-methoxy-1H-indole-2-carbonyl)-amino]-pyridin-2-yl}-piperazine-1-carbonyl)-cyclohexane carboxylic acid, trans-4-(4-{4-[(1-ethyl-4-methyl-1H-indole-2-carbonyl)-amino]-phenyl}-piperidine-1-carbonyl)-cyclohexanecarboxylic acid was prepared from trans-4-(4-{4-[1-ethyl-4-methyl-1H-indole-2-carbonyl)-amino]-phenyl}-piperidine-1-carbonyl)-cyclohexanecarboxylic acid benzyl ester. LCMS for $C_{31}H_{37}N_3O_4$ calcd. (m/e) 515, observed 516 (M+H).

Example 31

(1R,2R)-2-(4-{4-[(4-Ethoxy-1-ethyl-1H-indole-2-carbonyl)-amino]-phenyl}-piperazine-1-carbonyl)-cyclopentanecarboxylic acid

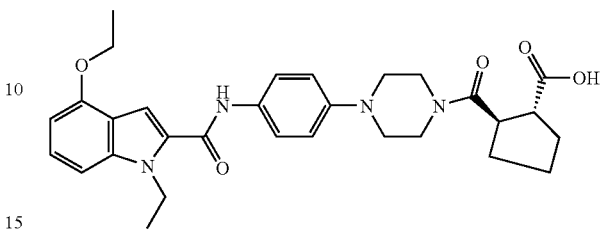

With a method similar to that used for the preparation of trans-4-(4-{5-[(1-ethyl-4-methoxy-1H-indole-2-carbonyl)-amino]-pyridin-2-yl}-piperazine-1-carbonyl)-cyclohexane carboxylic acid, (1R,2R)-2-(4-{4-[(4-ethoxy-1-ethyl-1H-indole-2-carbonyl)-amino]-phenyl}-piperazine-1-carbonyl)-cyclopentanecarboxylic acid was prepared from (1R,2R)-2-(4-{4-[(4-ethoxy-1-ethyl-1H-indole-2-carbonyl)-amino]-phenyl}-piperazine-1-carbonyl)-cyclopentanecarboxylic acid benzyl ester. LCMS for $C_{30}H_{36}N_4O_5$ calcd. (m/e) 532, observed 533 (M+H).

Example 32

(1R,2R)-2-(4-{4-[(4-Ethoxy-1-ethyl-1,1-indole-2-carbonyl)-amino]-phenyl}-piperidine-1-carbonyl)-cyclopentanecarboxylic acid

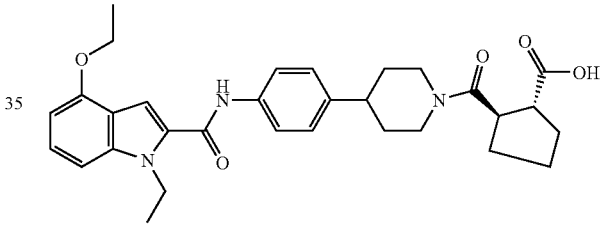

With a method similar to that used for the preparation of trans-4-(4-{5-[(1-ethyl-4-methoxy-1H-indole-2-carbonyl)-amino]-pyridin-2-yl}-piperazine-1-carbonyl)-cyclohexane carboxylic acid, (1R,2R)-2-(4-{4-[(4-ethoxy-1-ethyl-1H-indole-2-carbonyl)-amino]-phenyl}-piperidine-1-carbonyl)-cyclopentanecarboxylic acid was prepared from (1R,2R)-2-(4-{4-[(4-ethoxy-1-ethyl-1H-indole-2-carbonyl)-amino]-phenyl}-piperidine-1-carbonyl)-cyclopentanecarboxylic acid benzyl ester. LCMS for $C_{31}H_{37}N_3O_5$ calcd. (m/e) 531, observed 532 (M+H).

Example 33

1-Ethyl-5-trifluoromethoxy-1H-indole-2-carboxylic acid {6-[(2-methoxy-ethyl)-methyl-amino]-pyridin-3-yl}-amide hydrochloride

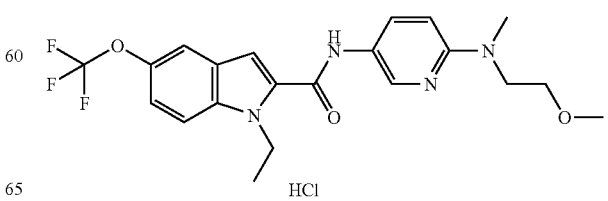

A mixture of 1-ethyl-5-trifluoromethoxy-1H-indole-2-carboxylic acid (65 mg, 0.24 mmol), CH$_2$Cl$_2$ (5 mL), and catalytic amount of DMF was stirred under Ar, and oxalyl chloride (2M in dichloromethane, 250 μL, 0.5 mmol) was dripped into the mixture over 5 min. The mixture was stirred at room temperature for 1.0 hr and then concentrated to dryness. Benzene was added and the solution was evaporated to dryness again. The residue was re-dissolved in 5 mL of CH$_2$Cl$_2$ and dripped, under Ar, into a solution of N-(2-methoxy-ethyl)-N-methyl-pyridine-2,5-diamine (43.0 mg, 0.24 mmol), and triethylamine (0.52 mg, 0.5 mmol) in 5 mL of CH$_2$Cl$_2$. The reaction was stirred at room temperature for 0.5 hr then concentrated and the residue was taken up in 50 mL of EtOAc and washed with 50 mL of saturated ammonium chloride, brine and dried with anhydrous sodium sulfate. The solvent was removed, and the crude product was purified by flash chromatography (hexanes:EtOAc) followed by conversion to HCl salt with 1N HCl in ether to afford the product, 1-ethyl-5-trifluoromethoxy-1H-indole-2-carboxylic acid {6-[(2-methoxy-ethyl)-methyl-amino]-pyridin-3-yl}-amide hydrochloride, as a pink solid (44 mg, 42% yield). LCMS for C$_{21}$H$_{23}$F$_3$N$_4$O$_3$ calcd. (m/e) 436, observed 437 (M+H).

Example 34

Benzo[b]thiophene-2-carboxylic acid {6-[(2-methoxy-ethyl)-methyl-amino]-pyridin-3-yl}-amide

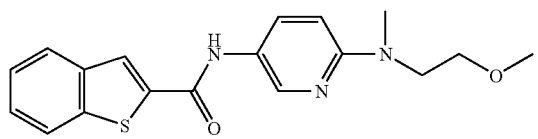

With a method similar to that used for the preparation of 1-ethyl-5-trifluoromethoxy-1H-indole-2-carboxylic acid {6-[(2-methoxy-ethyl)-methyl-amino]-pyridin-3-yl}-amide, benzo[b]thiophene-2-carboxylic acid {6-[(2-methoxy-ethyl)-methyl-amino]-pyridin-3-yl}-amide was prepared from benzothiophene-2-carboxylic acid. LCMS for C$_{18}$H$_{19}$N$_3$O$_2$S calcd. (m/e) 341, observed 342 (M+H).

Example 35

3-Methyl-benzo[b]thiophene-2-carboxylic acid {6-[(2-methoxy-ethyl)-methyl-amino]-pyridin-3-yl}-amide hydrochloride

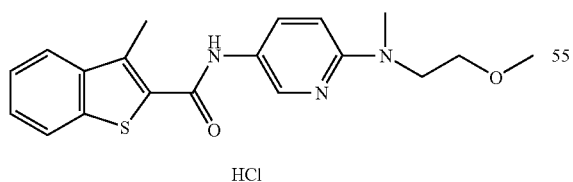

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 3-methyl-benzo[b]thiophene-2-carboxylic acid {6-[(2-methoxy-ethyl)-methyl-amino]-pyridin-3-yl}-amide hydrochloride was prepared from 3-methyl-benzothiophene-2-carboxylic acid. LCMS for C$_{19}$H$_{21}$N$_3$O$_2$S calcd. (m/e) 355, observed 356 (M+H).

Example 36

3-Methyl-benzo[b]thiophene-2-carboxylic acid {2-[(2-methoxy-ethyl)-methyl-amino]-pyrimidin-5-yl}-amide hydrochloride

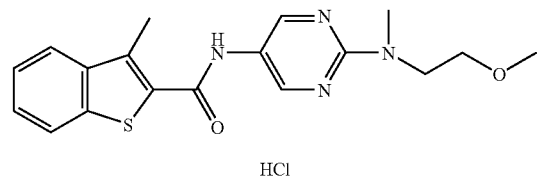

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 3-methyl-benzo[b]thiophene-2-carboxylic acid {2-[(2-methoxy-ethyl)-methyl-amino]-pyrimidin-5-yl}-amide hydrochloride was prepared from 3-methyl-benzothiophene-2-carboxylic acid. LCMS for C$_{18}$H$_{20}$N$_4$O$_2$S calcd. (m/e) 356, observed 357 (M+H).

Example 37

1-Ethyl-1H-indole-2-carboxylic acid {6-[(2-methoxy-ethyl)-methyl-amino]-pyridin-3-yl}-amide hydrochloride

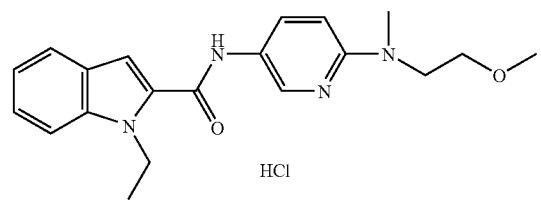

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 1-ethyl-1H-indole-2-carboxylic acid {6-[(2-methoxy-ethyl)-methyl-amino]-pyridin-3-yl}-amide hydrochloride was prepared from 1-ethyl-1H-indole-2-carboxylic acid. LCMS for C$_{20}$H$_{24}$N$_4$O$_2$ calcd. (m/e) 352, observed 353 (M+H).

Example 38

1-Ethyl-4-methoxy-1H-indole-2-carboxylic acid {6-[(2-methoxy-ethyl)-methyl-amino]-pyridin-3-yl}-amide hydrochloride

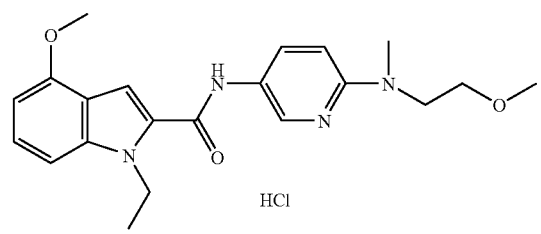

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 1-ethyl-4-methoxy-1H-indole-2-carboxylic acid {6-[(2-methoxy-ethyl)-methyl-amino]-pyridin-3-yl}-amide hydrochloride was prepared from 1-ethyl-4-methoxy-1H-indole-2-carboxylic acid. LCMS for $C_{21}H_{26}N_4O_3$ calcd. (m/e) 382, observed 383 (M+H).

Example 39

1-Ethyl-5-methoxy-1H-indole-2-carboxylic acid {6-[(2-methoxy-ethyl)-methyl-amino]pyridin-3-yl}-amide hydrochloride

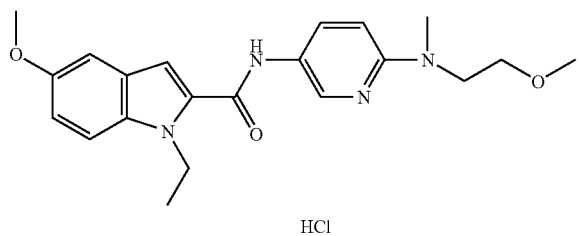

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 1-ethyl-5-methoxy-1H-indole-2-carboxylic acid {6-[(2-methoxy-ethyl)-methyl-amino]-pyridin-3-yl}-amide hydrochloride was prepared from 1-ethyl-5-methoxy-1H-indole-2-carboxylic acid. LCMS for $C_{21}H_{26}N_4O_3$ calcd. (m/e) 382, observed 383 (M+H).

Example 40

5-Benzyloxy-1-ethyl-1H-indole-2-carboxylic acid {6-[(2-methoxy-ethyl)-methyl-amino]-pyridin-3-yl}-amide

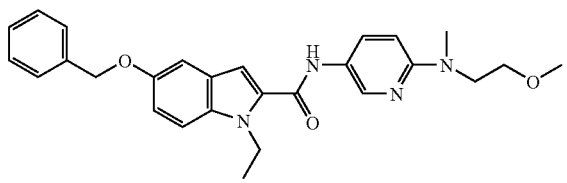

With a method similar to that used for the preparation of 1-ethyl-5-trifluoromethoxy-1H-indole-2-carboxylic acid {6-[(2-methoxy-ethyl)-methyl-amino]-pyridin-3-yl}-amide, 5-benzyloxy-1-ethyl-1H-indole-2-carboxylic acid {6-[(2-methoxy-ethyl)-methyl-amino]-pyridin-3-yl}-amide was prepared from 5-benzyloxy-1-ethyl-1H-indole-2-carboxylic acid. LCMS for $C_{27}H_{30}N_4O_3$ calcd, (m/e) 458, observed 459 (M+H).

Example 41

1-Propyl-1H-indole-2-carboxylic acid {6-[(2-methoxy-ethyl)-methyl-amino]-pyridin-3-yl}-amide hydrochloride

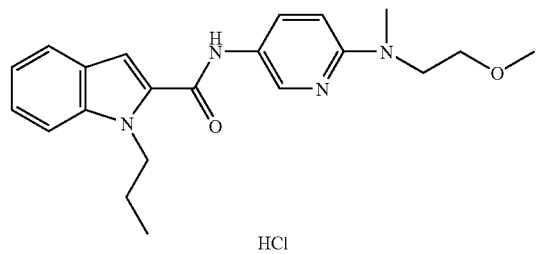

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 1-propyl-1H-indole-2-carboxylic acid {6-[(2-methoxy-ethyl)-methyl-amino]-pyridin-3-yl}-amide hydrochloride was prepared from 1-propyl-1H-indole-2-carboxylic acid. LCMS for $C_{21}H_{26}N_4O_2$ calcd. (m/e) 366, observed 367 (M+H).

Example 42

5-Chloro-1-methyl-1H-indole-2-carboxylic acid {6-[(2-methoxy-ethyl)-methyl-amino]-pyridin-3-yl}-amide hydrochloride

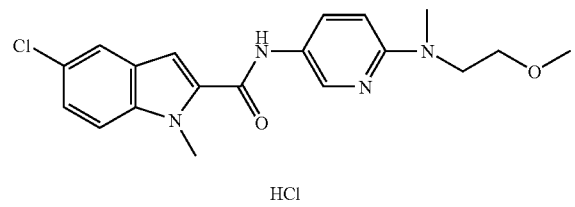

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 5-chloro-1-methyl-1H-indole-2-carboxylic acid {6-[(2-methoxy-ethyl)-methyl-amino]-pyridin-3-yl}-amide hydrochloride was prepared from 5-chloro-1-methyl-1H-indole-2-carboxylic acid. LCMS for $C_{19}H_{21}ClN_4O_2$ calcd. (m/e) 372, observed 373 (M+H).

Example 43

5-Chloro-1-ethyl-4H-indole-2-carboxylic acid {6-[(2-methoxy-ethyl)-methyl-amino]-pyridin-3-yl}-amide hydrochloride

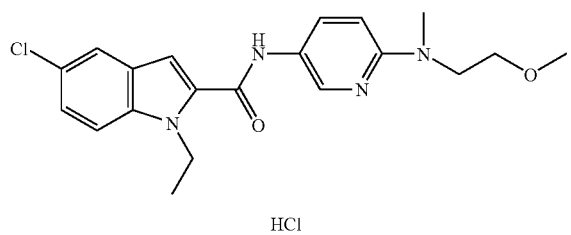

HCl

With a method similar to that used for the preparation of 1-ethyl-5-trifluoromethoxy-1H-indole-2-carboxylic acid {6-[(2-methoxy-ethyl)-methyl-amino]-pyridin-3-yl}-amide hydrochloride, 5-chloro-1-ethyl-1H-indole-2-carboxylic acid {6-[(2-methoxy-ethyl)-methyl-amino]-pyridin-3-yl}-amide hydrochloride was prepared from 5-chloro-1-ethyl-1H-indole-2-carboxylic acid. LCMS for $C_{20}H_{23}ClN_4O_2$ calcd. (m/e) 386, observed 387 (M+H).

Example 44

4-(4-{4-[(4-Ethoxy-1-ethyl-1H-indole-2-carbonyl)-amino]-phenyl}-piperazin-1-yl)-2,2-dimethyl-4-oxo-butyric acid

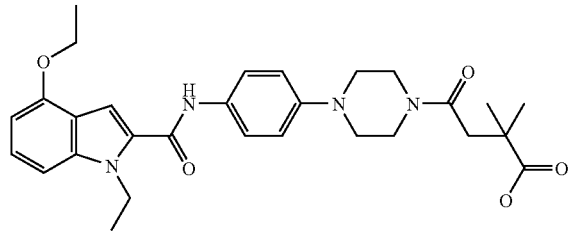

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{4-[(4-ethoxy-1-ethyl-1,1-indole-2-carbonyl)-amino]-phenyl}-piperazin-1-yl)-2,2-dimethyl-4-oxo-butyric acid was prepared from 4-ethoxy-1-ethyl-1H-indole-2-carboxylic acid (4-piperazin-4-yl-phenyl)-amide. LCMS for $C_{29}H_{36}N_4O_5$ calcd. (m/e) 520, observed 521 (M+H).

Example 45

5-Chloro-1-ethyl-1H-indole-2-carboxylic acid [6-(cyclopropyl-methyl-amino)-pyridin-3-yl]-amide

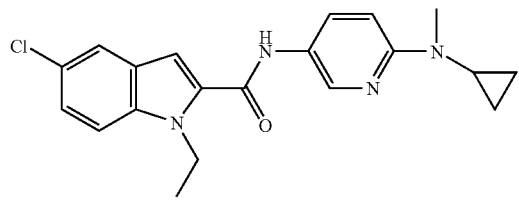

With a method similar to that used for the preparation of 1-ethyl-5-trifluoromethoxy-1H-indole-2-carboxylic acid {6-[(2-methoxy-ethyl)-methyl-amino]-pyridin-3-yl}-amide, 5-chloro-1-ethyl-1H-indole-2-carboxylic acid [6-(cyclopropyl-methyl-amino)-pyridin-3-yl]-amide was prepared from 5-chloro-1-ethyl-1H-indole-2-carboxylic acid and N-2-cyclopropyl-N-2-methyl-pyridine-2,5-diamine. LCMS for $C_{20}H_{21}ClN_4O$ calcd. (m/e) 368, observed 369 (M+H).

Example 46

(S)-3-{5-[(5-Bromo-benzo[b]thiophene-2-carbonyl)-amino]pyridin-2-ylamino}-pyrrolidine-1-carboxylic acid ethyl ester hydrochloride

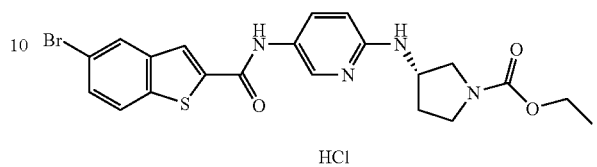

To a suspension of 5-bromobenzothiophene-2-carboxylic acid (109 mg, 0.42 mmol) in dichloromethane (5 mL) was added oxalyl chloride (2M in dichloromethane, 0.5 mL) and one drop of DMF. The mixture was stirred at room temperature for 1 hr and solvents were evaporated. The residue was diluted with benzene (10 mL) and then concentrated to dryness. The residue was dissolved in dichloromethane (5 mL) and treated with (S)-3-(5-amino-pyridin-2-ylamino)-pyrrolidine-1-carboxylic acid ethyl ester (106 mg, 0.42 mmol) in dichloromethane (5 mL) containing triethylamine (0.1 mL). The mixture was stirred at room temperature for 1 hr and solvents were evaporated. The residue was extracted with ethyl acetate and saturated ammonium chloride solution. Organic layer was washed with brine and dried over sodium sulfate. Solvents were evaporated and the residue was treated with methanol (1 mL) and hydrogen chloride in ether. Solvents were evaporated and the residue was treated with ether. The precipitate was filtered and washed with ether to give a light pink solid as (S)-3-{5-[(5-bromo-benzo[b]thiophene-2-carbonyl)-amino]-pyridin-2-ylamino}-pyrrolidine-1-carboxylic acid ethyl ester hydrochloride (100 mg, 48.3% yield). LCMS for $C_{21}H_{21}BrN_4O_3S$ calcd. (m/e) 488, observed 489 (M+H).

Example 47

(S)-3-{5-[(4-Chloro-benzo[b]thiophene-2-carbonyl)-amino]pyridin-2-ylamino}-pyrrolidine-1-carboxylic acid ethyl ester hydrochloride

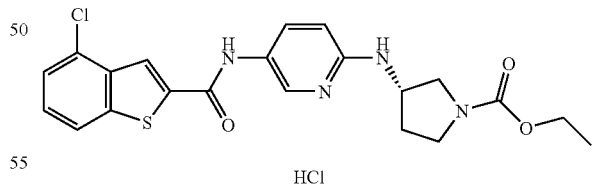

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(4-chloro-benzo[b]thiophene-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and 4-chloro-benzothiophene-2-carboxylic acid. LCMS for $C_{21}H_{21}ClN_4O_3S$ calcd. (m/e) 444, observed 445 (M+H).

Example 48

(S)-3-{5-[(Benzo[b]thiophene-2-carbonyl)-amino]-pyridin-2-ylamino}-pyrrolidine-1-carboxylic acid ethyl ester hydrochloride

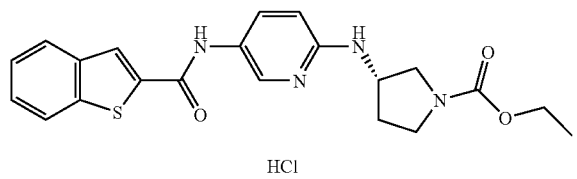

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(benzo[b]thiophene-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and benzothiophene-2-carboxylic acid. LCMS for $C_{21}H_{22}N_4O_3S$ calcd. (m/e) 410 observed 411 (M+H).

Example 49

(S)-3-{5-[(5-Trifluoromethyl-benzo[b]thiophene-2-carbonyl)-amino]-pyridin-2 ylamino}-pyrrolidine-1-carboxylic acid ethyl ester hydrochloride

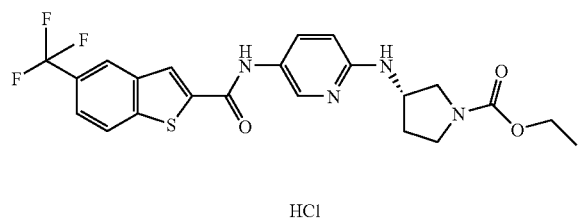

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(5-trifluoromethyl-benzo[b]thiophene-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and 5-trifluoromethyl-benzothiophene-2-carboxylic acid. LCMS for $C_{22}H_{21}F_3N_4O_3S$ calcd. (m/e) 478, observed 479 (M+H).

Example 50

(S)-3-{5-[(5-Bromo-1-ethyl-1H-indole-2-carbonyl)-amino]-pyridin-2-ylamino}-pyrrolidine-1-carboxylic acid ethyl ester hydrochloride

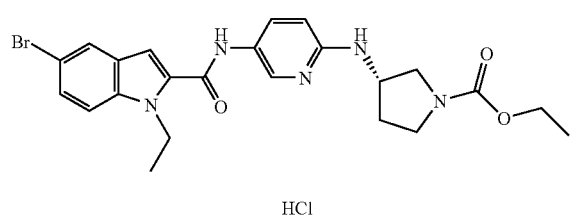

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(5-bromo-1-ethyl-1,4-indole-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and 5-bromo-1-ethyl-indole-2-carboxylic acid. LCMS for $C_{23}H_{26}BrN_5O_3$ calcd. (m/e) 499, observed 500 (M+H).

Example 51

(S)-3-{5-[(1-Ethyl-5-methoxy-1H-indole-2-carbonyl)-amino]-pyridin-2-ylamino}-pyrrolidine-1-carboxylic acid ethyl ester hydrochloride

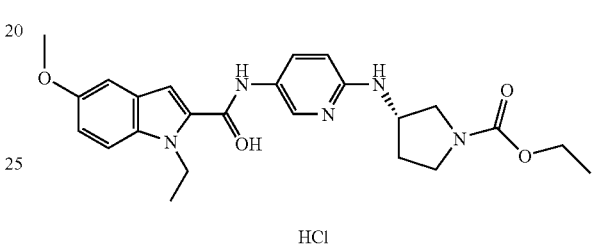

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(1-ethyl-5-methoxy-1H-indole-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and N-ethyl-5-methoxy-indole-2-carboxylic acid. LCMS for $C_{24}H_{29}N_5O_4$ calcd. (m/e) 451, observed 452 (M+H).

Example 52

(S)-3-{5-[(1-Ethyl-4,6-dimethoxy-1H-indole-2-carbonyl)-amino]-pyridin-2-ylamino}pyrrolidine-1-carboxylic acid ethyl ester

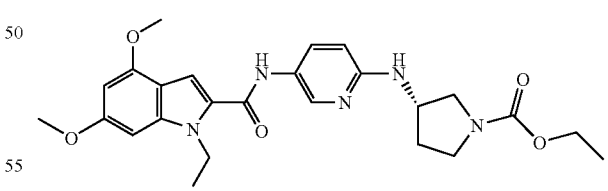

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(1-ethyl-4,6-dimethoxy-1H-indole-2-carbonyl)-amino]-pyridin-2-ylamino}-pyrrolidine-1-carboxylic acid ethyl ester was prepared from (S)-3-(5-amino-pyridin-2-ylamino)-pyrrolidine-1-carboxylic acid ethyl ester and N-ethyl-4,6-dimethoxy-indole-2-carboxylic acid. LCMS for $C_{25}H_{31}N_5O_5$ calcd. (m/e) 481, observed 482 (M+H).

Example 53

(S)-3-{5-[(1-Ethyl-4-methyl-1H-indole-2-carbonyl)-amino]-pyridin-2-ylamino}-pyrrolidine-1-carboxylic acid ethyl ester hydrochloride

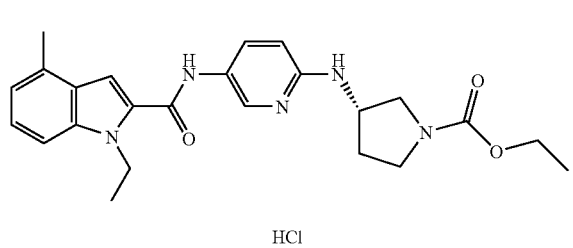

HCl

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(1-ethyl-4-methyl-1H-indole-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and N-ethyl-4-methyl-indole-2-carboxylic acid. LCMS for $C_{24}H_{29}N_5O_3$ calcd. (m/e) 435, observed 436 (M+H).

Example 54

(S)-3-{5-[(1-Ethyl-4,5-dimethoxy-1H-indole-2-carbonyl)-amino]-pyridin-2-ylamino}pyrrolidine-1-carboxylic acid ethyl ester hydrochloride

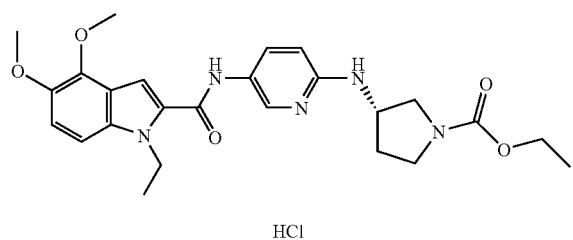

HCl

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(1-ethyl-4,5-dimethoxy-1H-indole-2-carbonyl)-amino]-pyridin-2-ylamino}-pyrrolidine-t-carboxylic acid ethyl ester hydrochloride was prepared from (S)-3-(5-amino-pyridin-2-ylamino)-pyrrolidine-t-carboxylic acid ethyl ester and N-ethyl-4,5-dimethoxy-indole-2-carboxylic acid. LCMS for $C_{25}H_{31}N_5O_5$ calcd. (m/e) 481, observed 482 (M+H).

Example 55

(S)-3-{5-[(4-Ethoxy-1-ethyl-1H-indole-2-carbonyl)-amino]-pyridin-2-ylamino}-pyrrolidine-1-carboxylic acid ethyl ester hydrochloride

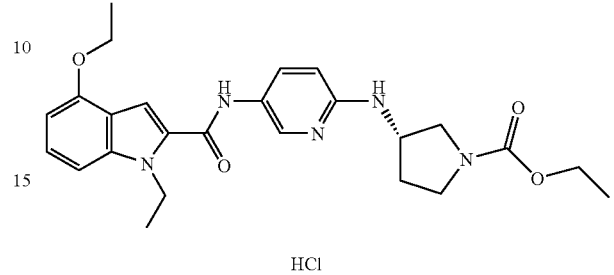

HCl

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(4-ethoxy-1-ethyl-1H-indole-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and N-ethyl-4-ethoxy-indole-2-carboxylic acid. LCMS for $C_{25}H_{31}N_5O_4$ calcd. (m/e) 465, observed 466 (M+H).

Example 56

(S)-3-{5-[(5-Chloro-1-ethyl-1H-indole-2-carbonyl)-amino]-pyridin-2-ylamino}-pyrrolidine-1-carboxylic acid ethyl ester

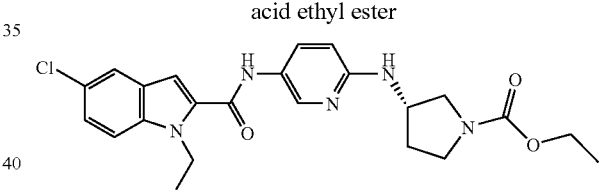

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(5-chloro-1-ethyl-1H-indole-2-carbonyl)-amino]-pyridin-2-ylamino}-pyrrolidine-1-carboxylic acid ethyl ester was prepared from (S)-3-(5-amino-pyridin-2-ylamino)-pyrrolidine-1-carboxylic acid ethyl ester and N-ethyl-5-chloro-indole-2-carboxylic acid. LCMS for $C_{23}H_{26}ClN_5O_3$ calcd. (m/e) 455, observed 456 (M+H).

Example 57

(S)-3-{5-[(4,5-Dichloro-1-ethyl-1H-indole-2-carbonyl)-amino]-pyridin-2-ylamino}-pyrrolidine-1-carboxylic acid ethyl ester hydrochloride

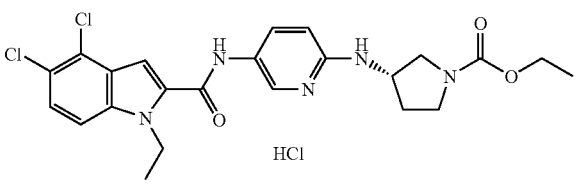

HCl

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, (S)-3-{5-[(4,5-dichloro-1-ethyl-1H-indole-2-carbonyl)-amino]-pyridin-2-ylamino}-pyrrolidine-1-carboxylic acid ethyl ester hydrochloride was prepared from (S)-3-(5-amino-pyridin-2-ylamino)-pyrrolidine-1-carboxylic acid ethyl ester and N-ethyl-4,5-dichloro-indole-2-carboxylic acid. LCMS for $C_{23}H_{25}Cl_2N_5O_3$ calcd. (m/e) 489, observed 490 (M+H).

Example 58

1-Ethyl-4-methyl-1H-indole-2-carboxylic acid [6-((S)-1-tert-butylcarbamoyl-pyrrolidin-3-ylamino)-pyridin-3-yl]-amide hydrochloride

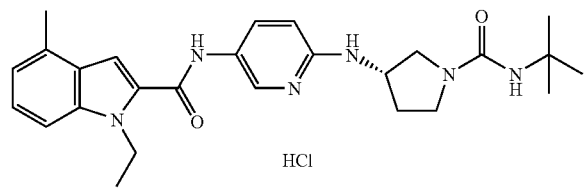

With a method similar to that used for the preparation of (S)-3-{5-[(5-bromo-benzo[b]thiophene-2-carbonyl)-amino]-pyridin-2-ylamino}-pyrrolidine-1-carboxylic acid ethyl ester hydrochloride, 1-ethyl-4-methyl-1,4-indole-2-carboxylic acid [6-((S)-1-tert-butylcarbamoyl-pyrrolidin-3-ylamino)-pyridin-3-yl]-amide was prepared from (S)-3-(5-amino-pyridin-2-ylamino)-pyrrolidine-1-carboxylic acid tert-butylamide and N-ethyl-4-methyl-indole-2-carboxylic acid. LCMS for $C_{26}H_{34}N_6O_2$ calcd. (m/e) 462, observed 463 (M+H).

Example 59

4-{4-[(4,5-Dichloro-1-ethyl-1H-indole-2-carbonyl)-amino]-phenyl}-piperazine-1-carboxylic acid tert-butyl ester

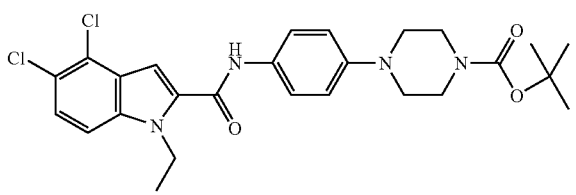

With a method similar to that for the preparation of 4-{5-[(4-chloro-benzo[b]thiophene-2-carbonyl)-amino]-pyridin-2-yl}-piperazine-1-carboxylic acid tert-butyl ester, 4-{4-[(4,5-dichloro-1-ethyl-1H-indole-2-carbonyl)-amino]-phenyl}-piperazine-1-carboxylic acid tert-butyl ester was prepared from N-ethyl-4,5-dichloro-indole-2-carboxylic acid and 4-(4-amino-phenyl)-piperazine-1-carboxylic acid tert-butyl ester. LCMS for $C_{26}H_{30}Cl_2N_4O_3$ calcd. (m/e) 516, observed 517 (M+H).

Example 60

4-(4-{4-[(4,5-Dichloro-1-ethyl-1H-indole-2-carbonyl)-amino]-phenyl}-piperazin-1-yl)-2,2-dimethyl-4-oxo-butyric acid

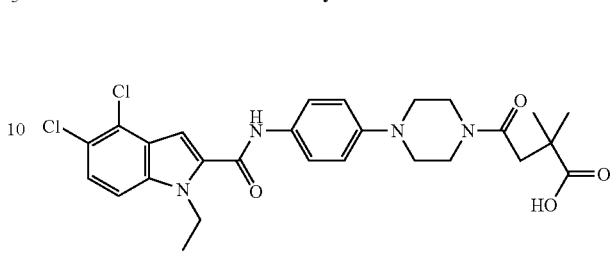

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 4-(4-{4-[(4,5-dichloro-1-ethyl-1H-indole-2-carbonyl)-amino]phenyl}-piperazin-1-yl)-2,2-dimethyl-4-oxo-butyric acid was prepared from 4,5-dichloro-1-ethyl-1H-indole-2-carboxylic acid (4-piperazin-1-yl-phenyl)-amide and 3,3-dimethyl-dihydro-furan-2,5-dione. LCMS for $C_{27}H_{30}Cl_2N_4O_4$ calcd. (m/e) 544, observed 545 (M+H).

Example 61

4-(4-{4-[(4,5-Dichloro-1-ethyl-1H-indole-2-carbonyl)-amino]-phenyl}-piperidin-1-yl)-4-oxo-2-phenyl-butyric acid

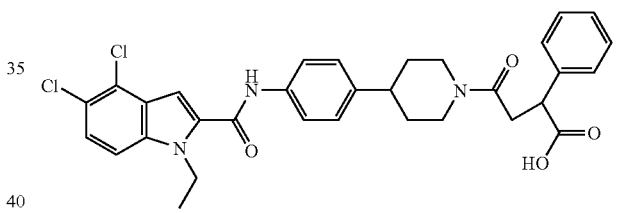

With a method similar to that used for the preparation of 4-(4-{4-[(4-ethoxy-1-ethyl-1H-indole-2-carbonyl)-amino]-phenyl}-piperidin-1-yl)-2,2-dimethyl-4-oxo-butyric acid, 4-(4-{4-[(4,5-dichloro-1-ethyl-1H-indole-2-carbonyl)-amino]-phenyl}-piperidin-1-yl)-4-oxo-2-phenyl-butyric acid was prepared from 4,5-dichloro-1-ethyl-1H-indole-2-carboxylic acid (4-piperidin-4-yl-phenyl)-amide and 3-phenyl-dihydro-furan-2,5-dione. LCMS for $C_{32}H_{31}Cl_2N_3O_4$ calcd. (m/e) 591, observed 592 (M+H).

Example 62

1-[2-(4-{4-[(4,5-Dichloro-1-ethyl-1H-indole-2-carbonyl)-amino]-phenyl}-piperidin-1-yl)-2-oxo-ethyl]-cyclopentanecarboxylic acid

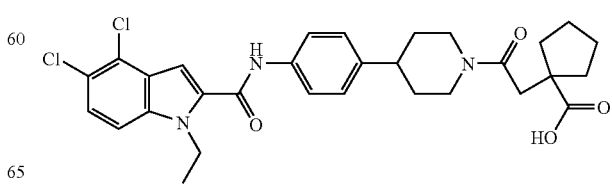

With a method similar to that used for the preparation of 4-(4-{4-[(4-ethoxy-1-ethyl-1H-indole-2-carbonyl)-amino]-phenyl}-piperidin-1-yl)-2,2-dimethyl-4-oxo-butyric acid, 1-[2-(4-{4-[(4,5-dichloro-1-ethyl-1H-indole-2-carbonyl)-amino]-phenyl}1-piperidin-1-yl)-2-oxo-ethyl]cyclopentanecarboxylic acid was prepared from 4,5-dichloro-1-ethyl-1H-indole-2-carboxylic acid (4-piperidin-4-yl-phenyl)-amide and 2-oxa-spiro[4,4]nonane-1,3-dione. LCMS for $C_{30}H_{33}Cl_2N_3O_4$ calcd. (m/e) 569, observed 570 (M+H).

Example 63

2-Cyclohexyl-4-(4-{4-[(4,5-dichloro-1-ethyl-1H-indole-2-carbonyl)-amino]-phenyl}-piperazin-1-yl)-4-oxo-butyric acid hydrochloride

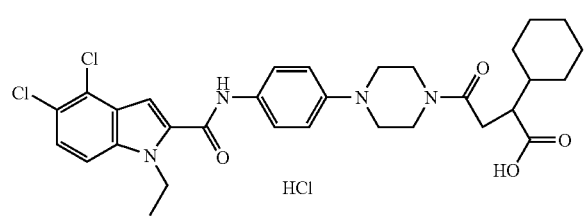

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 2-cyclohexyl-4-(4-{4-[(4,5-dichloro-1-ethyl-1H-indole-2-carbonyl)-amino]-phenyl}-piperazin-1-yl)-4-oxo-butyric acid was prepared from 4,5-dichloro-1-ethyl-1H-indole-2-carboxylic acid (4-piperazin-1-yl-phenyl)-amide and 3-cyclohexyl-dihydro-furan-2,5-dione. The waxy carboxylic acid was dissolved in methylene chloride and treated with hydrogen chloride in ether. Solvents were evaporated to provide the desired hydrochloride salt. LCMS for $C_{31}H_{36}Cl_2N_4O_4$ calcd. (m/e) 598, observed 599 (M+H).

Example 64

2-[2-(4-{4-[(4,5-Dichloro-1-ethyl-1H-indole-2-carbonyl)-amino]-phenyl}-piperazin-1-yl)-2-oxo-ethyl]-3-methyl-butyric acid

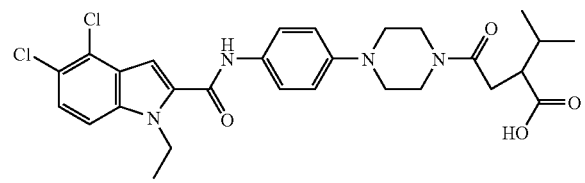

With a method similar to that used for the preparation of 4-(4-{5-[(4-chloro-benzo[b]thiophene-2-carbonyl)-amino]-pyridin-2-yl}-piperazin-1-yl)-2,2-dimethyl-4-oxo-butyric acid, 2-[2-(4-{4-[(4,5-dichloro-1-ethyl-1H-indole-2-carbonyl)-amino]-phenyl}-piperazin-1-yl)-2-oxo-ethyl]-3-methyl-butyric acid was prepared from 4,5-dichloro-1-ethyl-1H-indole-2-carboxylic acid (4-piperazin-1-yl-phenyl)- amide and 3-isopropyl-dihydro-furan-2,5-dione. LCMS for $C_{28}H_{32}Cl_2N_4O_4$ calcd. (m/e) 558, observed 559 (M+H).

Example 65

(S)-3-{4-[(4-Ethoxy-1-ethyl-1H-indole-2-carbonyl)-amino]-phenoxy}-pyrrolidine-1-carboxylic acid tert-butyl ester

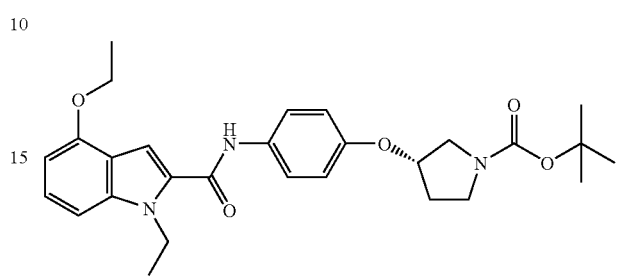

This compound was prepared from N-ethyl-4-ethoxy-indole-2-carboxylic acid and (S)-3-(4-amino-phenoxy)-pyrrolidine-1-carboxylic acid tert-butyl ester as described in the intermediate preparation section. LCMS for $C_{28}H_{35}N_3O_5$ calcd. (m/e) 493, observed 494 (M+H).

Example 66

4-((S)-3-{4-[(4-Ethoxy-1-ethyl-1H-indole-2-carbonyl)-amino]-phenoxy}-pyrrolidin-1-yl)-2,2-dimethyl-4-oxo-butyric acid

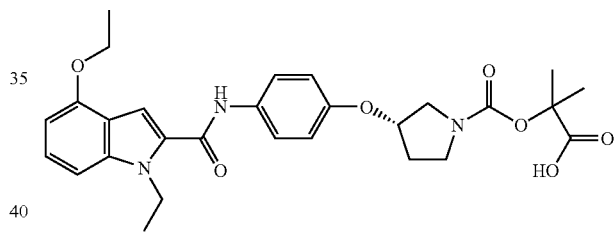

With a method similar to that used for the preparation of 4-{5-[(4-chloro-benzo[b]thiophene-2-carbonyl)-amino]-pyridin-2-yl}-piperazine-1-carboxylic acid tert-butyl ester, 4-((S)-3-{4-[(4-ethoxy-1-ethyl-1H-indole-2-carbonyl)-amino]-phenoxy}-pyrrolidin-1-yl)-2,2-dimethyl-4-oxo butyric acid was prepared from 4-ethoxy-1-ethyl-1H-indole-2-carboxylic acid [4-((S)-pyrrolidin-3-yloxy)-phenyl]-amide and 3,3-dimethyl-dihydro-furan-2,5-dione. LCMS for $C_{29}H_{35}N_3O_6$ calcd. (m/e) 521, observed 522 (M+H).

Example 67

4-(S)-3-{4-[(4-Ethoxy-1-ethyl-1H-indole-2-carbonyl)-amino]-phenoxy}-pyrrolidin-1-yl)-benzoic acid

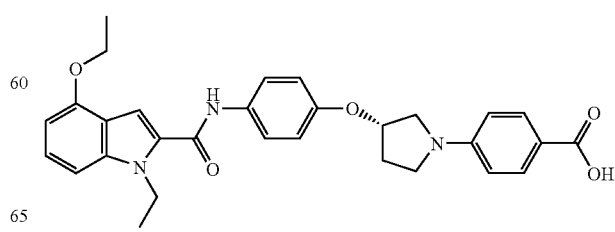

4-Ethoxy-1-ethyl-1H-indole-2-carboxylic acid [4-((S)-pyrrolidin-3-yloxy)-phenyl]-amide hydrochloride (103 mg, 0.24 mmol) was mixed with 4-bromo-benzoic acid tert-butyl ester (74 mg, 0.29 mmol) in dioxane (4 mL). To this solution was added tris(dibenzylideneacetone)dipalladium (Pd$_2$(dba)$_3$, 20 mg), (2',4',6'-triisopropyl-1,1'-biphenyl-2-yl)dicyclohexylphosphine (X-PHOS, 35 mg) and sodium tert-butoxide (70 mg, 0.72 mmol). The mixture was degassed with argon and then sealed. The stirred solution was heated at 105° C. for 2 hrs and solvents were evaporated. The residue was extracted with ethyl acetate and ammonium chloride solution. The organic layer was dried over sodium sulfate and then concentrated. The residue was purified through flash column chromatography using ethyl acetate in hexanes (5% to 60%) to give a white solid as 4-(S)-3-{4-[(4-ethoxy-1-ethyl-1H-indole-2-carbonyl)-amino]-phenoxy}-pyrrolidin-1-yl)-benzoic acid tert-butyl ester (100 mg).

The above tert-butyl ester (90 mg) was dissolved in dichloromethane (2 mL) and treated with trifluoroacetic acid (2 mL). The solution was stirred for 1 hr and solvents were evaporated. The residue was extracted with ethyl acetate and brine. The organic layer was dried and concentrated. The residue was triturated with ether to give 4-((S)-3-{4-[(4-ethoxy-1-ethyl-1H-indole-2-carbonyl)-amino]-phenoxy}-pyrrolidin-1-yl)-benzoic acid as a tan solid (50 mg). LCMS for $C_{30}H_{31}N_3O_5$ calcd. (m/e) 513, observed 512 (M−H).

Example 68

4-Ethoxy-1-ethyl-1H-indole-2-carboxylic acid (4-{4-[2-(2,4-dioxo-thiazolidin-5-yl)-acetyl]-piperazin-1-yl}-phenyl-amide hydrochloride

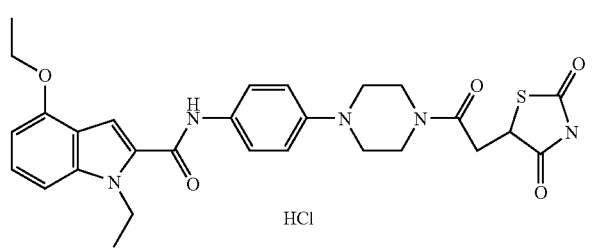

A mixture of (2,4-dioxo-thiazolidin-5-yl)-acetic acid (24 mg, 0.13 mmol), DMF (5 mL), EDCI (27 mg, 0.14 mmol) and DMAP (catalytic amount) was stirred at room temperature. N-Ethyl-4-ethoxy-1H-indole-2-carboxylic acid (4-piperazin-1-yl-phenyl)-amide (36 mg, 0.091 mmol) was added slowly. The reaction was stirred at room temperature for 1.5 hr then concentrated and the residue was taken up in 50 mL of EtOAc and washed with 50 mL of saturated ammonium chloride, brine and dried with anhydrous sodium sulfate. The solvent was removed and the product was dissolved in ethyl acetate and converted to the HCl salt with 1N HCl/diethyl ether, followed by filtration, to afford 4-ethoxy-1-ethyl-1H-indole-2-carboxylic acid (4-{4-[2-(2,4-dioxo-thiazolidin-5-yl)-acetyl]-piperazin-1-yl}-phenyl)-amide hydrochloride (24 mg, 45% yield). LCMS for $C_{28}H_{31}N_5O_5S$ calcd. (m/e) 549, observed 550 (M+H).

Example 69

4,5-Dichloro-1-ethyl-1H-indole-2-carboxylic acid (4-{4-[2-(2,4-dioxo-thiazolidin-5-yl)-acetyl]-piperazin-1-yl}-phenyl)-amide

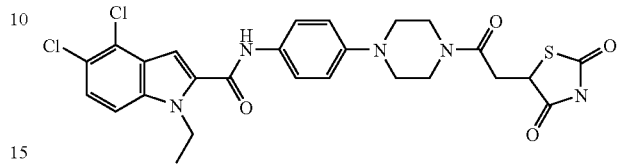

With a method similar to that used for the preparation of 4-ethoxy-1-ethyl-1H-indole-2-carboxylic acid (4-{4-[2-(2,4-dioxo-thiazolidin-5-yl)-acetyl]-piperazin-1-yl}-phenyl)-amide hydrochloride, 4,5-dichloro-1-ethyl-1,1-indole-2-carboxylic acid (4-{4-[2-(2,4-dioxo-thiazolidin-5-yl)-acetyl]-piperazin-1-yl}-phenyl)-amide was prepared from 4,5-dichloro-1-ethyl-1H-indole-2-carboxylic acid (4-piperazin-1-yl-phenyl)-amide and (2,4-dioxo-thiazolidin-5-yl)-acetic acid. LCMS for $C_{26}H_{25}Cl_2N_5O_4S$ calcd. (m/e) 573, observed 574 (M+H).

Example 70

4-(4-{4-[(4,5-Dichloro-1-ethyl-1H-indole-2-carbonyl)-amino]-phenyl}-piperazin-1-yl)-benzoic acid

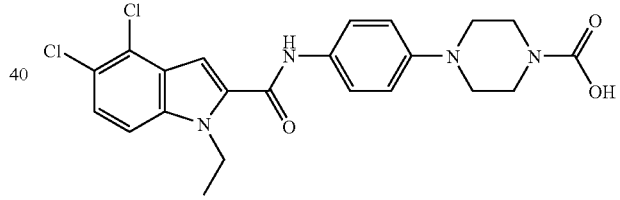

A mixture containing 4,5-dichloro-1-ethyl-1H-indole-2-carboxylic acid (4-piperazin-1-yl-phenyl)-amide hydrochloride (110 mg, 0.24 mmol), dioxane (6 mL), 4-bromo-benzoic acid tert-butyl ester (160 mg, 0.62 mmol), sodium tert-butoxide (128 mg, 1.33 mmol), Pd$_2$(dba)$_3$ (20 mg, 5% mol) and X-PHOS ligand (35 mg) was stirred under Ar, and heated for 2 hours at 100° C. The mixture was concentrated to dryness. The residue was taken up in 50 mL of EtOAc and washed with 50 mL of water, brine and dried with anhydrous sodium sulfate. The solvent was removed and the residue was triturated with methanol followed by hexanes. The solid was filtered to give 4-(4-{4-[(4,5-dichloro-1-ethyl-1H-indole-2-carbonyl)-amino]-phenyl}-piperazin-1-yl)-benzoic acid tert-butyl ester (70 mg).

The above tert-butyl ester was taken up in 2 mL of methylene chloride and 1 mL of trifluoroacetic acid and stirred for 2 hours. Solvents were removed and the crude product was taken up in ethyl acetate (50 mL), washed with brine, and dried with anhydrous sodium sulfate. The ethyl acetate solvent was removed and the crude product was triturated with ether to afford 4-(4-{4-[(4,5-dichloro-1-ethyl-1H-indole-2-carbonyl)-amino]-phenyl}-piperazin-1-yl)-benzoic acid as a tan solid (30 mg, 25% yield). LCMS for $C_{28}H_{26}Cl_2N_4O_3$ calcd. (m/e) 536, observed 535 (M−H).

Example 71

4-{4-[(7-Methoxy-3-methyl-1H-indole-2-carbonyl)-amino]-phenyl}-piperazine-1-carboxylic acid tert-butyl ester

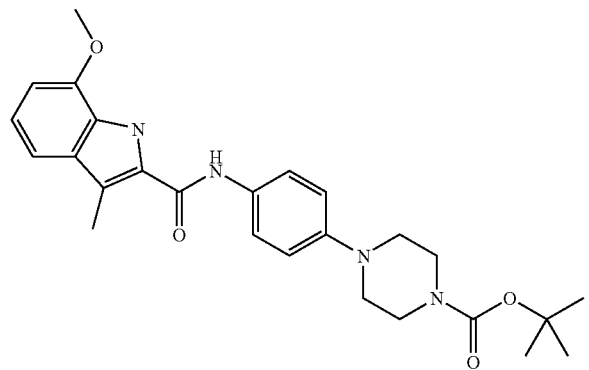

A mixture of 7-methoxy-3-methyl-1H-indole-2-carboxylic acid (61 mg, 0.3 mmol), 4-(4-amino-phenyl)-piperazine-1-carboxylic acid tert-butyl ester (83 mg, 0.3 mmol), N-hydroxybenzotriazole (61 mg, 0.45 mmol), and 1-ethyl-3-(3-dimethylaminopropyl)carbodiimide hydrochloride (86 mg, 0.45 mmol) in 1:1 dichloromethane/dimethylformamide was stirred at room temperature for overnight. After the reaction, solvent was concentrated. The resulted mixture was mixed with water and extracted with ethyl acetate twice. The organic layers were collected, combined, washed with brine before being dried over sodium sulfate, and then concentrated to give a solid. The crude product was purified by flash chromatography (Merck silica gel 60, 230-400 mesh, 0%-100% ethyl acetate in hexane) to give 40 mg of 4-{4-[(7-methoxy-3-methyl-1H-indole-2-carbonyl)-amino]-phenyl}-piperazine-1-carboxylic acid tert-butyl ester as an off-white solid. LCMS calcd for $C_{26}H_{32}N_4O_4$ (m/e) 464, obsd 465 (M+H).

Example 72

7-Methoxy-3-methyl-1H-indole-2-carboxylic acid {6-[(2-methoxy-ethyl)-methyl-amino]pyridin-3-yl}-amide

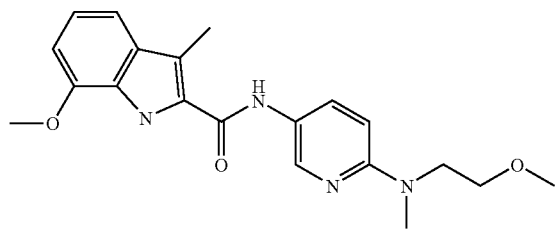

With a procedure similar to the example above, 7-methoxy-3-methyl-1H-indole-2-carboxylic acid {6-[(2-methoxy-ethyl)-methyl-amino]-pyridin-3-yl}-amide was prepared from 7-methoxy-3-methyl-1H-indole-2-carboxylic acid and $N^2$-(2-methoxy-ethyl)-$N^2$-methyl-pyridine-2,5-diamine. LCMS calcd for $C_{20}H_{24}N_4O_3$ (m/e) 368, obsd 369 (M+H).

Example 73

3-{4-[(7-Methoxy-3-methyl-1H-indole-2-carbonyl)-amino]-phenoxy}-pyrrolidine-1-carboxylic acid ethyl ester

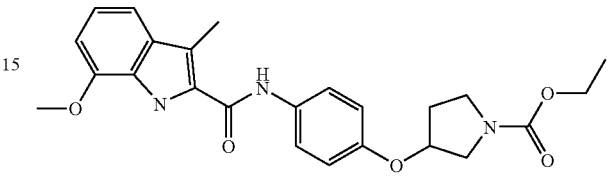

With a procedure similar to the example above, 3-{4-[(7-methoxy-3-methyl-1H-indole-2-carbonyl)-amino]-phenoxy}-pyrrolidine-1-carboxylic acid ethyl ester was prepared from 7-methoxy-3-methyl-1H-indole-2-carboxylic acid and 3-(4-amino-phenoxy)-pyrrolidine-1-carboxylic acid ethyl ester. LCMS calcd for $C_{24}H_{27}N_3O_5$ (m/e) 437, obsd 438 (M+H).

Example 74

4-(4-{4-[(7-Methoxy-3-methyl-1H-indole-2-carbonyl)-amino]-phenyl}-piperazin-1-yl)-2,2-dimethyl-4-oxo-butyric acid

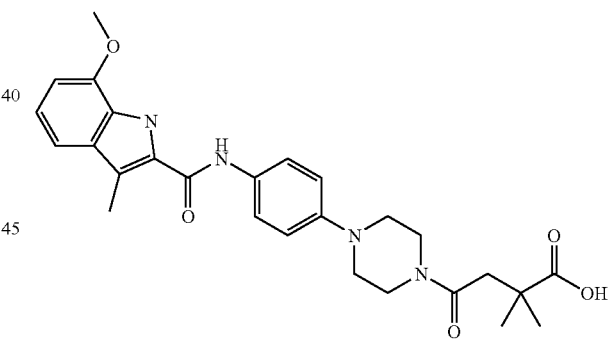

4-{4-[(7-Methoxy-3-methyl-1H-indole-2-carbonyl)-amino]-phenyl}-piperazine-1-carboxylic acid tert-butyl ester (139 mg, 0.3 mmol) (see example 1) was stirred in 5 mL of 1:3 TFA/$CH_2Cl_2$ at r.t. overnight, then concentrated. The residue was dissolved in 5 mL of 30:70 diisopropylethylamine/anhydrous dichloromethane, 2,2-dimethyl-succinic acid (72 mg, 0.49 mmol), N-hydroxybenzotriazole (61 mg, 0.45 mmol) and 1-ethyl-3-(3-dimethylaminopropyl)carbodiimide hydrochloride (86 mg, 0.45 mmol) were added. The reaction mixture was stirred at room temperature overnight. After the reaction, solvent was evaporated. The resulted mixture was mixed with water and extracted with ethyl acetate twice. The organic layers were collected, combined, washed with brine before dried over sodium sulfate, and then concentrated to give a solid. The crude product was purified by reverse phase HPLC (10%-80% acetonitrile in water) to gave 7 mg of 4-(4-{4-[(7-methoxy-3-methyl-1H-indole-2-carbonyl)-amino]-phenyl}-piperazin-1-yl)-2,2-dimethyl-4-oxo-butyric acid. LCMS calcd for $C_{27}H_{32}N_4O_5$ (m/e) 492, obsd 493 (M+H).

Example 75

(1S,2S)-2-(4-{4-[(7-Methoxy-3-methyl-1H-indole-2-carbonyl)-amino]-phenyl}-piperazine-1-carbonyl)-cyclopentanecarboxylic acid

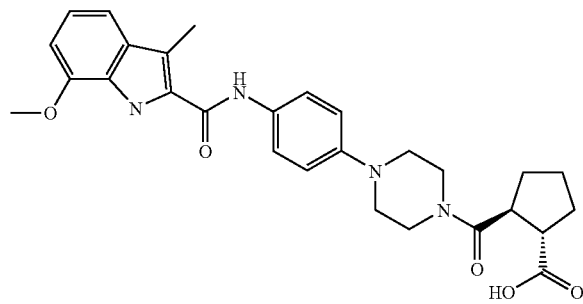

With a procedure similar to example above, (1S,2S)-2-(4-{4-[(7-methoxy-3-methyl-1H-indole-2-carbonyl)-amino]-phenyl}-piperazine-1-carbonyl)-cyclopentanecarboxylic acid was prepared from 4-{4-[(7-methoxy-3-methyl-1H-indole-2-carbonyl)-amino]-phenyl}-piperazine-1-carboxylic acid tert-butyl ester and (1S,2S)-cyclopentane-1,2-dicarboxylic acid. LCMS calcd for $C_{28}H_{32}N_4O_5$ (m/e) 504, obsd 505 (M+H).

Example 76 trans-4-(4-{4-[(7-Methoxy-3-methyl-1H-indole-2-carbonyl)-amino]-phenyl}-piperazine-1-carbonyl)-cyclohexanecarboxylic acid

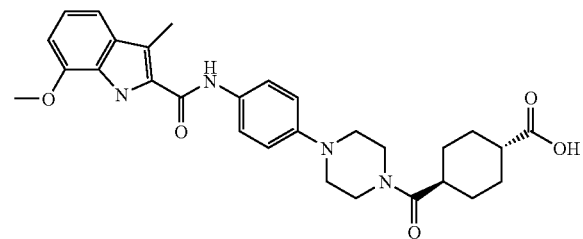

With a procedure similar to the example above, trans-4-(4-{4-[(7-methoxy-3-methyl-1H-indole-2-carbonyl)-amino]-phenyl}-piperazine-1-carbonyl)-cyclohexanecarboxylic acid was prepared from 4-{4-[(7-methoxy-3-methyl-1H-indole-2-carbonyl)-amino]-phenyl}-piperazine-1-carboxylic acid tert-butyl ester and trans-cyclohexane-1,4-dicarboxylic acid monomethyl ester, followed by a standard LiOH—H$_2$O saponification procedure to remove the methyl ester. LCMS calcd for $C_{29}H_{34}N_4O_5$ (m/e) 518, obsd 519 (M+H).

Example 77 trans-4-(4-{4-[(7-Methoxy-3-methyl-1H-indole-2-carbonyl)-amino]phenyl}-piperidine-1-carbonyl)-cyclohexanecarboxylic acid

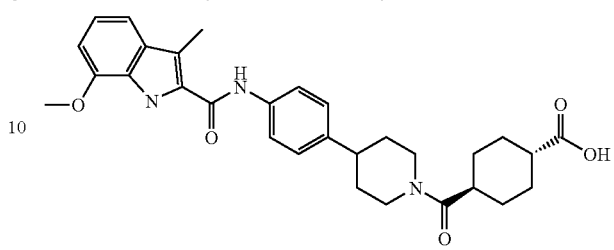

With a procedure similar to the example above, trans-4-(4-{4-[(7-methoxy-3-methyl-1H-indole-2-carbonyl)-amino]-phenyl}-piperidine-1-carbonyl)-cyclohexanecarboxylic acid was prepared from 4-{4-[(7-methoxy-3-methyl-1H-indole-2-carbonyl)-amino]-phenyl}-piperidine-1-carboxylic acid tert-butyl ester and trans-cyclohexane-1,4-dicarboxylic acid monomethyl ester, followed by a standard LiOH—H$_2$O saponification procedure to remove the methyl ester. LCMS calcd for $C_{30}H_{35}N_3O_5$ (m/e) 517, obsd 518 (M+H).

Example 78

4-{4-[(6,7-Diethoxy-3-methyl-benzofuran-2-carbonyl)-amino]-phenyl}-piperazine-1-carboxylic acid tert-butyl ester

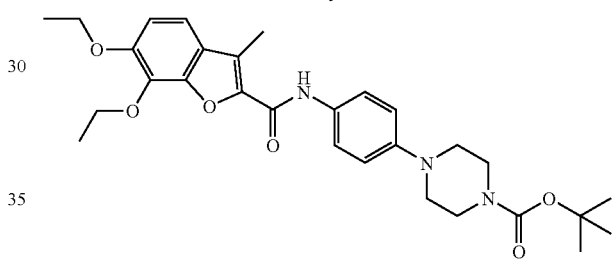

With a procedure similar to the example above, 4-{4-[(6,7-diethoxy-3-methyl-benzofuran-2-carbonyl)-amino]-phenyl}-piperazine-1-carboxylic acid tert-butyl ester was prepared from 6,7-diethoxy-3-methyl-benzofuran-2-carboxylic acid and 4-(4-amino-phenyl)-piperazine-1-carboxylic acid tert-butyl ester. LCMS calcd for $C_{29}H_{37}N_3O_6$ (m/e) 523, obsd 524 (M+H).

Example 79

4-{4-[(3-Methoxymethyl-benzofuran-2-carbonyl)-amino]-phenyl}-piperazine-1-carboxylic acid tert-butyl ester

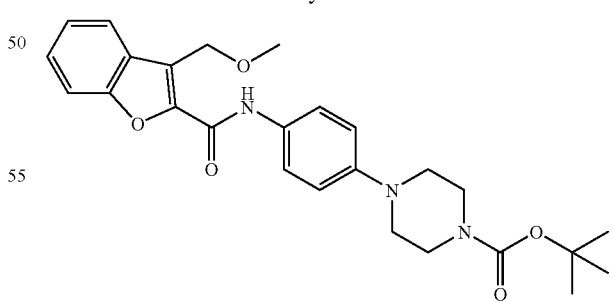

With a procedure similar to the example above, 4-{4-[(3-methoxymethyl-benzofuran-2-carbonyl)-amino]-phenyl}-piperazine-1-carboxylic acid tert-butyl ester was prepared from 3-methoxymethyl-benzofuran-2-carboxylic acid and 4-(4-amino-phenyl)-piperazine-1-carboxylic acid tert-butyl ester. LCMS calcd for $C_{26}H_{31}N_3O_5$ (m/e) 465, obsd 466 (M+H).

Example 80

3-{4-[(6,7-Diethoxy-3-methyl-benzofuran-2-carbonyl)-amino]-phenoxy}-pyrrolidine-1-carboxylic acid ethyl ester

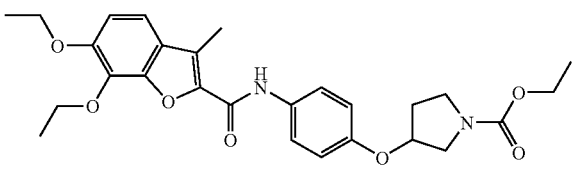

With a procedure similar to example above, 3-{4-[(6,7-diethoxy-3-methyl-benzofuran-2-carbonyl)-amino]-phenoxy}-pyrrolidine-1-carboxylic acid ethyl ester was prepared from 6,7-diethoxy-3-methyl-benzofuran-2-carboxylic acid and 3-(4-amino-phenoxy)-pyrrolidine-1-carboxylic acid ethyl ester. LCMS calcd for $C_{27}H_{32}N_2O_7$ (m/e) 496, obsd 497 (M+H).

Example 81

3-{4-[(3-Methoxymethyl-benzofuran-2-carbonyl)-amino]-phenoxy}-pyrrolidine-1-carboxylic acid ethyl ester

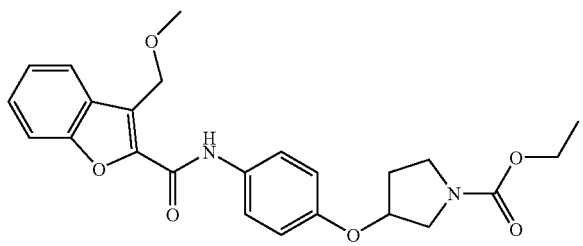

With a procedure similar to the example above, 3-{4-[(3-methoxymethyl-benzofuran-2-carbonyl)-amino]-phenoxy}-pyrrolidine-1-carboxylic acid ethyl ester was prepared from 3-methoxymethyl-benzofuran-2-carboxylic acid and 3-(4-amino-phenoxy)-pyrrolidine-1-carboxylic acid ethyl ester. LCMS calcd for $C_{24}H_{26}N_2O_6$ (m/e) 438, obsd 439 (M+H).

Example 82

7-Fluoro-3-methyl-benzofuran-2-carboxylic acid {6-[(2-methoxy-ethyl)-methyl-amino]pyridin-3-yl}-amide

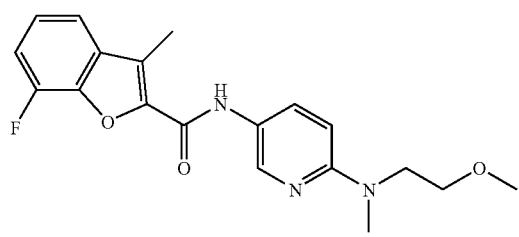

With a procedure similar to the example above, 7-fluoro-3-methyl-benzofuran-2-carboxylic acid {6-[(2-methoxy-ethyl)-methyl-amino]-pyridin-3-yl}-amide was prepared from 7-fluoro-3-methyl-benzofuran-2-carboxylic acid and $N^2$-(2-methoxy-ethyl)-$N^2$-methyl-pyridine-2,5-diamine.
LCMS calcd for $C_{19}H_{20}FN_3O_3$ (m/e) 357, obsd 358 (M+H).

Example 83

DGAT Phospholipid FlashPlate Assay

Materials for the assay were: PL-FlashPlate: Phospholipid FlashPlates from PerkinElmer, catalog number SMP108; DAG (1,2-Dioleoyl-sn-glycerol) 10 mM suspended in water containing 0.1% Triton X-100; $^{14}$C-Pal-CoA (palmitoyl coenzyme A, [palmitoyl-1-$^{14}$C]) from PerkinElmer, catalog number NEC-555 with a specific activity of 55 mCi/mmol; and DGAT pellet, with a protein concentration of 9.85 mg/ml.

Aqueous buffers were prepared or purchased as follows: The coating buffer (CB) was purchased from PerkinElmer, catalog number SMP900A; the reaction buffer (RB) was 50 mM Tris-HCl, pH 7.5, 100 mM NaCl, 0.01% BSA in water; the washing buffer (WB) is 50 mM Tris-HCl, pH 7.5, 100 mM NaCl, 0.05% deoxycholic acid sodium salt in water; the dilution buffer (DB) was 50 mM Tris-HCl, pH 7.5, 100 mM NaCl, 1 mM EDTA, 0.2% Triton X-100 in water.

1,2-Dioleoyl-sn-glycerol (DAG, 10 mmoles) was diluted to 500 μM with coating buffer (CB). The diluted DAG solution was then added to 384-well PL-FlashPlates at 60 μl per well, and incubated at room temperature for 2 days. The coated plates were then washed twice with washing buffer (WB) before use. Test compounds were serial diluted to 2000, 666.7, 222.2, 74.1, 24.7, 8.2, 2.7 and 0.9 μM in 100% DMSO. Diluted compound were further diluted 10 fold with reaction buffer (RB). $^{14}$C-Pal-CoA was diluted to 8.3 μM with RB. The DGAT pellet was diluted to 0.13 mg protein/ml with dilution buffer (DB) immediately before it was added to the PL-FlashPlates to start the reaction. 20 μl of the RB-diluted compounds (or 10% DMSO in RB for Total and Blank), 15 μl of RB diluted 14C-Pal-CoA and 15 μl of DB diluted DGAT pellet (DB without DGAT for Blanks) were transferred to each well of the PL-FlashPlates. The reaction mixtures were incubated at 37° C. for 1 hour. The reactions were stopped by washing 3 times with WB. Plates were sealed with Top-seal and read on a Topcount instrument.

Calculation of $IC_{50}$: The $IC_{50}$ values for each compound were generated using an Excel template. The Topcount rpm readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following:

$$(A+((B-A)/(1+((x/C)^\wedge D)))),$$

with A and B as the bottom and top of the curve (highest and lowest inhibition), respectively, and C as $IC_{50}$ and D as Hill Coefficient of the compound. The results are summarized in Table I below:

TABLE 1

| Compound of Example # | DGAT Inhibition Activity $IC_{50}$ (μM) |
| --- | --- |
| 1 | 0.292 |
| 2 | 0.032 |

TABLE 1-continued

| Compound of Example # | DGAT Inhibition Activity IC$_{50}$ (µM) |
|---|---|
| 3 | 0.479 |
| 4 | 0.085 |
| 5 | 0.18 |
| 6 | 0.189 |
| 7 | 0.316 |
| 8 | 0.528 |
| 9 | 0.333 |
| 10 | 0.328 |
| 11 | 0.105 |
| 12 | 0.273 |
| 13 | 0.283 |
| 14 | 0.433 |
| 15 | 0.183 |
| 16 | 0.248 |
| 17 | 0.27 |
| 18 | 0.255 |
| 19 | 0.08 |
| 20 | 0.084 |
| 21 | 0.282 |
| 22 | 0.086 |
| 23 | 0.571 |
| 24 | 0.512 |
| 25 | 0.127 |
| 26 | 0.145 |
| 27 | 0.826 |
| 28 | 0.385 |
| 29 | 0.98 |
| 30 | 0.824 |
| 31 | 0.38 |
| 32 | 0.495 |
| 33 | 0.662 |
| 34 | 0.683 |
| 35 | 0.351 |
| 36 | 0.856 |
| 37 | 0.425 |
| 38 | 0.102 |
| 39 | 0.312 |
| 40 | 0.797 |
| 41 | 0.937 |
| 42 | 0.75 |
| 43 | 0.161 |
| 44 | 0.489 |
| 45 | 0.668 |
| 46 | 0.303 |
| 47 | 0.28 |
| 48 | 0.396 |
| 49 | 0.594 |
| 50 | 0.929 |
| 51 | 0.343 |
| 52 | 0.229 |
| 53 | 0.209 |
| 54 | 0.309 |
| 55 | 0.414 |
| 56 | 0.671 |
| 57 | 0.548 |
| 58 | 0.247 |
| 59 | 0.821 |
| 60 | 0.21 |
| 61 | 0.79 |
| 62 | 0.24 |
| 63 | 0.351 |
| 64 | 0.164 |
| 65 | 0.701 |
| 66 | 0.208 |
| 67 | 0.296 |
| 68 | 0.289 |
| 69 | 0.236 |
| 70 | 0.319 |
| 71 | 0.188 |
| 72 | 0.117 |
| 73 | 0.09 |
| 74 | 0.064 |
| 75 | 0.372 |
| 76 | 0.058 |
| 77 | 0.057 |
| 78 | 0.848 |
| 79 | 0.94 |
| 80 | 0.583 |
| 81 | 0.72 |
| 82 | 0.43 |

It is to be understood that the invention is not limited to the particular embodiments of the invention described above, as variations of the particular embodiments may be made and still fall within the scope of the appended claims.

What is claimed is:

1. A compound of formula (I):

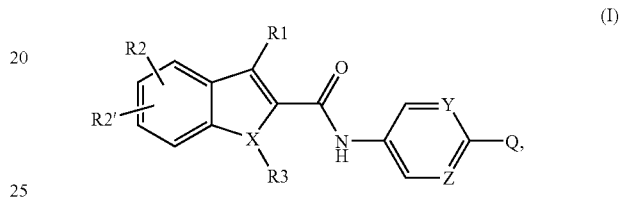

wherein:
X is oxygen, sulfur or nitrogen;
Y is carbon or nitrogen;
Z is carbon or nitrogen;
R1 is lower alkyl, halo lower alkyl, alkoxy, lower alkyl alkoxy or absent;
R2, R2', independently of each other, is halogen, alkoxy, lower alkyl, haloloweralkyl, haloalkoxy, benzyloxy or absent;
R3 is hydrogen or lower alkyl, wherein if X is oxygen or sulfur, then R3 is absent; and
Q is piperazine-1-carboxylic acid lower alkyl ester, piperidine-1-carboxylic acid lower alkyl ester, piperazin-1-yl-2,2-dimethyl-4-oxo-lower akanoic acid, piperidin-1-yl-2,2-dimethyl-4-oxo-lower alkanoic acid, piperazine-1-carbonyl-4-cyclohexanecarboxylic acid benzyl ester, piperazine-1-carbonyl-4-cyclohexanecarboxylic acid, piperidine-1-carbonyl-4-cyclohexanecarboxylic acid, piperazine-1-carbonyl-2-cyclopentanecarboxylic acid, N-lower alkoxy lower alkyl-N-lower alkyl-amino, N-cycloloweralkyl-N-lower alkyl-amino, N-pyrrolidine-1-carboxylic acid lower alkyl ester, O-pyrrolidine-1-carboxylic acid lower alkanoic ester, O-pyrrolidine-1-carboxylic acid lower alkyl ester, pyrrolidine-3-ylamino-1-carboxylic acid lower alkyl ester, pyrrolidin-3-ylamino-1-carboxylic acid lower alkyl amide, piperidin-1-yl-4-oxo-2-phenyl-lower alkanoic acid, piperidine-1-carbonyl-2-cyclopentanecarboxylic acid, piperidin-1-yl-2-oxo-lower alkyl-cyclopentanecarboxylic acid, piperazin-1-yl-4-oxo-lower alkyl acid, piperidin-1-yl-4-oxo-lower alkanoic acid, piperazin-1-yl-2-oxo-ethyl-3-methyl-lower alkanoic acid, piperazin-1-yl-4-oxo-2-cyclohexyl-butyric acid, pyrrolidine-3-oxy-1-carboxylic acid lower alkyl ester, pyrrolidine-3-oxy-1-carboxylic acid lower alkyl ester, pyrrolidin-3-oxy-1-yl-2,2-dimethyl-4-oxo-lower alkanoic acid, pyrrolidin-3-oxy-1-yl-4-benzoic acid, 2,4-dioxo-thiazolidin-5-yl-acetyl-piperazin-1-yl or piperazin-1-yl-4-benzoic acid, or a pharmaceutically acceptable salt thereof.

2. The compound according to claim 1, wherein X is sulfur.

3. The compound according to claim 1, wherein X is nitrogen.

4. The compound according to claim 1, wherein Y is carbon.

5. The compound according to claim, 1, wherein Z is nitrogen.

6. The compound according to claim 1, wherein Z is carbon.

7. The compound according to claim 1, wherein R1 is hydrogen or lower alkyl.

8. The compound according to claim 1, wherein R2 or R2', independently of each other, is alkoxy, lower alkyl or absent.

9. The compound according to claim 1, wherein R3 is lower alkyl or hydrogen.

10. The compound according to claim 1, wherein Q is piperazine-1-carboxylic acid tert-butyl ester, piperazine-1-carboxylic acid ethyl ester, piperazin-1-yl-2,2-dimethyl-4-oxo-butyric acid, piperidin-1-yl-2,2-dimethyl-4-oxo-butyric acid, piperazine-1-carbonyl-trans-4-cyclohexanecarboxylic acid, piperidine-1-carbonyl-trans-4-cyclohexanecarboxylic acid, (1R, 2R)-piperazine-1-carbonyl-2-cyclopentanecarboxylic acid, N-2-methoxyethyl-N-methyl-amino, N-cyclopropyl-N-methyl-amino or (S)-pyrrolidin-3-ylamino-1-carboxylic acid ethyl ester.

11. The compound according to claim 1, wherein Q is piperidin-1-yl-4-oxo-2-phenyl-butyric acid, piperidin-1-yl-2-oxo-ethyl-cyclopentanecarboxylic acid, piperazin-1-yl-4-oxo-butyric acid, piperazin-1-yl-2-oxo-ethyl-3-methyl-butyric acid, (S)-pyrrolidin-3-ylamino-1-carboxylic acid tert-butyl amide, (S)-pyrrolidin-3-yloxy-1-yl-2,2-dimethyl-4-oxo-butyric acid, (S)-pyrrolidin-3-yloxy-1-yl-4-benzoic acid, (S)-pyrrolidin-3-yloxy-1-carboxylic acid ethyl ester, or 2,4-dioxo-thiazolidin-5-yl-acetyl-piperazin-1yl.

12. A compound, selected from the group consisting of:
4-(4-{5-[(4-chloro-benzo[b]thiophene-2-carbonyl)-amino]-pyridin-2-yl}-piperazin-1-yl)-2,2-dimethyl-4-oxo-butyrie acid,
4-(4-{5-[(5-bromo-benzo[b]thiophene-2-carbonyl)-amino]-pyridin-2-yl}-piperazin-1-yl)-2,2-dimethyl-4-oxo-butyric acid,
4-(4-{5-[(4,5-dichloro-1-ethyl-1H-indole-2-carbonyl)-amino]-pyridin-2-yl}-piperazin-1-yl)-2,2-dimethyl-4-oxo-butyric acid,
trans-4-(4-{5-[(1-ethyl-4-methoxy-1H-indole-2-carbonyl)-amino]-pyridin-2-yl}-piperazine-1-carbonyl)-cyclohexane carboxylic acid,
(1R,2R)-2-(4-4-[(4-ethoxy-1-ethyl-1H-indole-2-carbonyl)-amino]-phenyl}-piperazine-1-carbonyl)-cyclopentanecarboxylic acid,
(S)-3-{5-[(4-chloro-benzo[b]thiophene-2-carbonyl)-amino]-pyridin-2-ylamino}-pyrrolidine-1-carboxylic acid ethyl ester,
1-ethyl-4-methyl-1H-indole-2-carboxylic acid [6-((S)-1-tert-butylcarbarnoyl-pyrrolidin-3-ylamino)-pyridin-3-yl]-amide,
4-(4-{4-[(4,5-dichloro-1-ethyl-1H-indole-2-carbonyl)-amino]-phenyl}-piperazin-1-yl)-2,2-dimethyl-4-oxo-butyric acid,
4-((S)-3-{4-[(4-ethoxy-1-ethyl-1H-indole-2-carbonyl)-amino]-phenoxy}-pyrrolidin-1-yl)-2,2-dimethyl-4-oxo butyric acid,
4-((S)-3-{4-[(4-ethoxy-1-ethyl-1H-indole-2-carbonyl)-amino]-phenoxy}-pyrrolidin-1-yl)-benzoic acid,
4-ethoxy-1-ethyl-1H-indole-2-carboxylic acid (4-{4-[2-(2,4-dioxo-thiazolidin-5-yl)-acetyl]-piperazin-1-yl}-phenyl)-amide,
3-{4-[(7-methoxy-3-methyl-1H-indole-2-carbonyl)-amino]-phenoxyl}-pyrrolidine-1-carboxylic acid ethyl Ester,
4-(4-{4-[(7-methoxy-3-methyl-1H-indole-2-carbonyl)-amino]-phenyl}-piperazin-1-yl)-2,2-dimethyl-4-oxo-butyric acid,
trans-4-(4-{4-[(7-methoxy-3-methyl-1H-indole-2-carbonyl)-amino]-phenyl}-piperazine-1-carbonyl)-cyclohexanecarboxylic acid and
trans-4-(4-{4-[(7-methoxy-3-methyl-1H-indole-2-carbonyl)-amino]-phenyl}-piperidine-1-carbonyl)-cyclohexanecarboxylic acid or a pharmaceutical acceptable salt thereof.

13. The compound of claim 1 wherein said compound has the formula:

or a pharmaceutically acceptable salt thereof.

14. The compound of claim 13 wherein Q is piperazine-1-carboxylic acid lower alkyl ester, piperazin-1-yl-2,2-dimethyl-4-oxo-lower alkanoic acid, piperazine-1-carbonyl-4-cyclohexanecarboxylic acid benzyl ester, piperazine-1-carbonyl-4-cyclohexanecarboxylic acid, piperazine-1-carbonyl-2-cyclopentanecarboxylic acid, piperazin-1-yl-4-oxo-lower alkanoic acid, piperidin-1-yl-4-oxo-lower alkanoic acid, piperazin-1-yl-2-oxo-ethyl-3-methyl-lower alkanoic acid, piperazin-1-yl-4-oxo-2-cyclohexyl-lower alkanoic acid, 2,4-dioxo-thiazolidin-5-yl-acetyl-piperazin-1-yl or piperazin-1-yl-4-lower alkanoic acid.

15. The compound of claim 14 wherein said compound is 4-(4-{5-[(4-ethoxy-1-ethyl-1H-indole-2-carbonyl)-amino]-pyridin-2-yl}-piperazin-1-yl)-2,2-dimethyl-4-oxo-butyric acid or a pharmaceutically acceptable salt thereof.

16. The compound of claim 14 wherein said compound is 4-{5-[(1-ethyl-4,6-dimethoxy-1H-indole-2-carbonyl)-amino]-pyridin-2-yl}-piperazine-1-carboxylic acid tert-butyl ester or a pharmaceutically acceptable salt thereof.

17. The compound of claim 14 wherein said compound is 4-(4-{5-[(4,5-dichloro-1-ethyl-1H-indole-2-carbonyl)-amino]-pyridin-2-yl}-piperazin-1-yl)-2,2-dimethyl-4-oxo-butyric acid or a pharmaceutically acceptable salt thereof.

18. The compound of claim 14 wherein said compound is 4-(4-{5-[(1-ethyl-4-methoxy-1H-indole-2-carbonyl)-amino]-pyridin-2-yl)-piperazine-1-carbonyl)-cyclohexanecarboxylic acid or a pharmaceutically acceptable salt thereof.

19. The compound of claim 14 wherein said compound is 4-(4-{5-[(1-ethyl-4-methoxy-1H-indole-2-carbonyl)-amino]-pyridin-2-yl}-piperazine-1-carbonyl)-cyclohexanecarboxylic acid benzyl ester or a pharmaceutically acceptable salt thereof.

20. The compound of claim 14 wherein said compound is 4-{5-[(4-chloro-benzo[b]thiophene-2-carbonyl)-amino]-pyridin-2-yl}-piperazine-1-carboxylic acid tert-butyl ester or a pharmaceutically acceptable salt thereof.

21. The compound of claim 14 wherein said compound is 4-{5-[(4-ethoxy-1-ethyl-1H-indole-2-carbonyl)-amino]-pyridin-2-yl}-piperazine-1-carboxylic acid tert-butyl ester or a pharmaceutically acceptable salt thereof.

22. The compound of claim 13 wherein Q is N-lower alkoxy lower alkyl-N-lower alkyl-amino or N-cyclolower-alkyl-N-lower alkyl-amino.

23. The compound of claim 22 wherein said compound is 1-ethyl-5-trifluoromethoxy-1H-indole-2-carboxylic acid {6-[(2-methoxy-ethyl)-methyl-amino]-pyridin-3-yl}-amide or a pharmaceutically acceptable salt thereof.

24. The compound of claim 22 wherein said compound is 2-(4-{4-[(4-ethoxy-1-ethyl-1H-indole-2-carbonyl)-amino]phenyl}-piperidine-1-carbonyl)-cyclopentanecarboxylic acid or a pharmaceutically acceptable salt thereof.

25. The compound of claim 22 wherein said compound is 1-ethyl-5-methoxy-1H-indole-2-carboxylic acid {6-[(2-methoxy-ethyl)-methyl-amino]-pyridin-3-yl}-amide or a pharmaceutically acceptable salt thereof.

26. The compound of claim 22 wherein said compound is 5-chloro-1-ethyl-1H-indole-2-carboxylic acid [6-(cyclopropyl-methyl-amino)-pyridin-3-yl]amide or a pharmaceutically acceptable salt thereof.

27. The compound of claim 13 wherein Q is N-pyrrolidine-1-carboxylic acid lower alkyl ester, O-pyrrolidine-1-carboxylic acid lower alkanoic ester, O-pyrrolidine-1-carboxylic acid lower alkyl ester, pyrrolidine-3-ylamino-1-carboxylic acid lower alkyl ester, pyrrolidin-3-ylamino-1-carboxylic acid tert-butyl amide, pyrrolidine-3-oxy-1-carboxylic acid lower alkyl ester, pyrrolidine-3-oxy-1-carboxylic acid lower alkyl ester, pyrrolidin-3-oxy-1-yl-2,2-dimethyl-4-oxo-lower alkanoic acid, or pyrrolidin-3-oxy-1-yl-4-benzoic acid.

28. The compound of claim 27 wherein said compound is 3-{5-[(5-bromo-1-ethyl-1H-indole-2-carbonyl)-amino]-pyridin-2-ylamino}-pyrrolidine-1-carboxylic acid ethyl ester or a pharmaceutically acceptable salt thereof.

29. The compound of claim 27 wherein said compound is 3-{5-[(1-ethyl-5-methoxy-1H-indole-2-carbonyl)-amino]-pyridin-2-ylamino}-pyrrolidine-1-carboxylic acid ethyl ester or a pharmaceutically acceptable salt thereof.

30. The compound of claim 27 wherein said compound is 1-ethyl-4-methyl-1H-indole-2-carboxylic acid [6-1-tert-butylcarbamoyl-pyrrolidin-3-ylamino)-pyridin-3-yl]-amide or a pharmaceutically acceptable salt thereof.

31. The compound of claim 27 wherein said compound is (3-{5-[(1-ethyl-4,6-dimethoxy-1H-indole-2-carbonyl)-amino]-pyridin-2-ylamino}pyrrolidine-1-carboxylic acid ethyl ester or a pharmaceutically acceptable salt thereof.

32. The compound of claim 27 wherein said compound is (S)-3-{5-[(1-ethyl-4-methyl-1H-indole-2-carbonyl)-amino]-pyridin-2-ylamino}-pyrrolidine-1-carboxylic acid ethyl ester or a pharmaceutically acceptable salt thereof.

33. The compound of claim 27 wherein said compound is 3-{5-[(4-ethoxy-1-ethyl-1H-indole-2-carbonyl)-amino]-pyridin-2-ylamino}-pyrrolidine-1-carboxylic acid ethyl ester or a pharmaceutically acceptable salt thereof.

34. The compound of claim 1 wherein said compound is

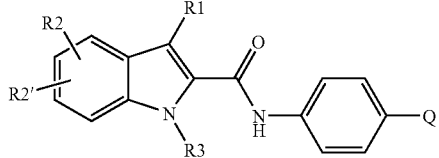

or a pharmaceutically acceptable salt thereof.

35. The compound of claim 34 wherein Q is piperazine-1-carboxylic acid lower alkyl ester, piperazin-1-yl-2,2-dimethyl-4-oxo-lower alkanoic acid, piperazine-1-carbonyl-4-cyclohexanecarboxylic acid benzyl ester, piperazine-1-carbonyl-4-cyclohexanecarboxylic acid, piperazine-1-carbonyl-2-cyclopentanecarboxylic acid, piperazin-1-yl-4-oxo-lower alkanoic acid, piperidin-1-yl-4-oxo-lower alkanoic acid, piperazin-1-yl-2-oxo-ethyl-3-methyl-lower alkanoic acid, piperazin-1-yl-4-oxo-2-cyclohexyl-lower alkanoic acid, 2,4-dioxo-thiazolidin-5-yl-acetyl-piperazin-1-yl or piperazin-1-yl-4-lower alkanoic acid.

36. The compound of claim 35 wherein said compound is (2-(4-{4-[(4-ethoxy-1-ethyl-1H-indole-2-carbonyl)-amino]-phenyl}-piperazine-1-carbonyl)-cyclopentanecarboxylic acid or a pharmaceutically acceptable salt thereof.

37. The compound of claim 35 wherein said compound is 4-(4-{4-[(4,5-diehloro-1-ethyl-1H-indole-2-carbonyl)-amino]-phenyl}-piperazin-1-yl)-2,2-dimethyl-4-oxo-butyric acid or a pharmaceutically acceptable salt thereof.

38. The compound of claim 35 wherein said compound is 4-ethoxy-1-ethyl-1H-indole-2-carboxylic acid (4-{4-[2-(2,4-dioxo-thiazolidin-5-yl)-acetyl]-piperazin-1-yl}-phenyl)-amide or a pharmaceutically acceptable salt thereof.

39. The compound of claim 35 wherein said compound is 4-(4-{4-[(7-methoxy-3-methyl-1H-indole-2-carbonyl)-amino]-phenyl}-piperazin-1-yl)-2,2-dimethyl-4-oxo-butyric acid or a pharmaceutically acceptable salt thereof.

40. The compound of claim 35 wherein said compound is 4-(4-{4-[(7-methoxy-3-methyl-1H-indole-2-carbonyl)-amino]-phenyl}-piperazine-1-carbonyl)-cyclohexanecarboxylic acid or or a pharmaceutically acceptable salt thereof.

41. The compound of claim 34 wherein Q is piperidin-1-yl-2,2-dimethyl-4-oxo-lower alkanoic acid, piperidine-1-carbonyl-trans-4-cyclohexanecarboxylic acid, piperidin-1-yl-4-oxo-2-phenyl-lower alkanoic acid, piperidine-1-carbonyl-2-cyclopentanecarboxylic acid, piperidin-1-yl-2-oxo-ethyl-cyclopentanecarboxylic acid, or piperidin-1-yl-4-oxo-lower alkanoic acid.

42. The compound of claim 41 wherein said compound is 4-(4-{4-[(7-methoxy-3-methyl-1h-indole-2-carbonyl)-amino]-phenyl}-piperidine-1-carbonyl)-cyclohexanecarboxylic acid or pharmaceutically acceptable salts thereof.

43. The compound of claim 34 wherein Q is N-pyrrolidine-1-carboxylic acid lower alkyl ester, O-pyrrolidine-1-carboxylic acid lower alkanoic ester, O-pyrrolidine-1-carboxylic acid lower alkyl ester, pyrrolidine-3-ylamino-1-carboxylic acid lower alkyl ester, pyrrolidine-3-ylamino-1-carboxylic acid tert-butyl amide, pyrrolidine-3-oxy-1-carboxylic acid lower alkyl ester, pyrrolidine-3-oxy-1-carboxylic acid lower alkyl ester, pyrrolidin-3-oxy-1-yl-2,2-dimethyl-4-oxo-lower alkanoic acid, or pyrrolidin-3-oxy-1-yl-4-benzoic acid.

44. The compound of claim 43 wherein said compound is 4-3-{4-[(4-ethoxy-1-ethyl-1H-indole-2-carbonyl)-amino]-phenoxy}-pyrrolidin-1-yl)-2,2-dimethyl-4-oxo-butyric acid or a pharmaceutically acceptable salt thereof.

45. The compound of claim 43 wherein said compound is 4-((S)-3-{4-[(4-ethoxy-1-ethyl-1H-indole-2-carbonyl)-amino]-phenoxy}-pyrrolidin-1-yl)-benzoic acid or a pharmaceutically acceptable salt thereof.

46. The compound of claim 43 wherein said compound is 3-{4-[(7-methoxy-3-methyl-1H-indole-2-carbonyl)-amino]-phenoxyl-pyrrolidine-1-carboxylic acid ethyl ester or a pharmaceutically acceptable salt thereof.

47. The compound of claim 1 wherein said compound has the formula:

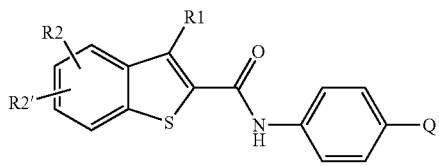

or a pharmaceutically acceptable salt thereof.

48. The compound of claim 47 wherein Q is piperazine-1-carboxylic acid lower alkyl ester, piperazin-1-yl-2,2-dimethyl-4-oxo-lower alkanoic acid, piperazine-1-carbonyl-4-cyclohexanecarboxylic acid benzyl ester, piperazine-1-carbonyl-4-cyclohexanecarboxylic acid, piperazine-1-carbonyl-2-cyclopentanecarboxylic acid, piperazin-1-yl-4-oxo-lower alkanoic acid, piperidin-1-yl-4-oxo-lower alkanoic acid, piperazin-1-yl-2-oxo-ethyl-3-methyl-lower alkanoic acid, piperazin-1-yl-4-oxo-2-cyclohexyl-lower alkanoic acid, 2,4-dioxo-thiazolidin-5-yl-acetyl-piperazin-1-yl or piperazin-1-yl-4-lower alkanoic acid.

49. The compound of claim 48 wherein said compound is 4-(4-{5-[(4-chloro-benzo[b]thiophene-2-carbonyl)-amino]-pyridin-2-yl}-piperazin-1-yl)-2,2-dimethyl-4-oxo-butyric acid.

50. The compound of claim 48 wherein said compound is 4-(4-{5-[(5-bromo-benzo[b]thiophene-2-carbonyl)-amino]-pyridin-2-yl}-piperazin-1-yl)-2,2-dimethyl-4-oxo-butyric acid.

51. The compound of claim 47 wherein Q is N-pyrrolidine-1-carboxylic acid lower alkyl ester, O-pyrrolidine-1-carboxylic acid lower alkanoic ester, O-pyrrolidine-1-carboxylic acid lower alkyl ester, pyrrolidine-3-ylamino-1-carboxylic acid lower alkyl ester, pyrrolidin-3-ylamino-1-carboxylic acid tert-butyl amide, pyrrolidine-3-oxy-1-carboxylic acid lower alkyl ester, pyrrolidine-3-oxy-1-carboxylic acid lower alkyl ester, pyrrolidin-3-oxy-1-yl-2,2-dimethyl-4-oxo-lower alkanoic acid, or pyrrolidin-3-oxy-1-yl-4-benzoic acid.

52. The compound of claim 51 wherein said compound is 3-{5-[(4-chloro-benzo[b]thiophene-2-carbonyl)-amino]-pyridin-2-ylamino}-pyrrolidine-1-carboxylic acid ethyl ester hydrochloride or pharmaceutically acceptable salts thereof.

\* \* \* \* \*